(12) United States Patent
Jang

(10) Patent No.: US 8,221,120 B2
(45) Date of Patent: Jul. 17, 2012

(54) DENTAL PROSTHESIS AND MANUFACTURING METHOD THEREOF

(76) Inventor: Wan Young Jang, Busan (KR)

( * ) Notice: Subject to any disclaimer, the term of this patent is extended or adjusted under 35 U.S.C. 154(b) by 322 days.

(21) Appl. No.: 12/529,696

(22) PCT Filed: Mar. 14, 2008

(86) PCT No.: PCT/KR2008/001472
§ 371 (c)(1),
(2), (4) Date: Sep. 2, 2009

(87) PCT Pub. No.: WO2008/114974
PCT Pub. Date: Sep. 25, 2008

(65) Prior Publication Data
US 2010/0035209 A1 Feb. 11, 2010

(30) Foreign Application Priority Data

| Mar. 16, 2007 | (KR) | 10-2007-0026075 |
| Jul. 18, 2007 | (KR) | 10-2007-0071458 |
| Sep. 2, 2007 | (KR) | 10-2007-0088722 |
| Oct. 9, 2007 | (KR) | 10-2007-0101464 |
| Oct. 16, 2007 | (KR) | 10-2007-0103924 |

(51) Int. Cl.
*A61C 13/10* (2006.01)
(52) U.S. Cl. ....................................................... 433/194
(58) Field of Classification Search ................ 433/181, 433/190–194, 172–176
See application file for complete search history.

(56) References Cited

U.S. PATENT DOCUMENTS

| 2,111,787 A | * | 3/1938 | Knowles | 433/172 |
| 4,406,622 A | * | 9/1983 | Yoon | 433/172 |
| 5,213,501 A | * | 5/1993 | Watkins | 433/172 |
| 5,630,717 A | | 5/1997 | Zuest et al. | |
| 6,460,601 B1 | | 10/2002 | Brehm | |

FOREIGN PATENT DOCUMENTS

| FR | 02621480 A1 | 4/1989 |
| JP | 11-290351 | 10/1999 |
| JP | 2000-300584 | 10/2000 |
| JP | 2004-321645 | 11/2004 |
| KR | 1020010044362 A | 6/2001 |
| KR | 1020010050050 A | 6/2001 |
| KR | 1020010051712 A | 6/2001 |
| KR | 200303425 Y1 | 7/2003 |
| KR | 1020050014391 A | 2/2005 |
| KR | 200396918 Y1 | 9/2005 |
| KR | 100598485 B1 | 3/2006 |
| KR | 100615983 B1 | 8/2006 |
| KR | 1020070008374 A | 1/2007 |
| KR | 1020070026723 A | 3/2007 |
| KR | 1020090024599 A | 3/2009 |
| WO | WO2007010338 A1 | 1/2007 |

* cited by examiner

*Primary Examiner* — Sunil K Singh

(57) ABSTRACT

The present invention relates to a dental prosthesis, and more particularly, to a screw-engagement type dental prosthesis which enables non-preparation of the natural tooth because it is manufactured by division into two pieces or three pieces, which can be simply installed, and in which the occlusal pressure can be uniformly dispersed. Also, the present invention relates to a method of casting a screw-engagement type dental prosthesis by using a bolt made of carbon or ceramics. Furthermore, a keeper and a body are engaged with each other via a bolt in a state where thin and semi-conical maintaining portions formed on inner inclination surfaces of abutment teeth of both sides with a small preparation are accurately engaged with keys formed on inner inclination surfaces of the keeper and the body in correspondence to the maintaining portions.

3 Claims, 47 Drawing Sheets

[Figure 1]
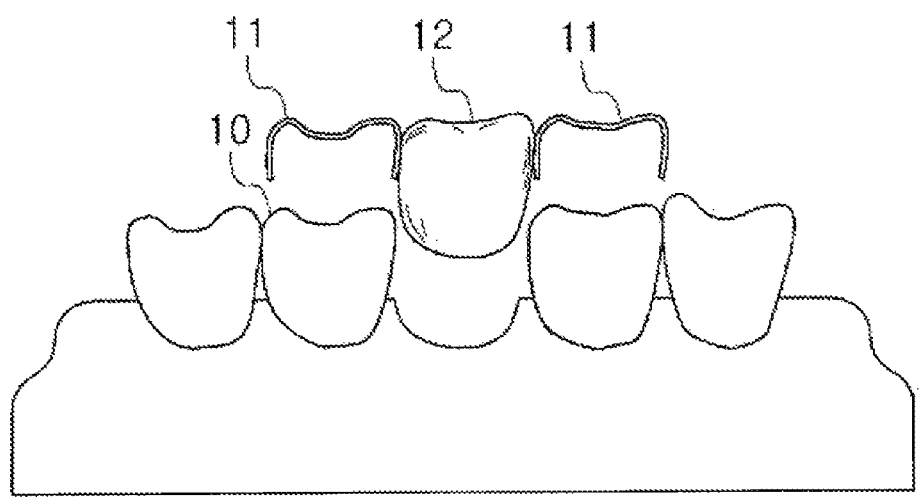
(Prior Art)

[Figure 2]
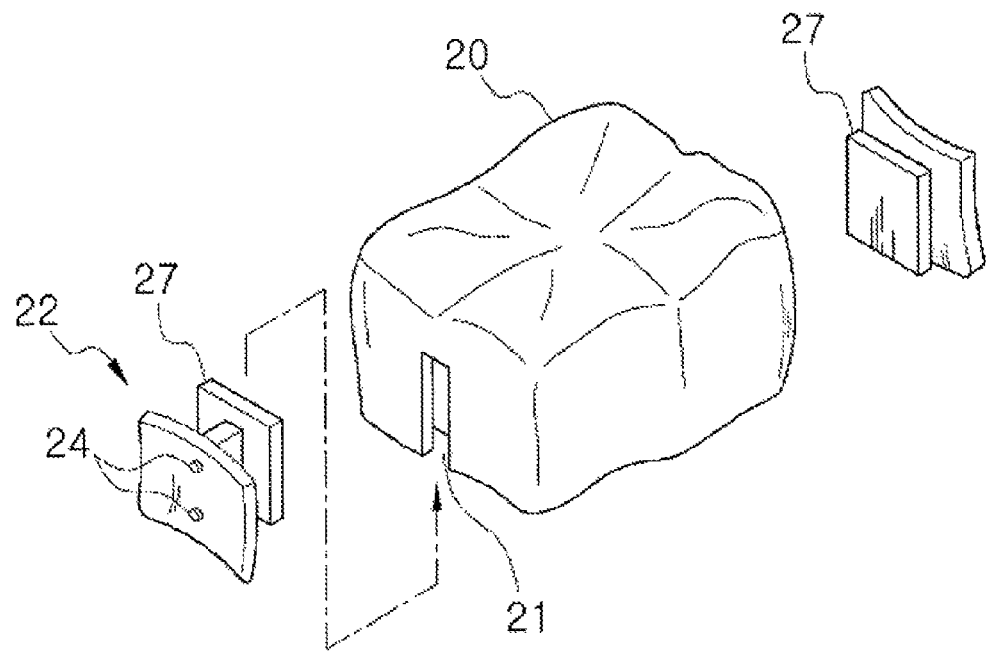
(Prior Art)

[Figure 3]
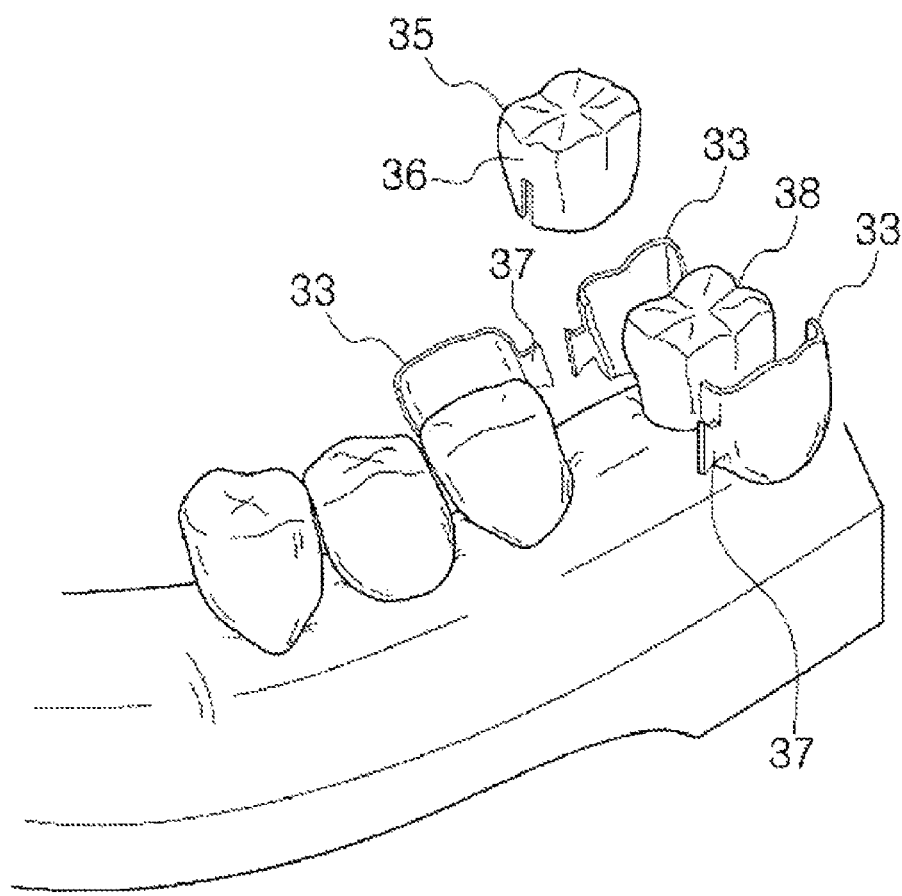
(Prior Art)

[Figure 4]
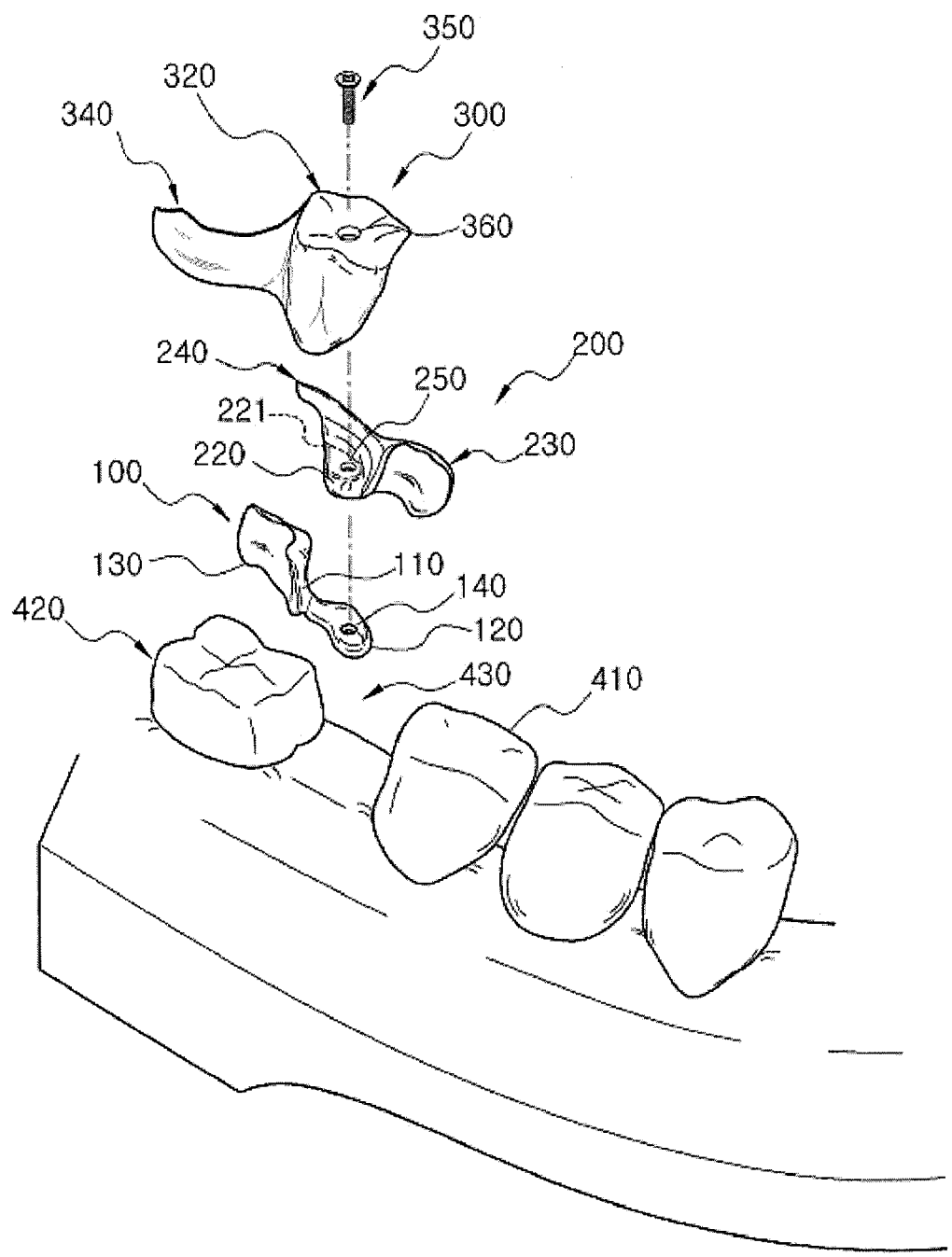

[Figure 5]
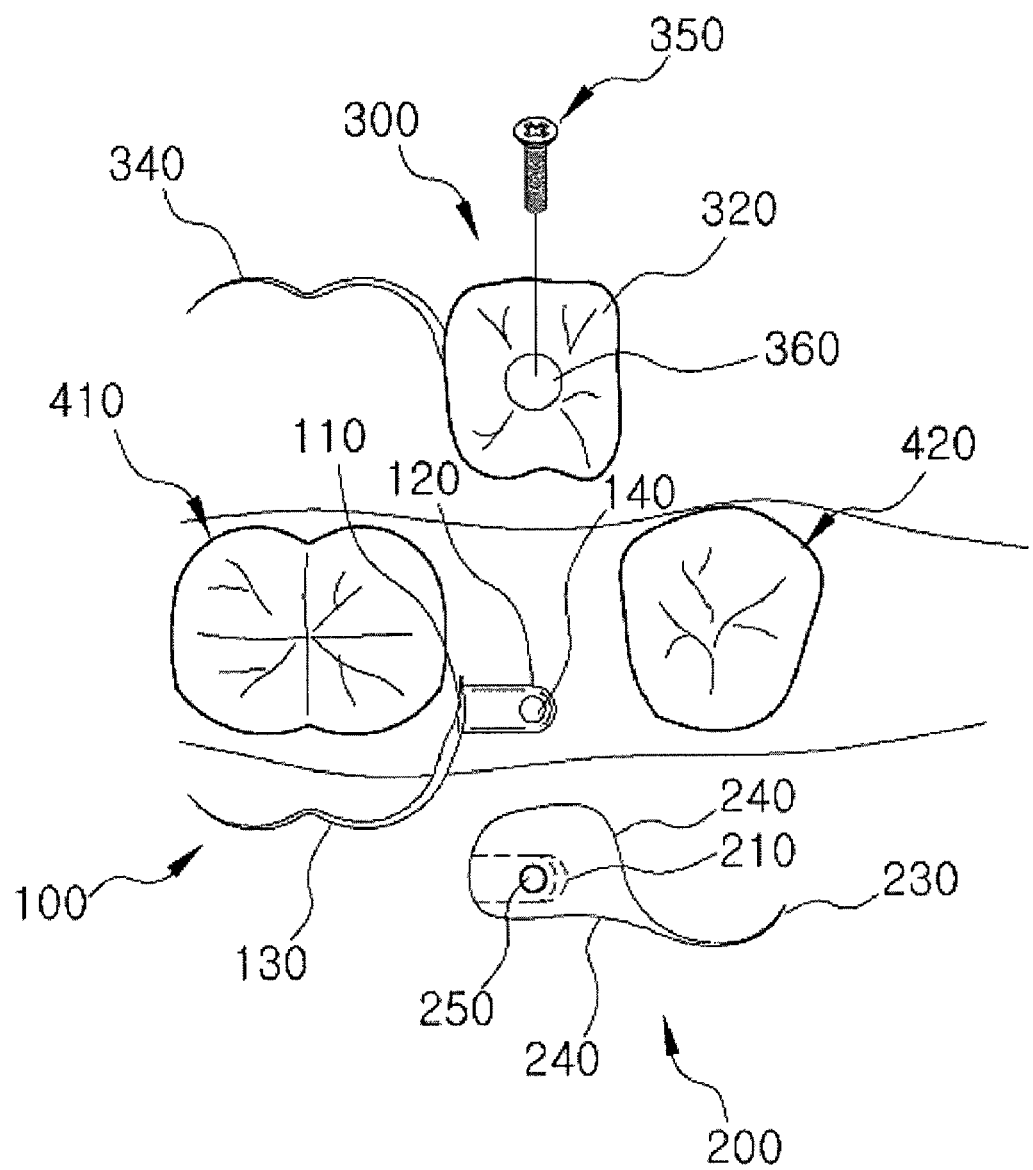

[Figure 6]
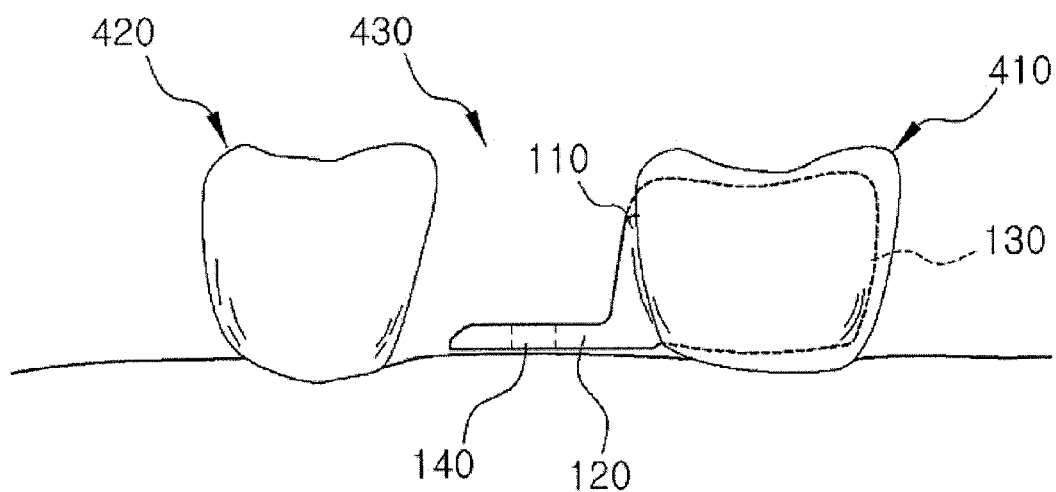

[Figure 7]
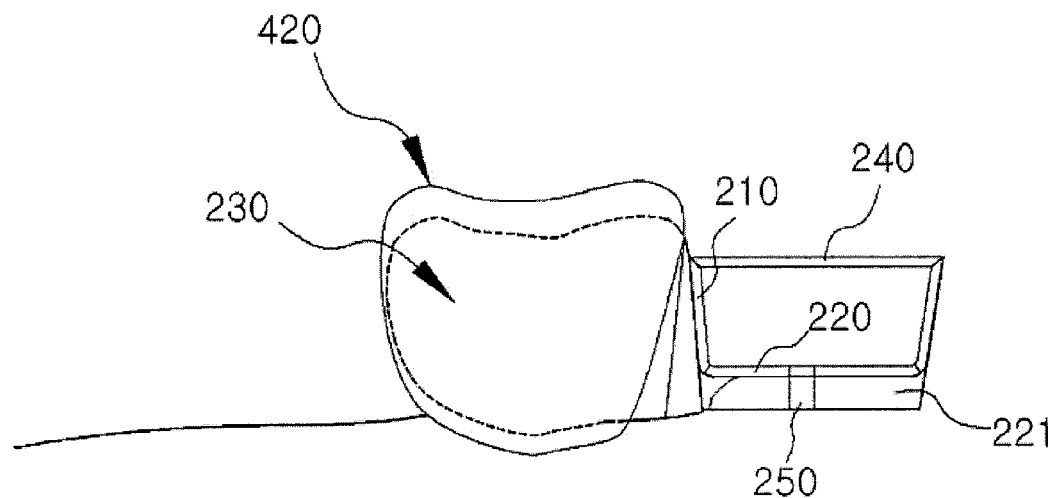
[Figure 8]
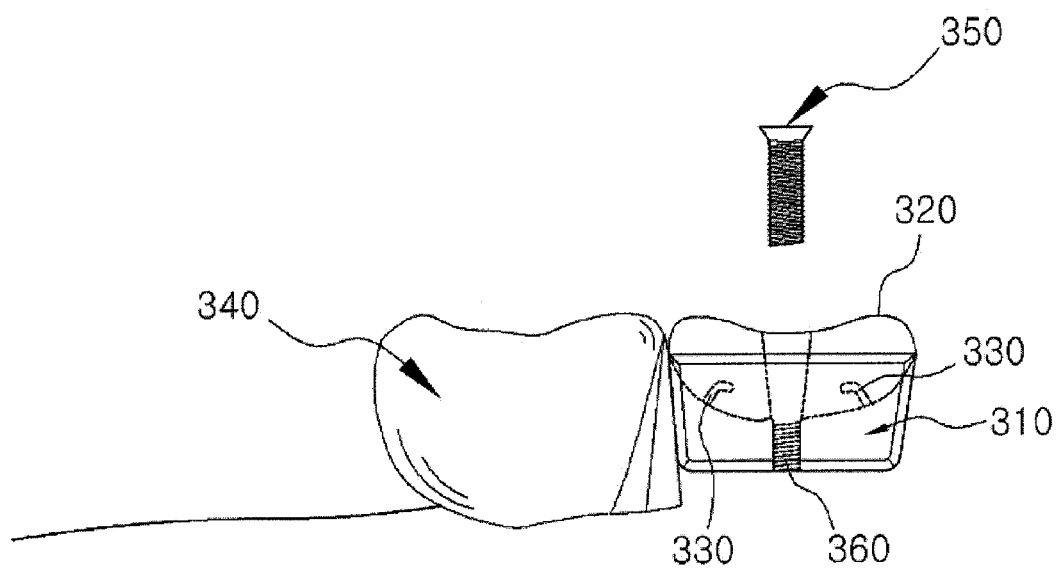

[Figure 9]
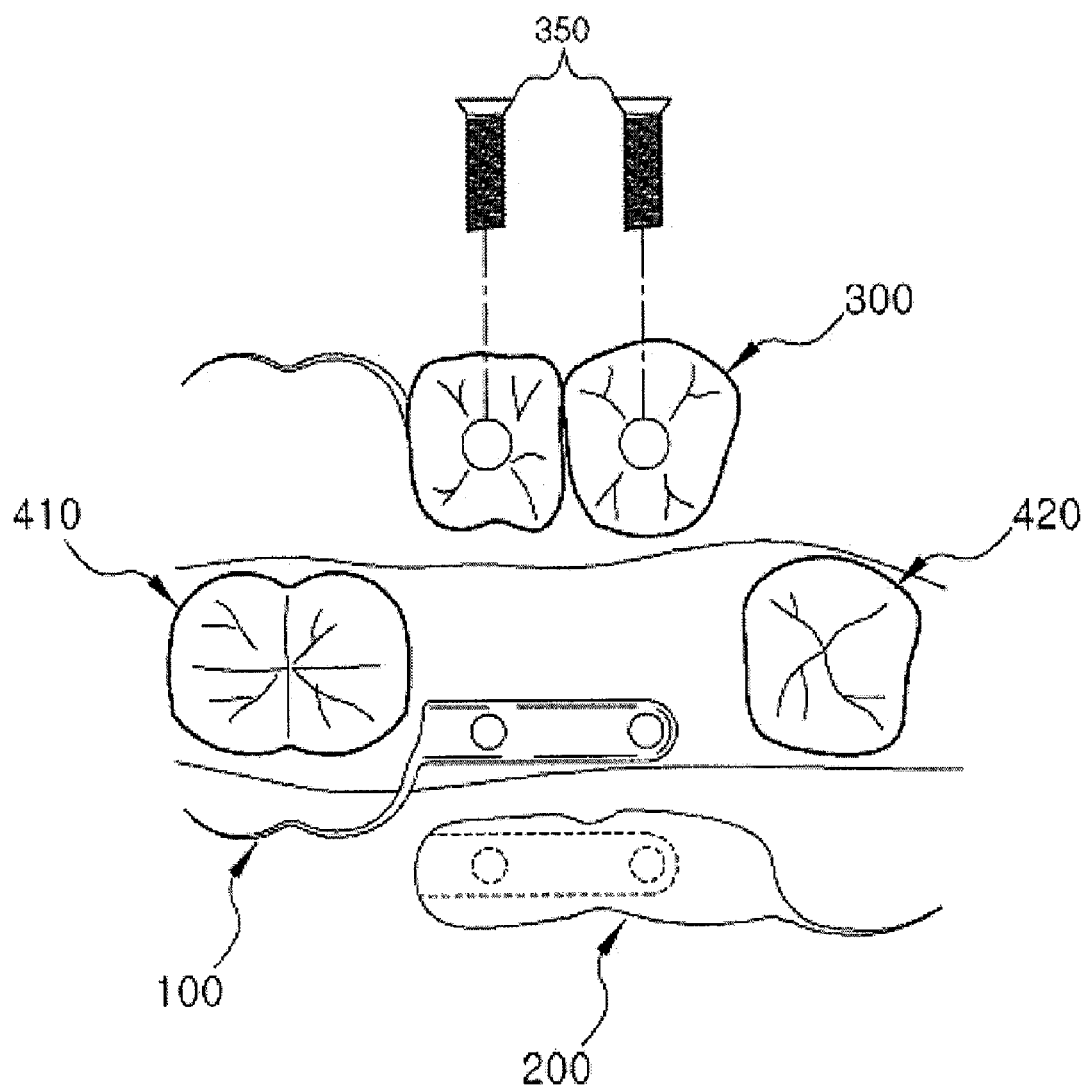

[Figure 10]
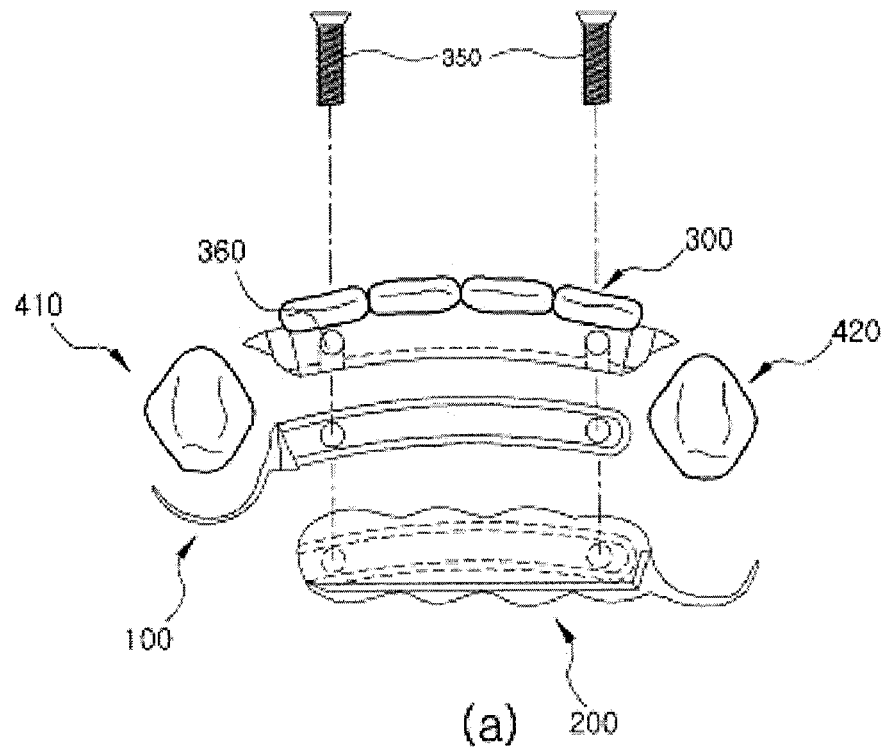
(a)
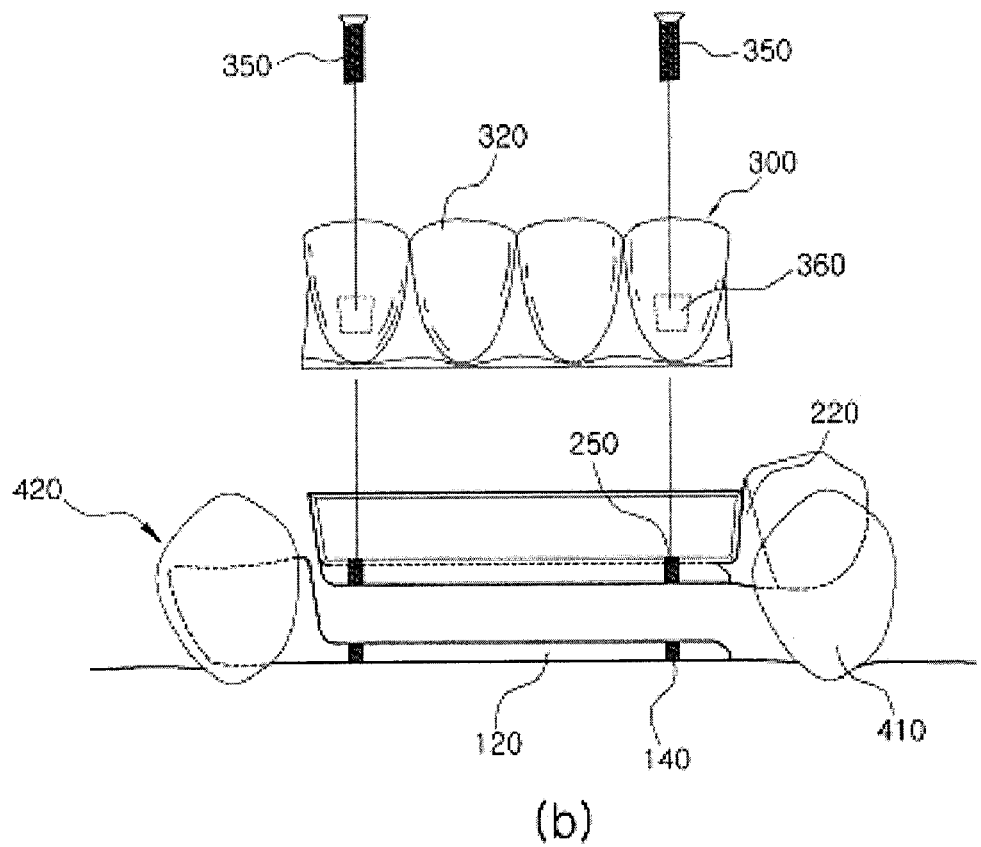
(b)

[Figure 11]
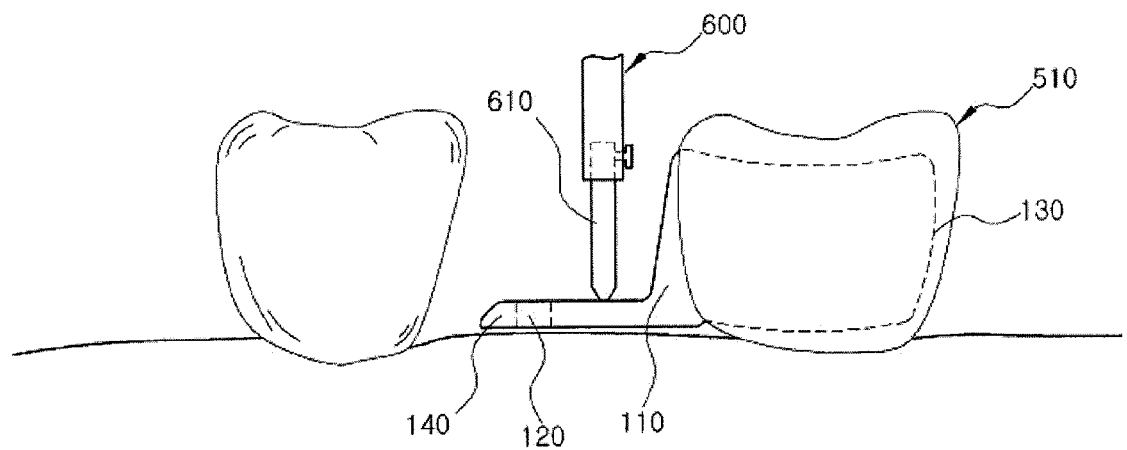

[Figure 12]
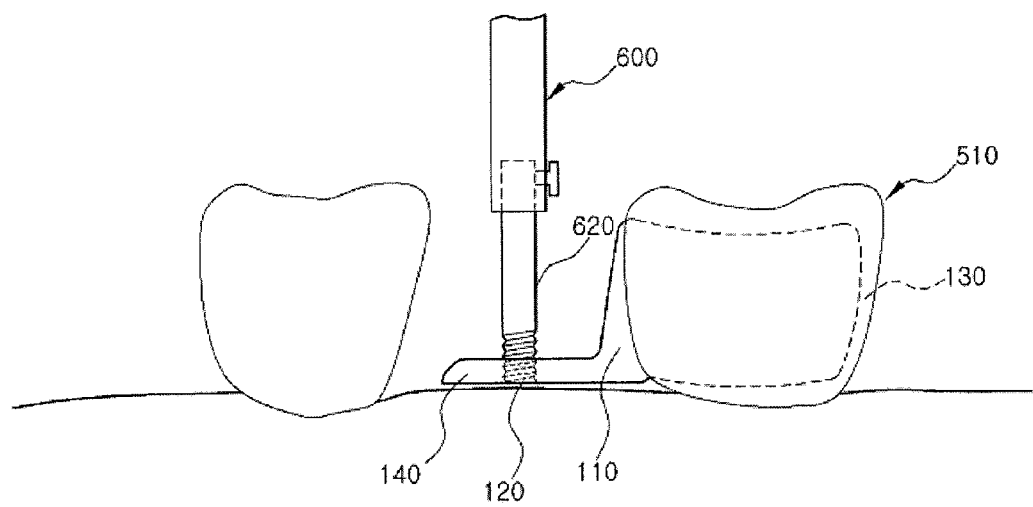

【Figure 13】
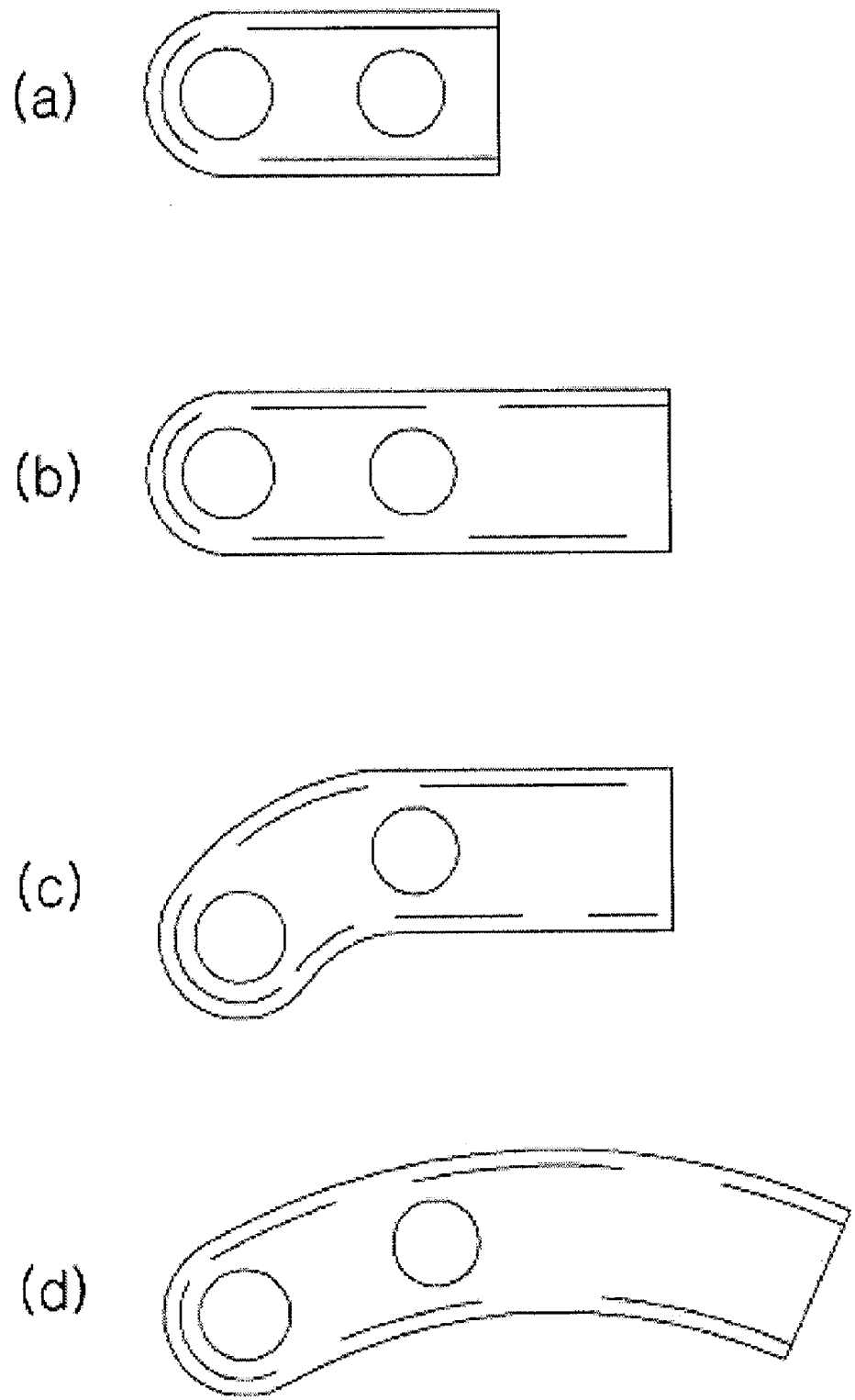

[Figure 14]
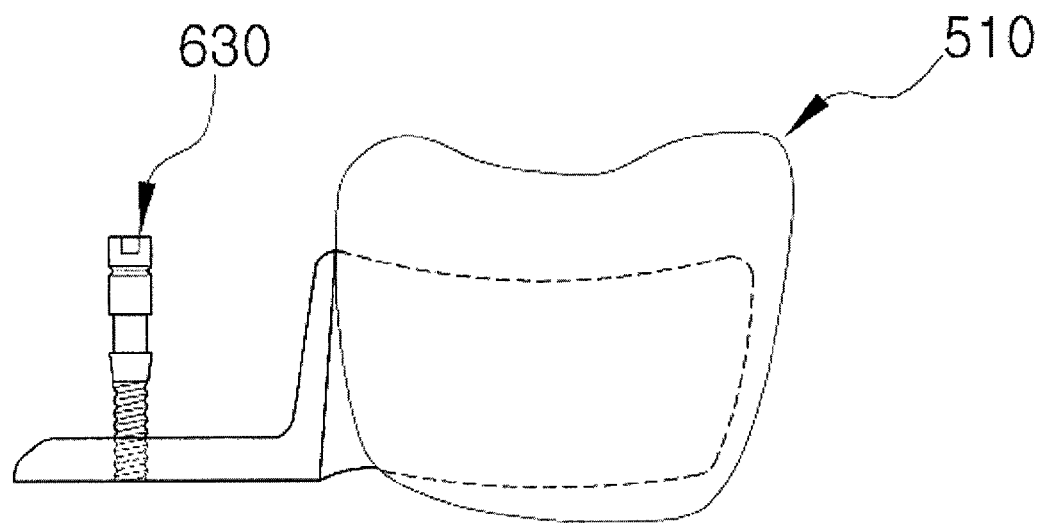

[Figure 15]
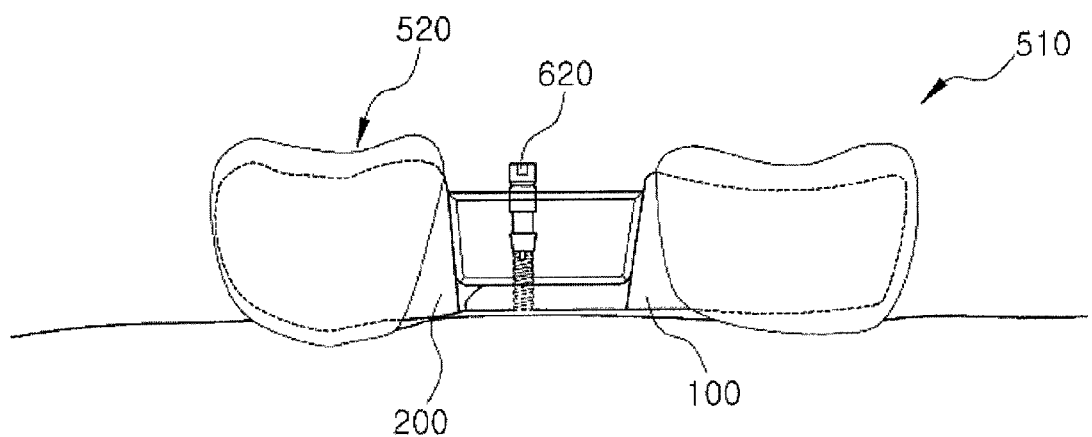

[Figure 16]
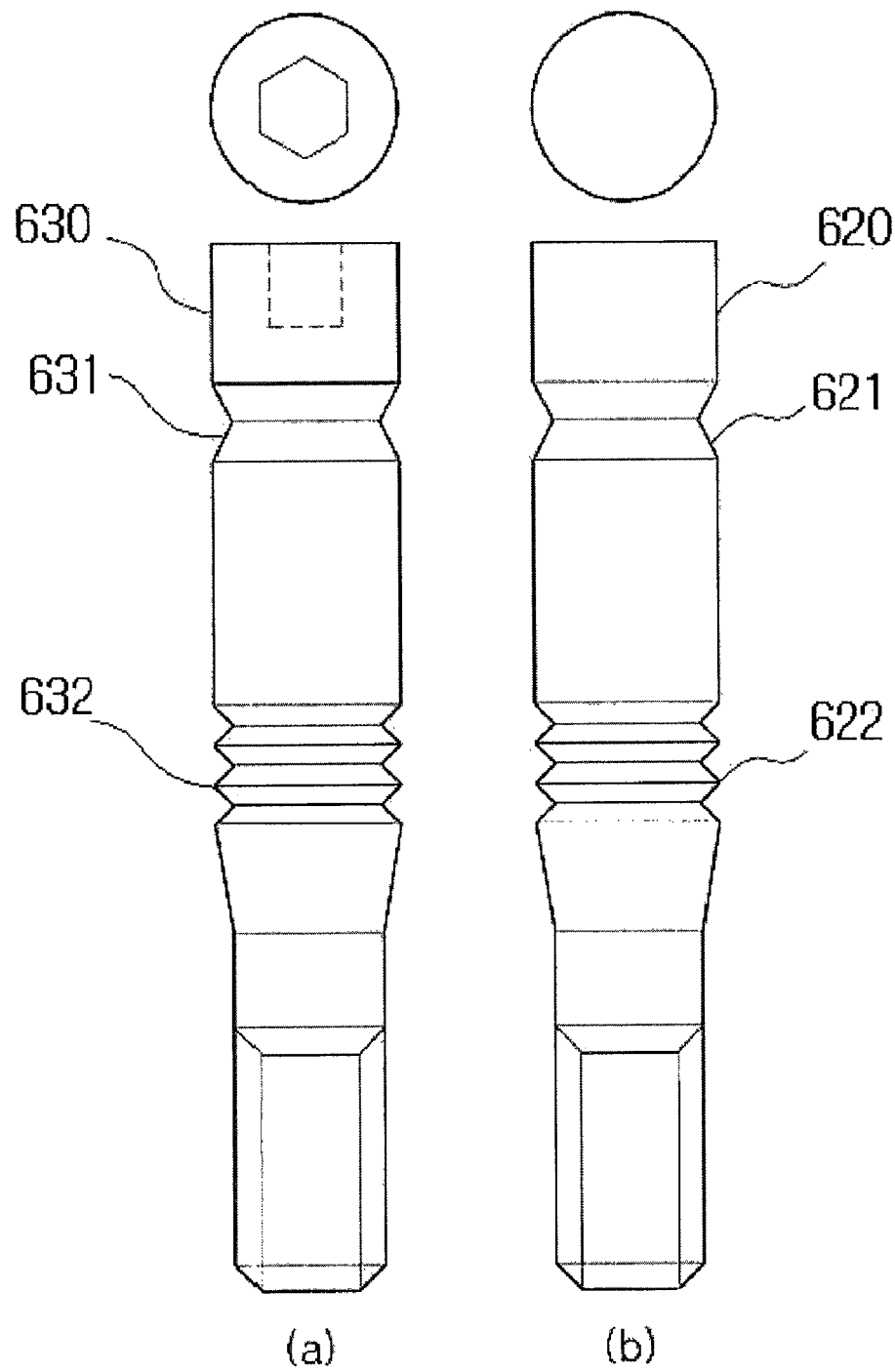
(a)　　　(b)

[Figure 17]
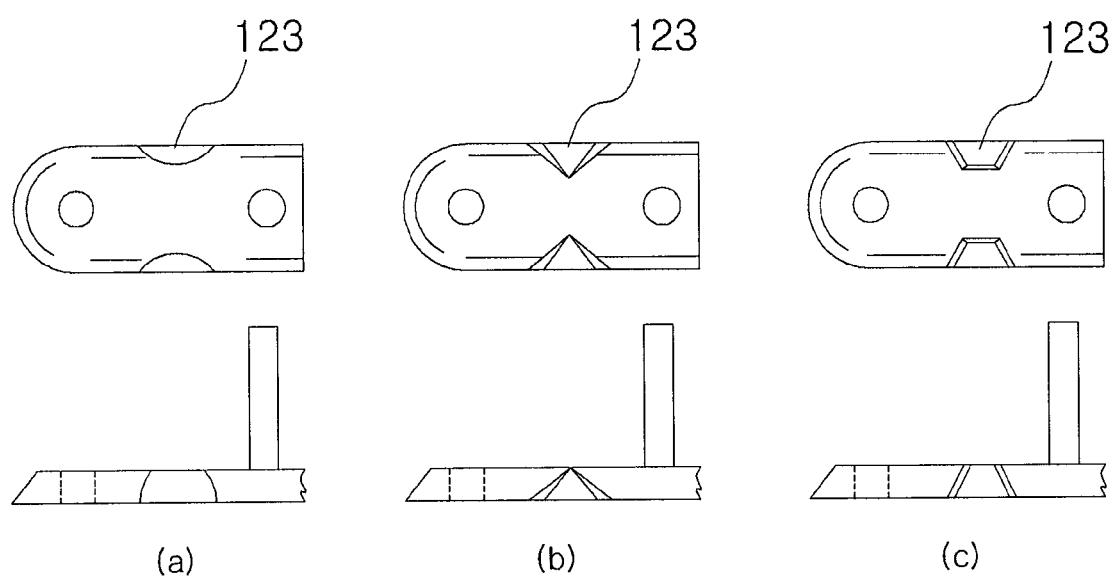
(a)　　　　　　　　(b)　　　　　　　　(c)

[Figure 18]
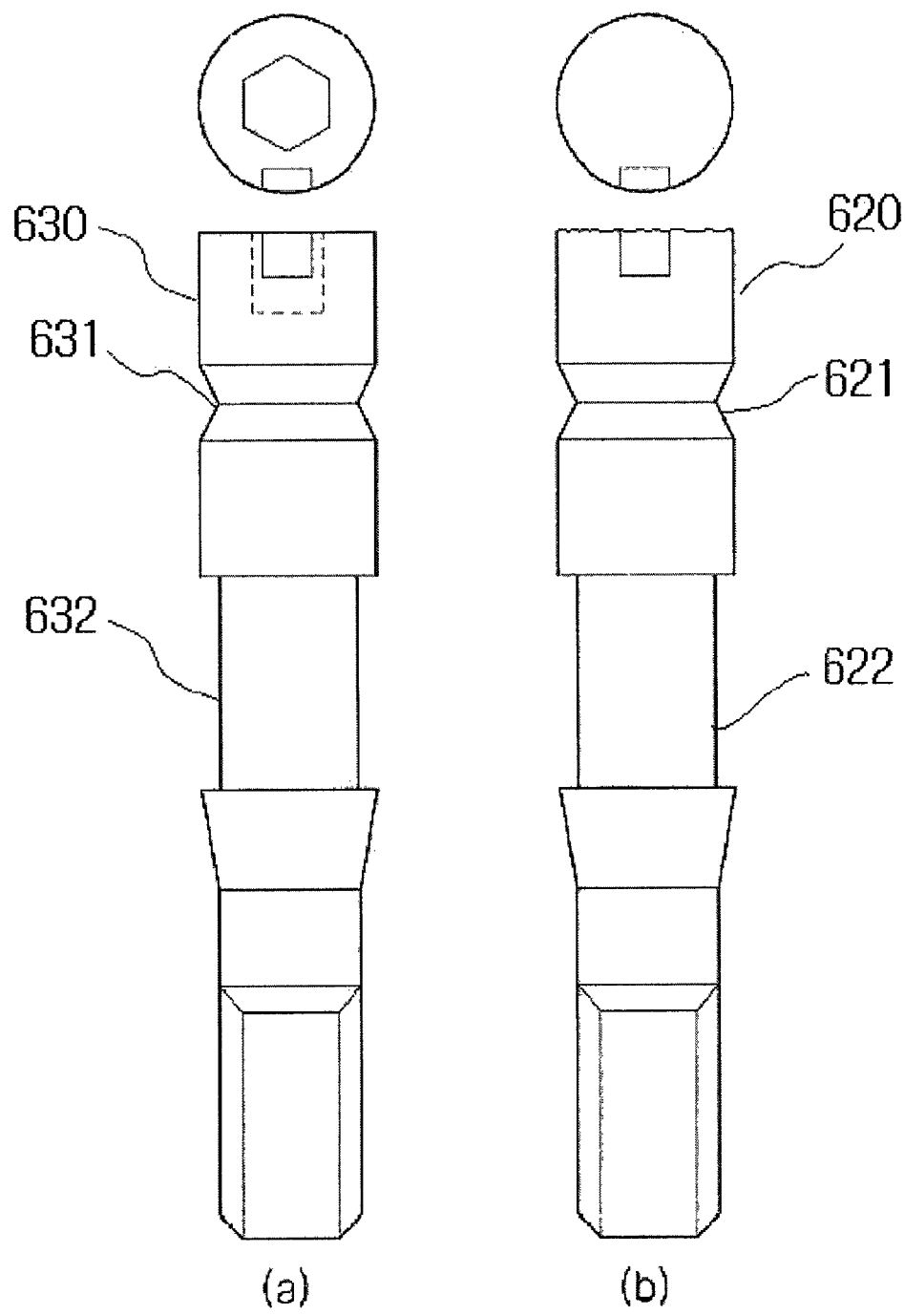
(a)  (b)

【Figure 19】
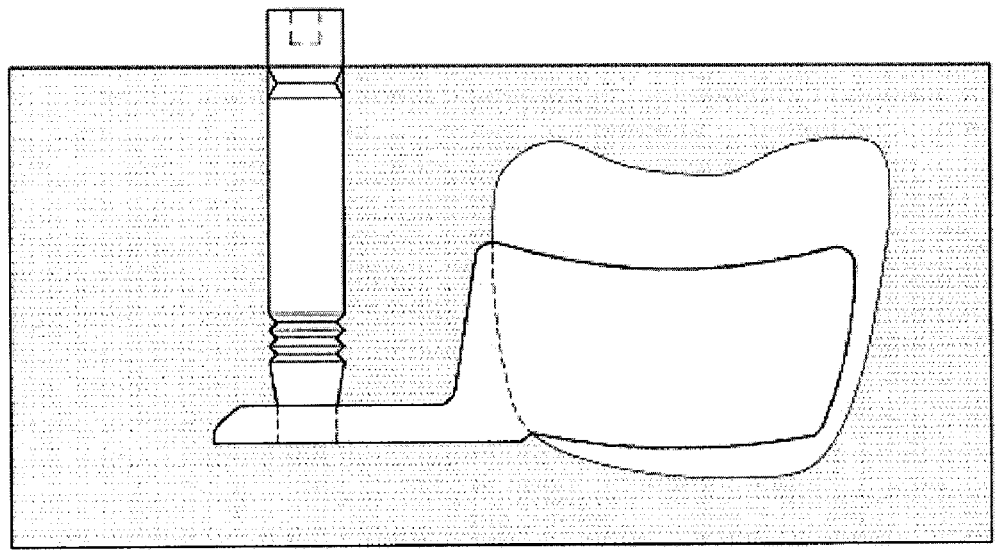
(a)
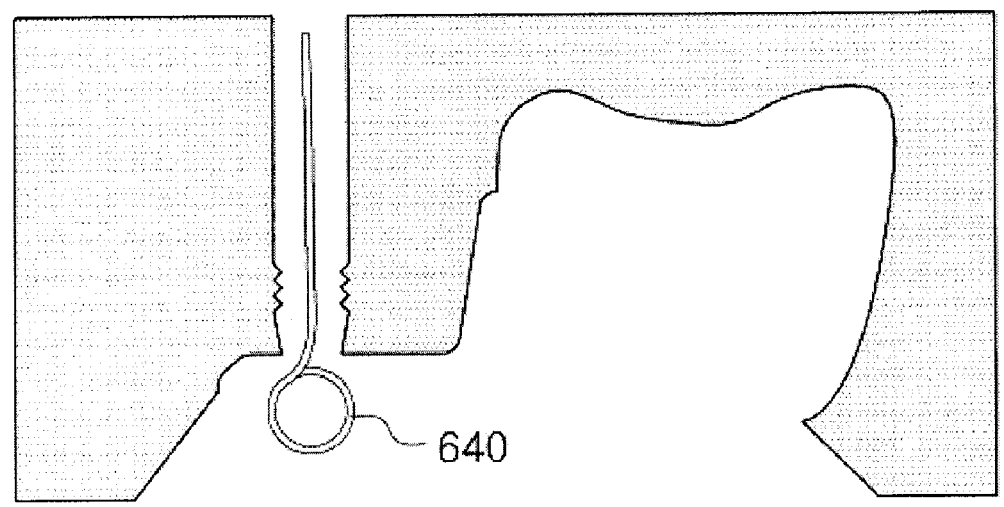
(b)

[Figure 20]
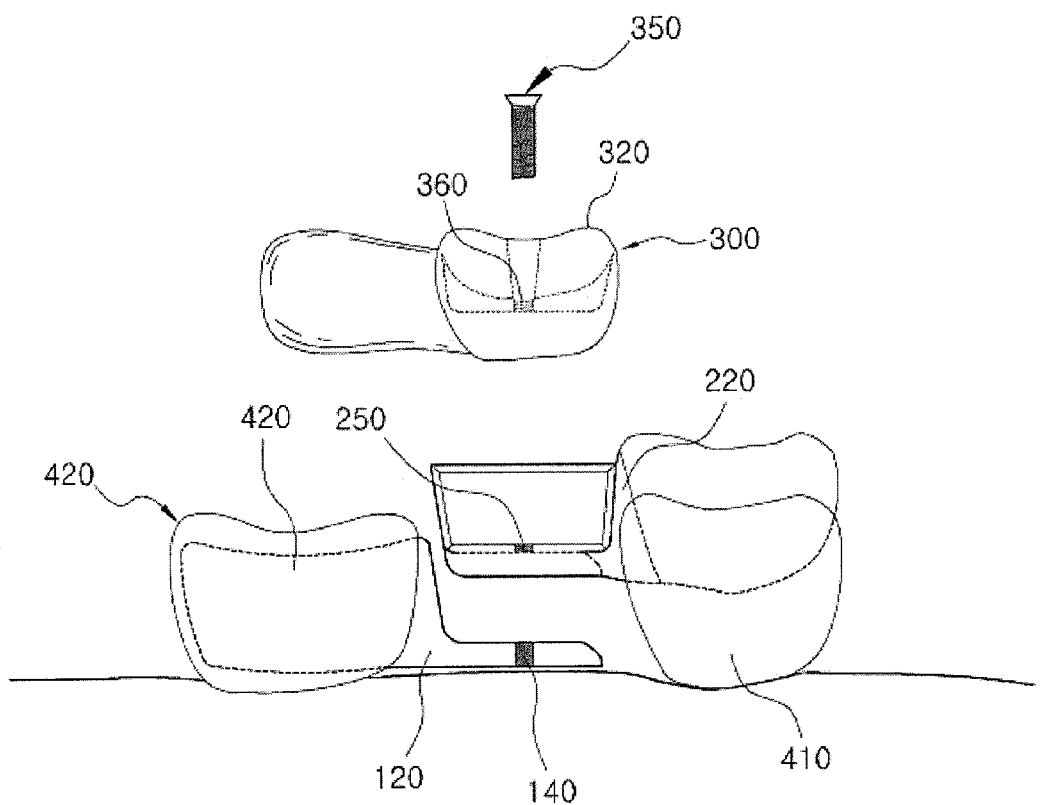

[Figure 21]
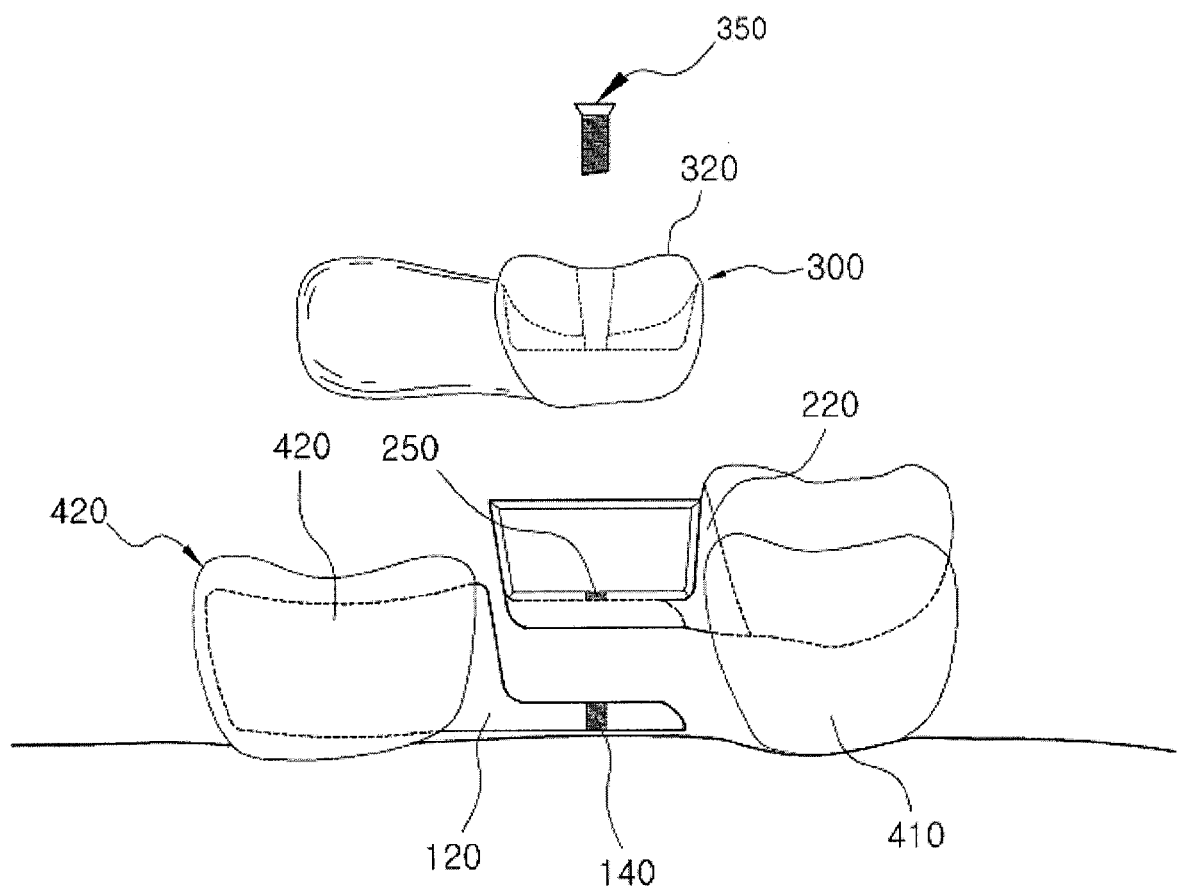

[Figure 22]
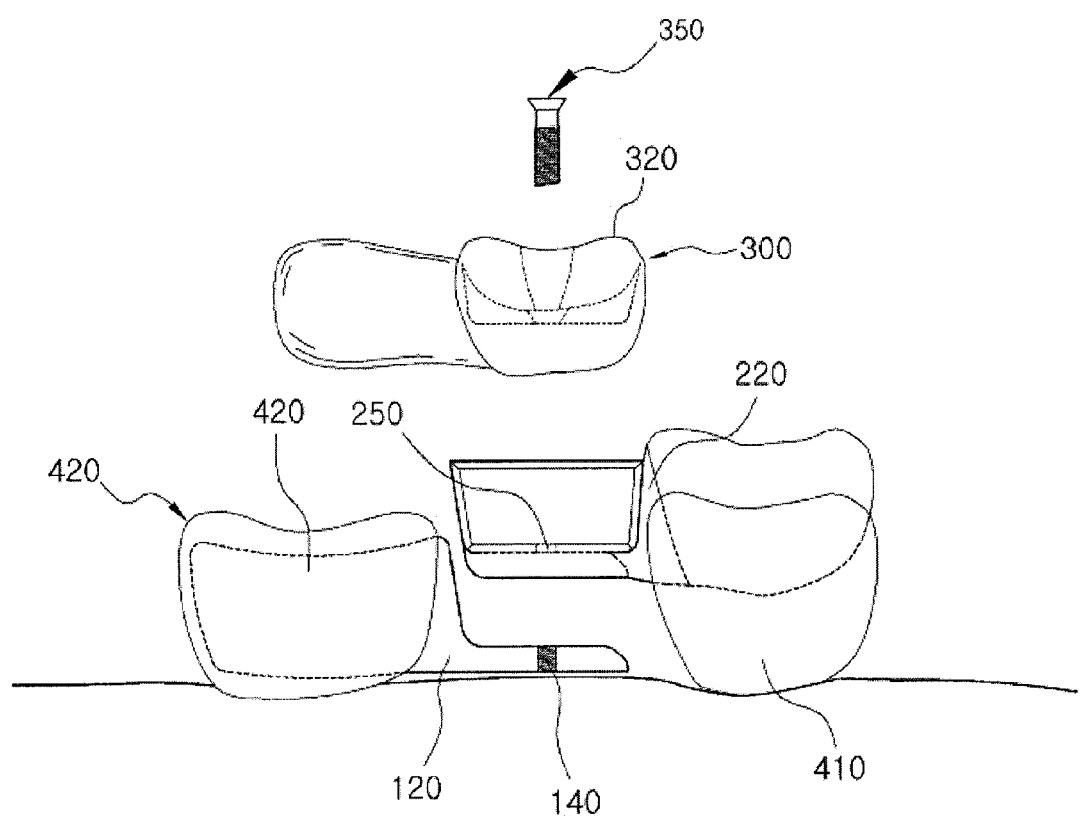

【Figure 23】
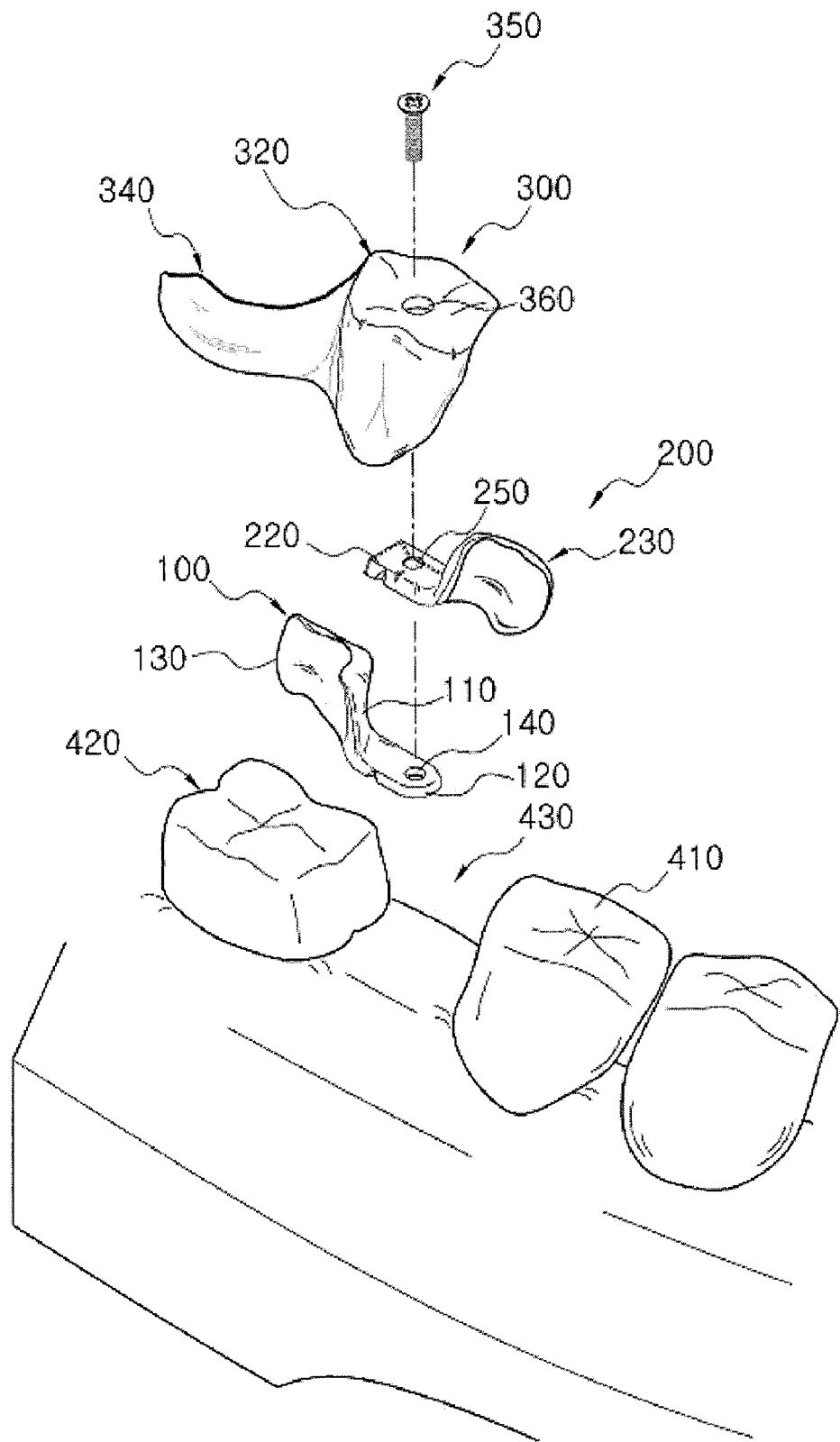

[Figure 24]
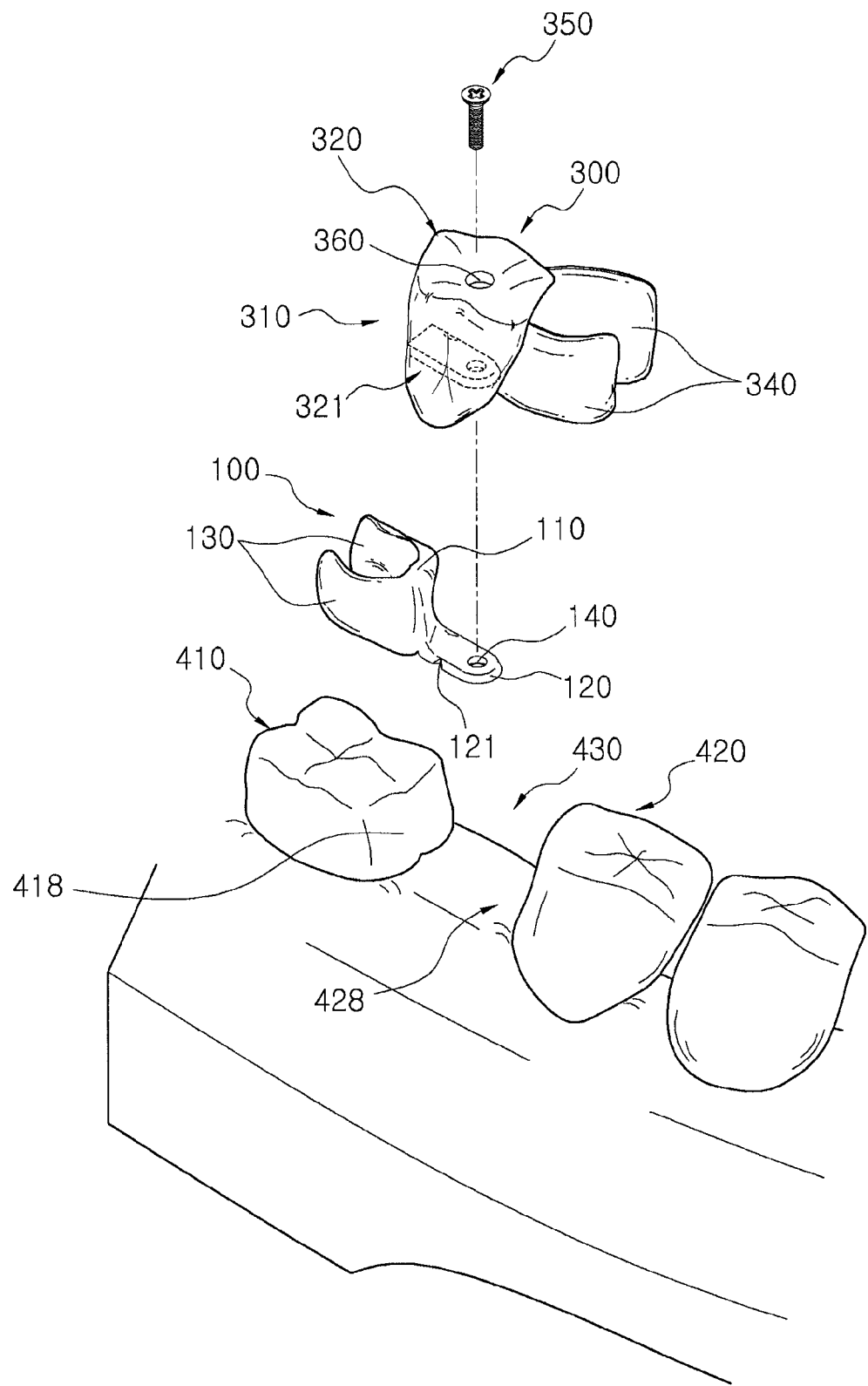

【Figure 25】
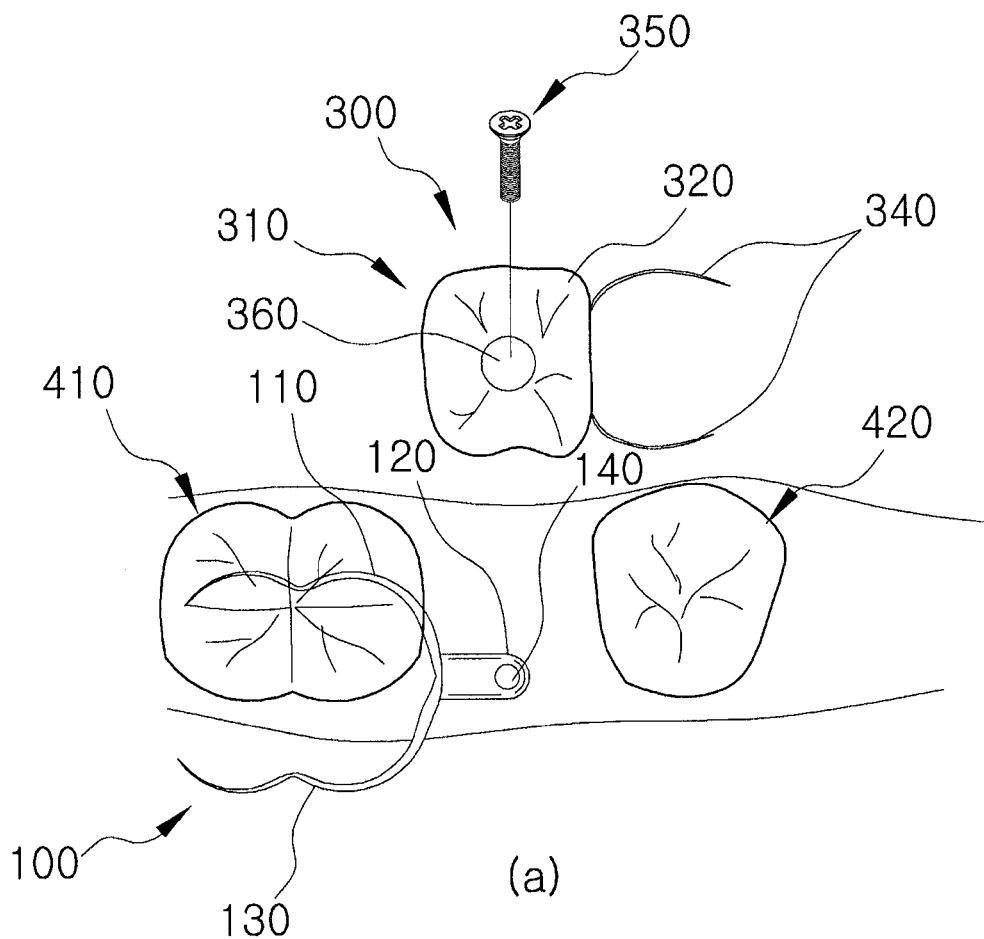
(a)
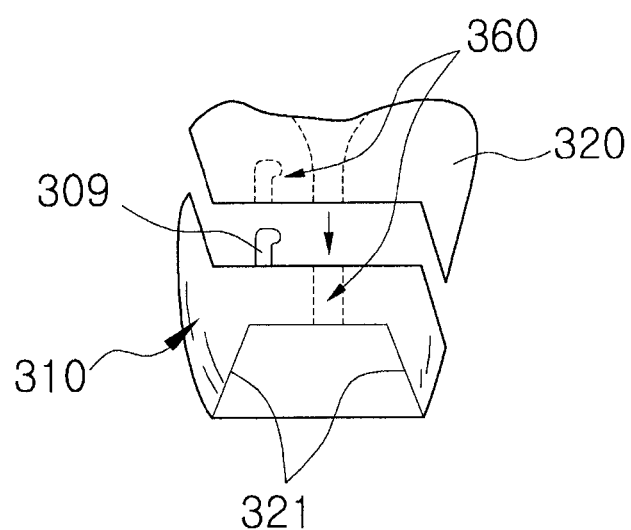
(b)

[Figure 26]
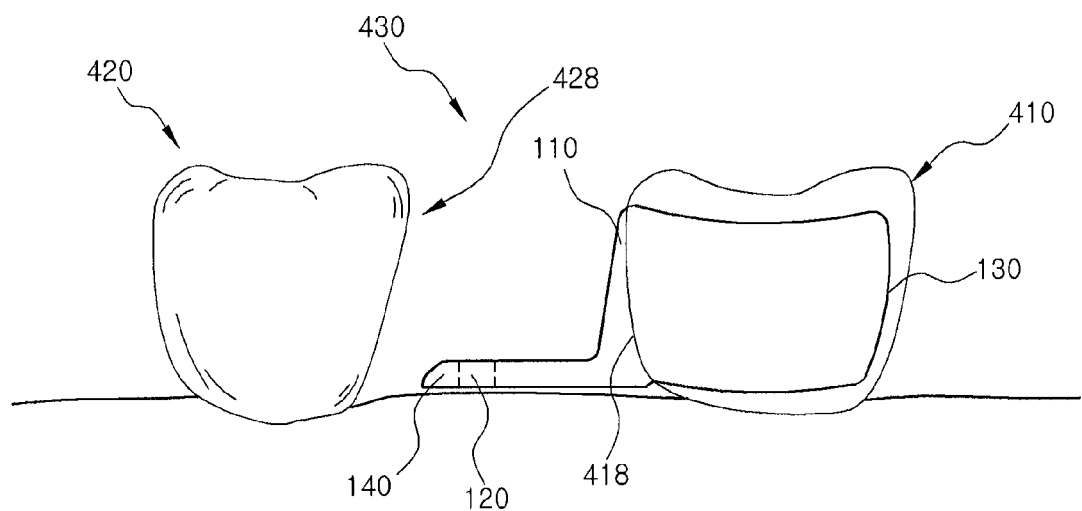

[Figure 27]
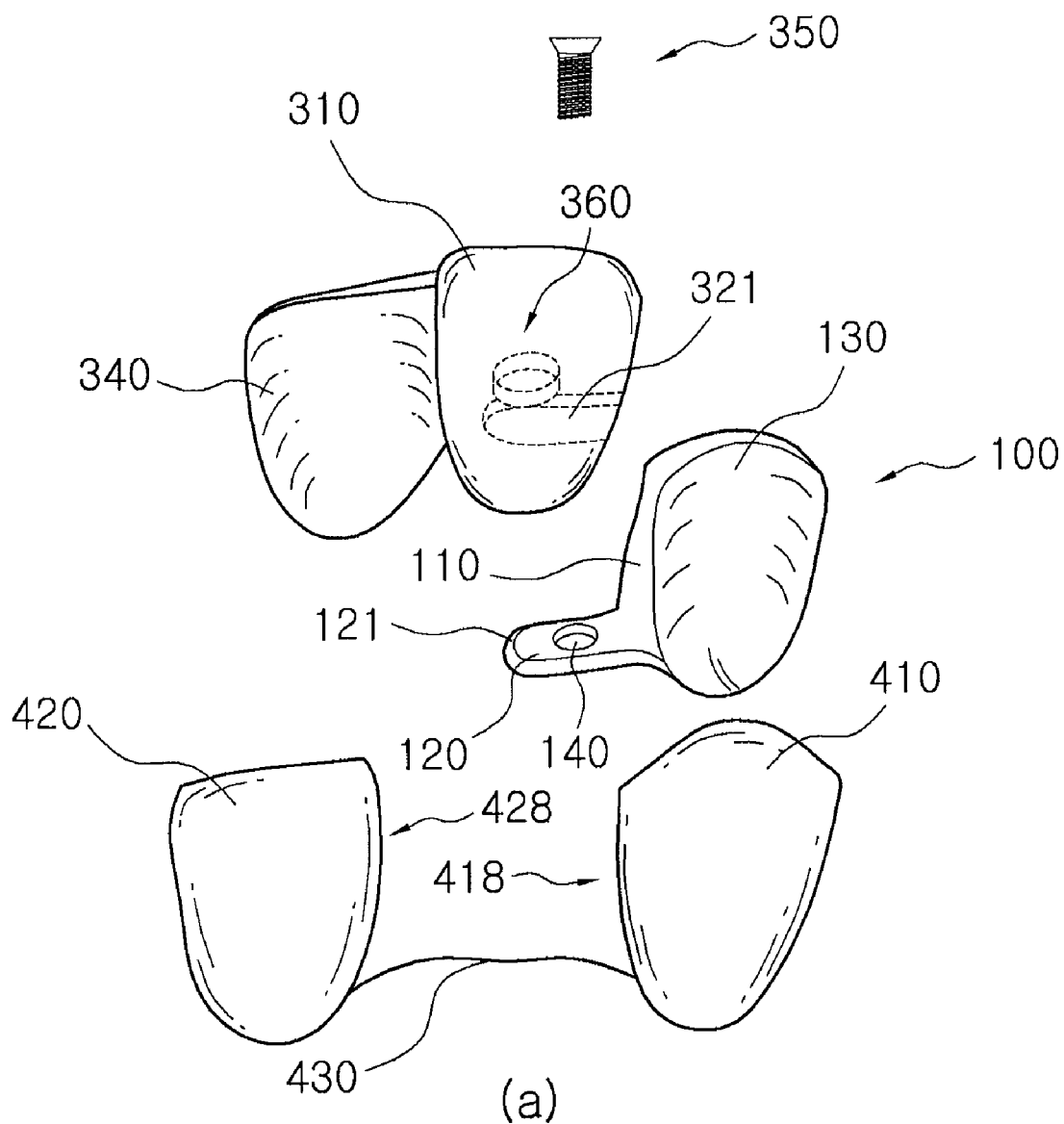
(a)
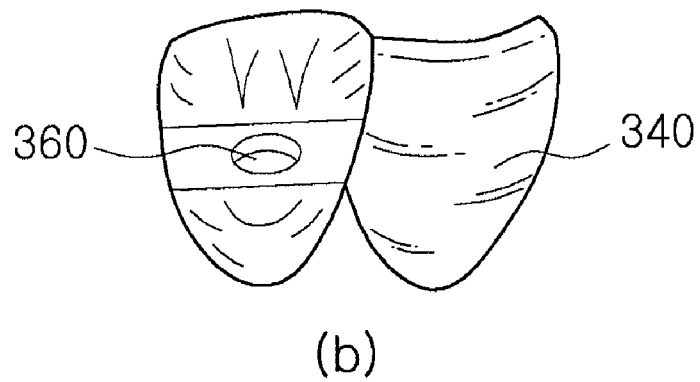
(b)

[Figure 28]
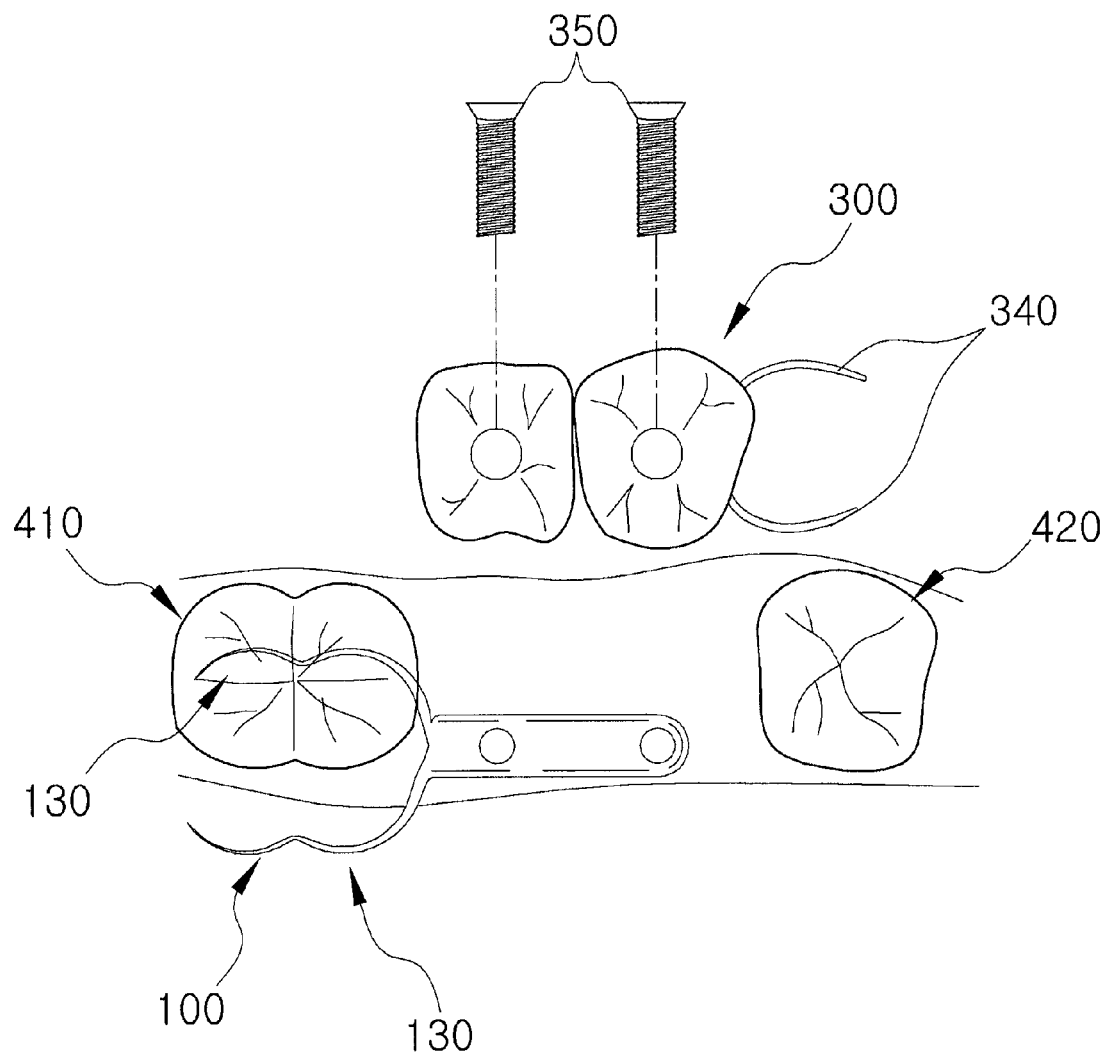

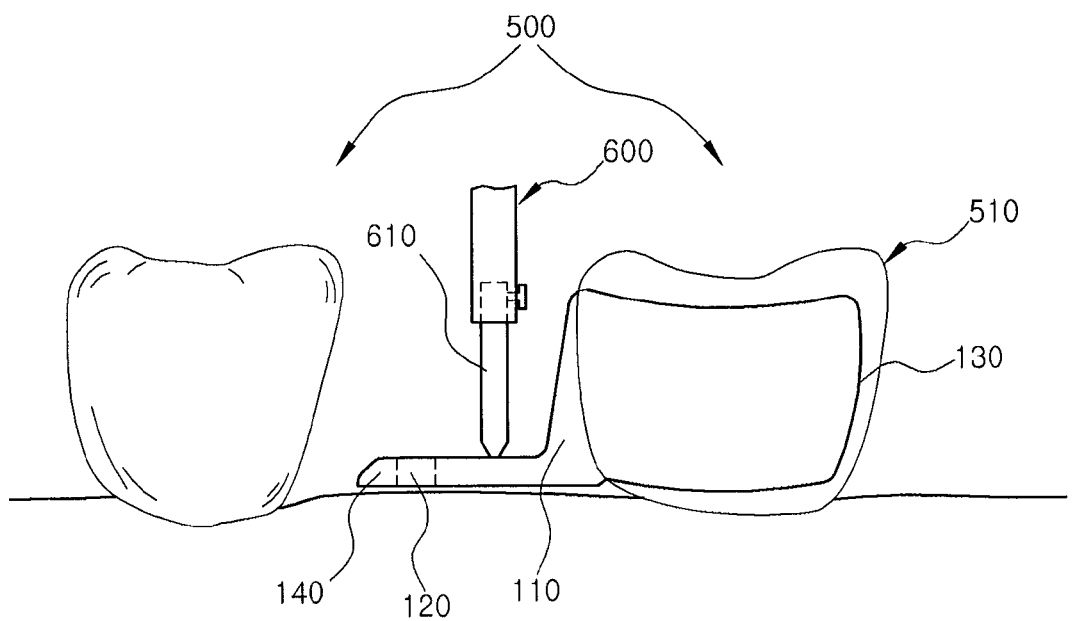
[Figure 29]

[Figure 30]
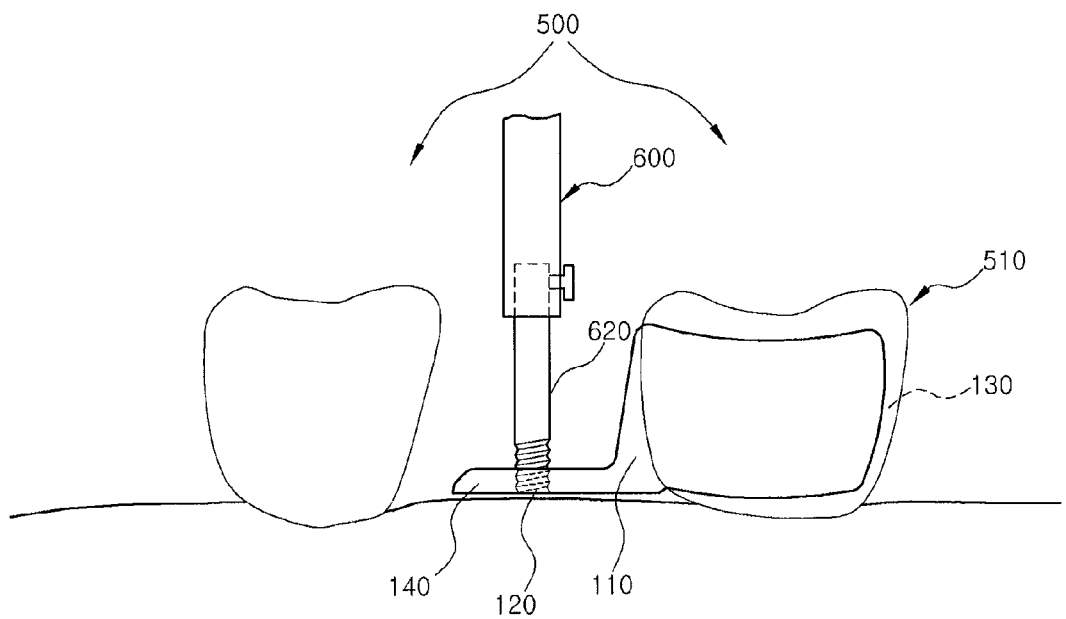

【Figure 31】
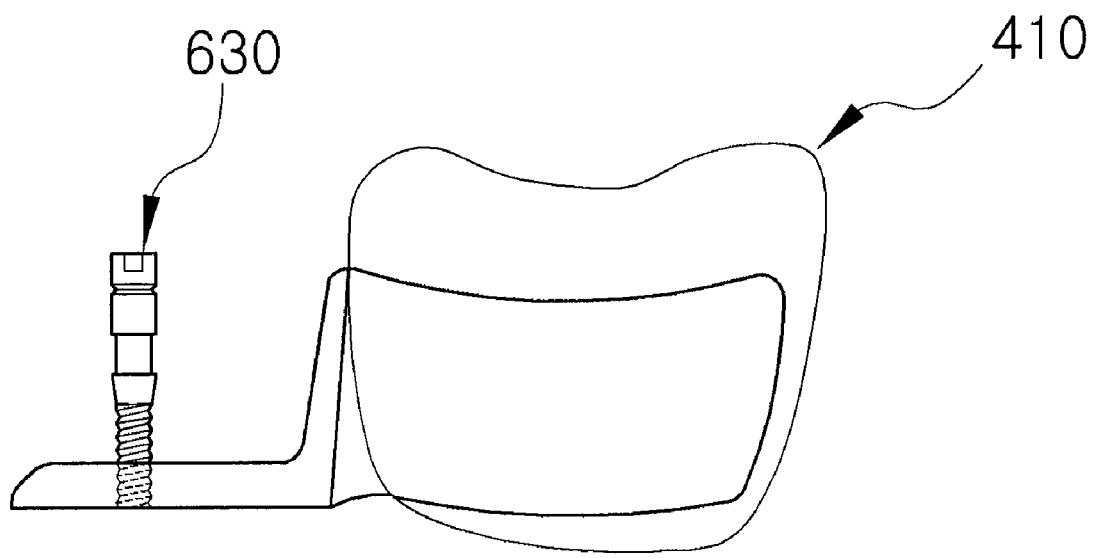

[Figure 32]
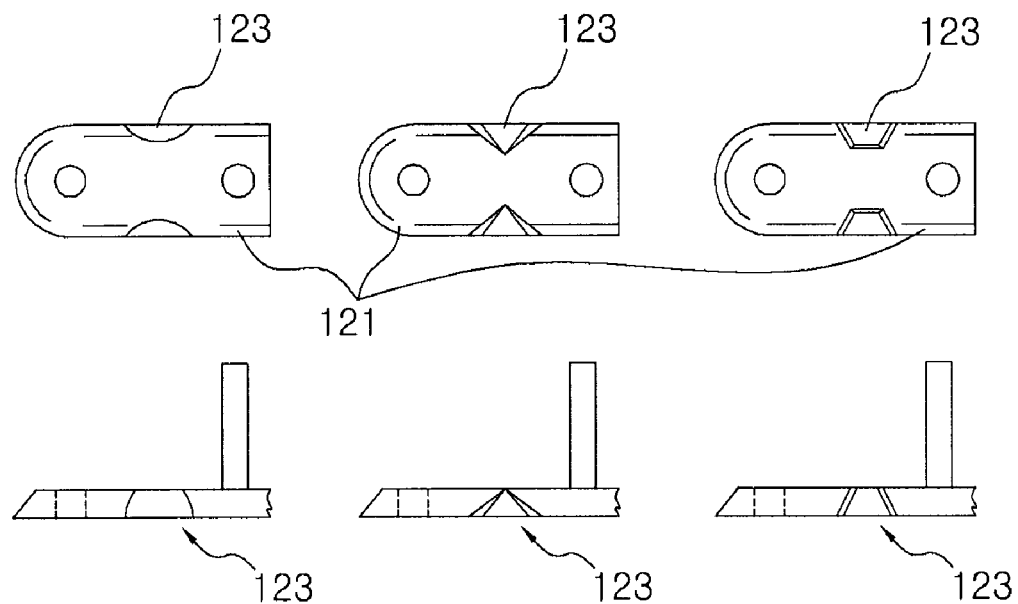
(a)
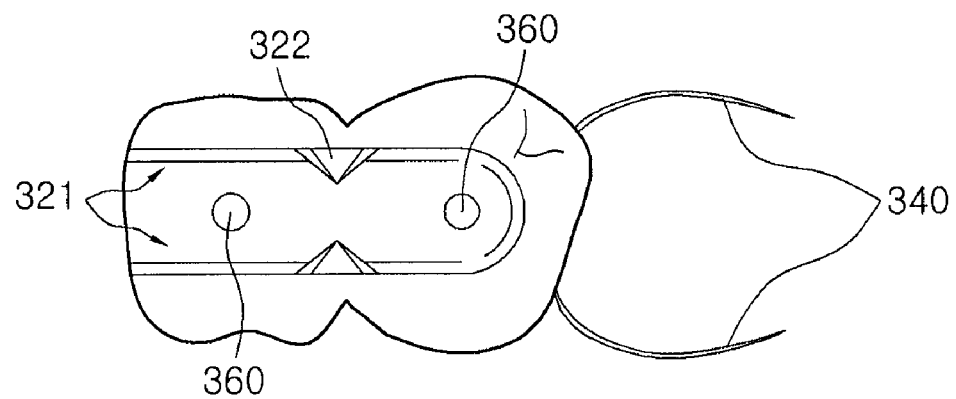
(b)

[Figure 33]
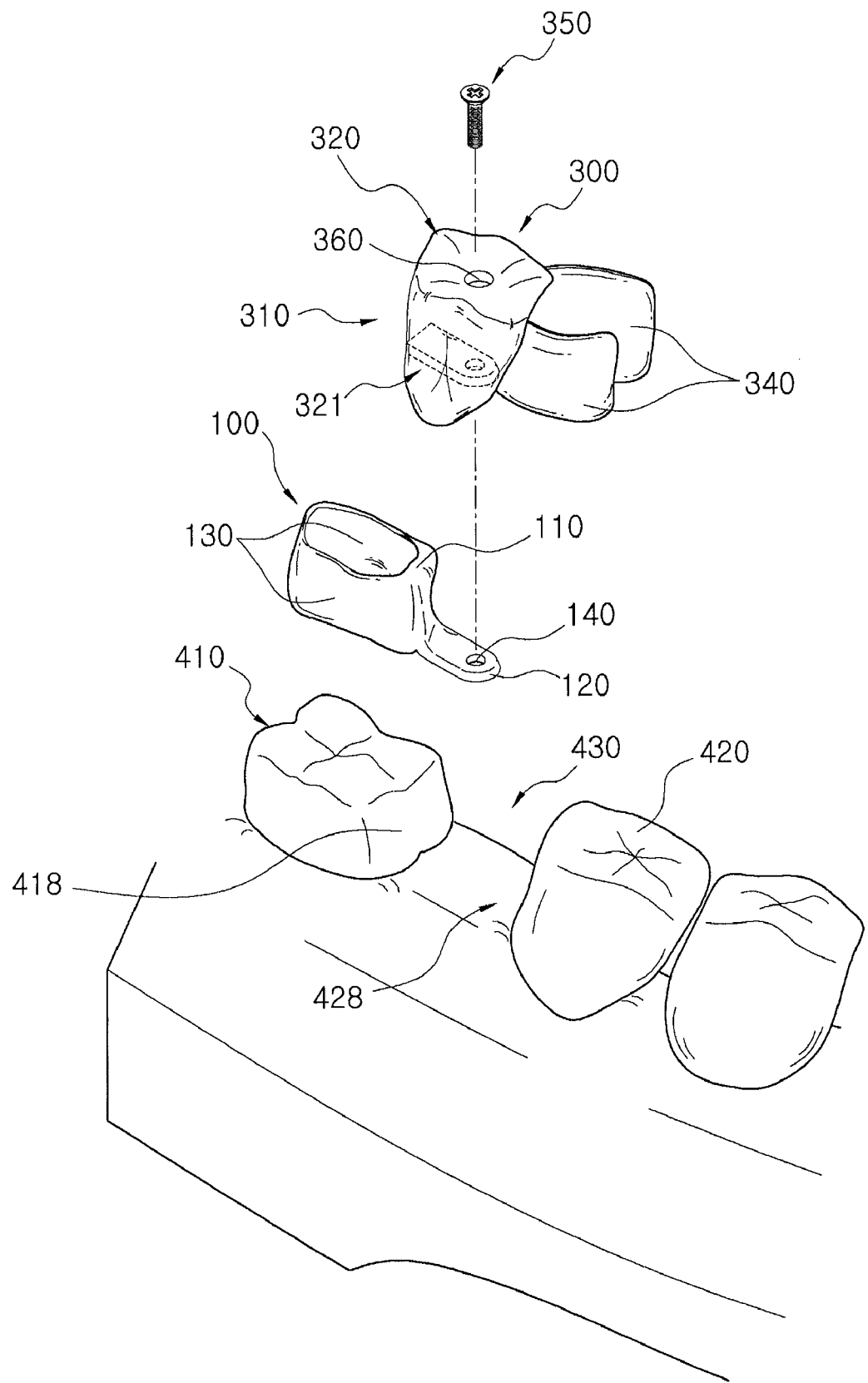

【Figure 34】
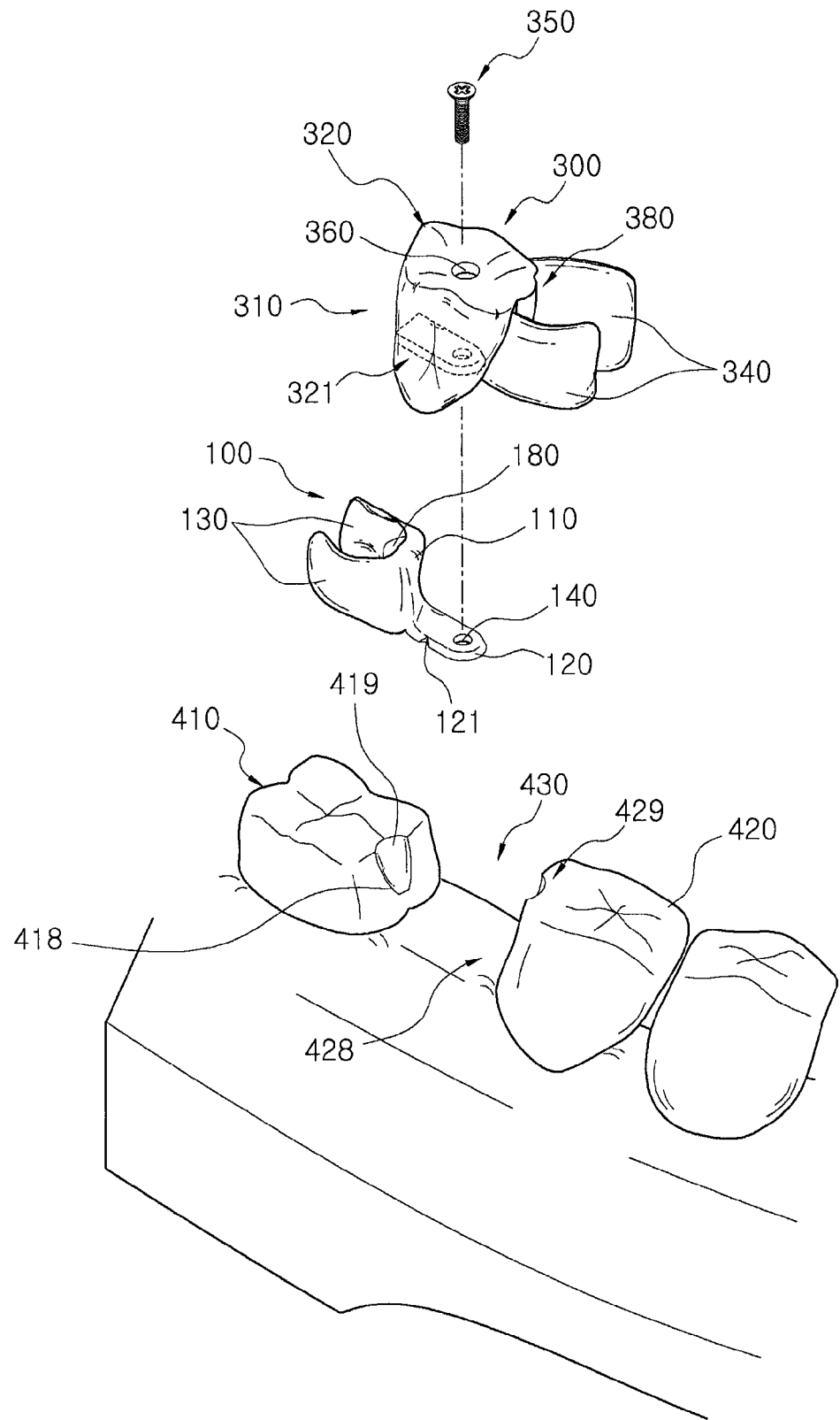

【Figure 35】
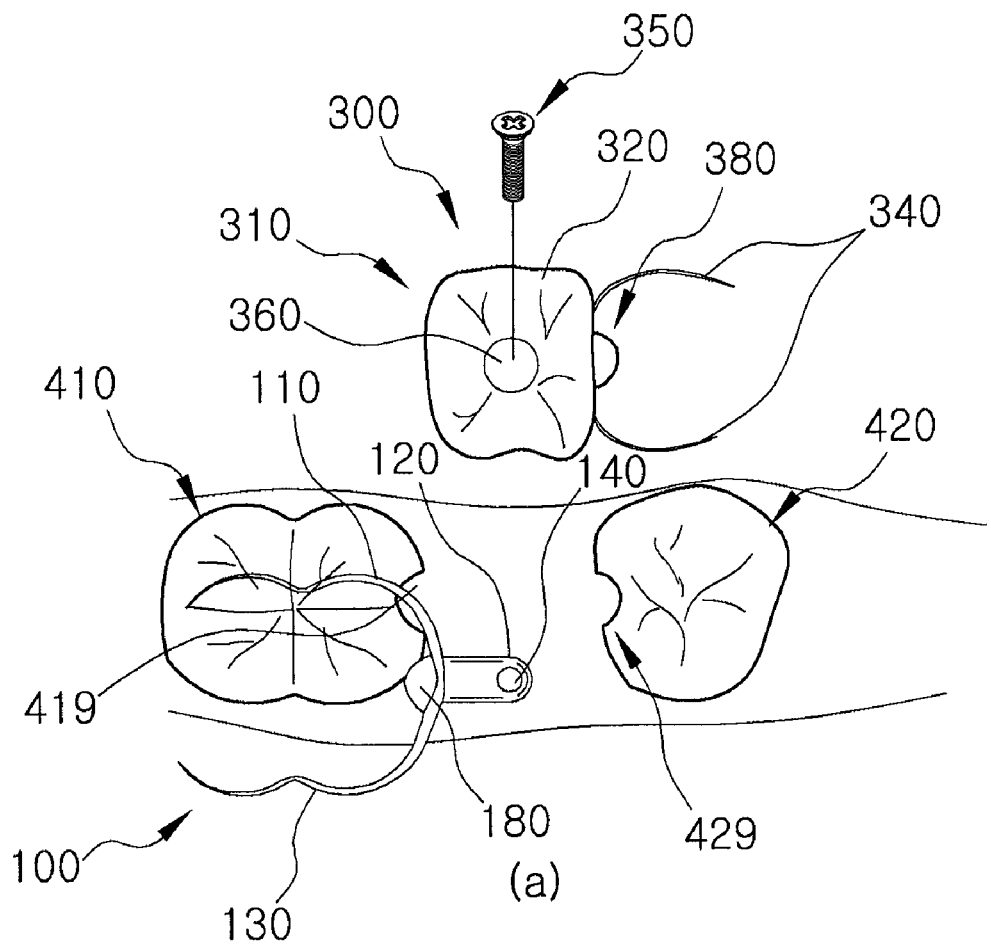
(a)
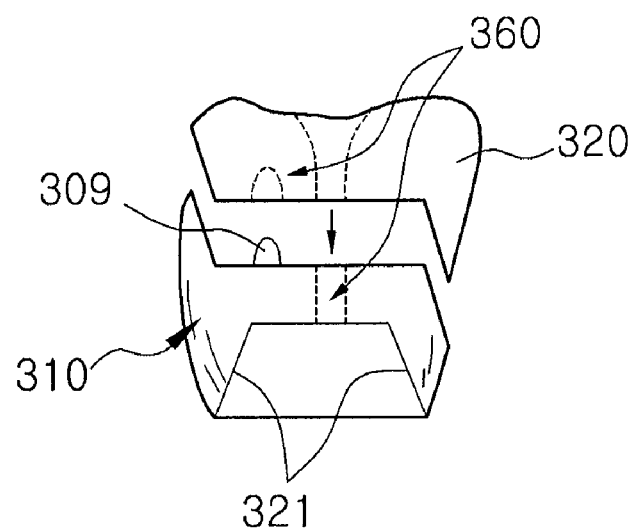
(b)

[Figure 36]
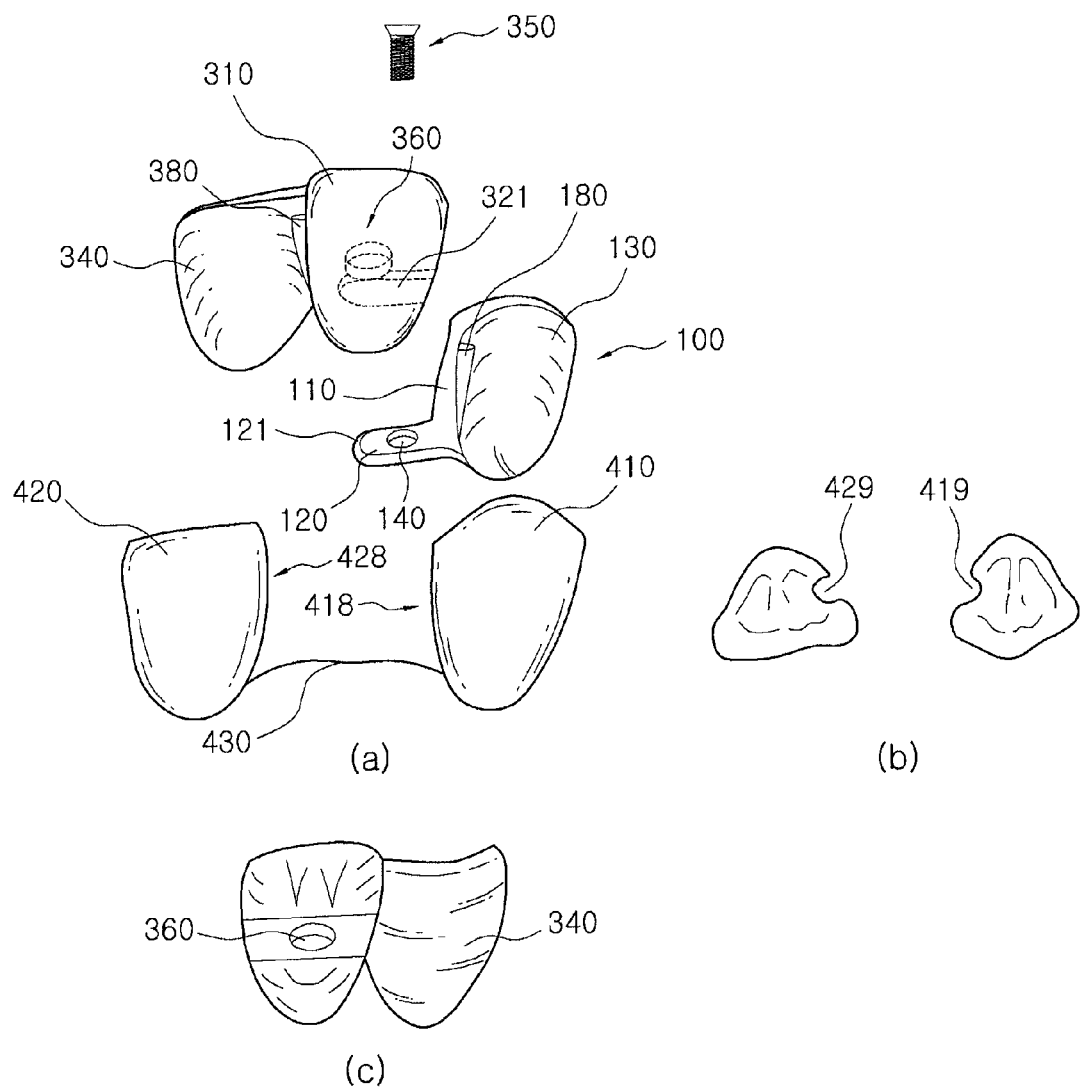
(a)
(b)
(c)

[Figure 37]
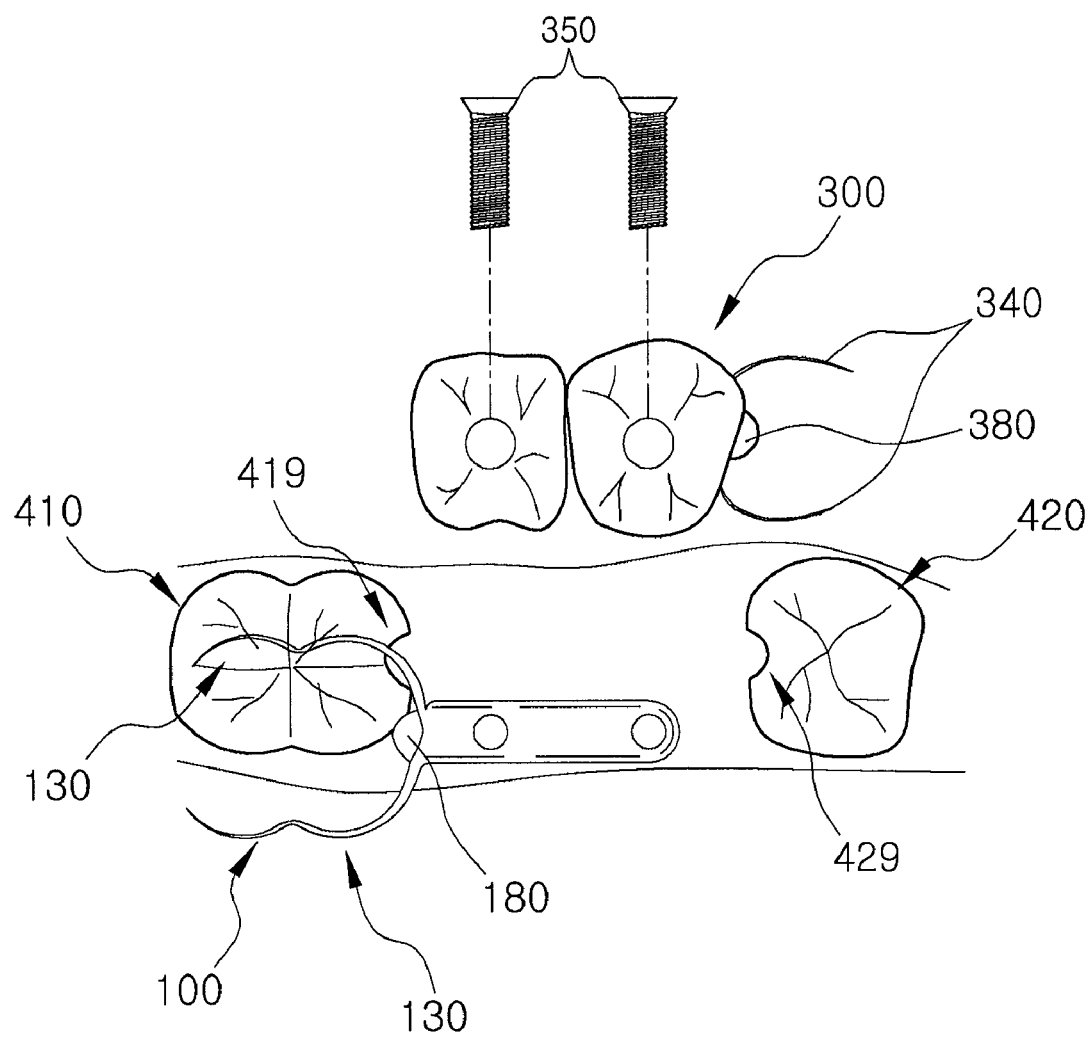

[Figure 38]
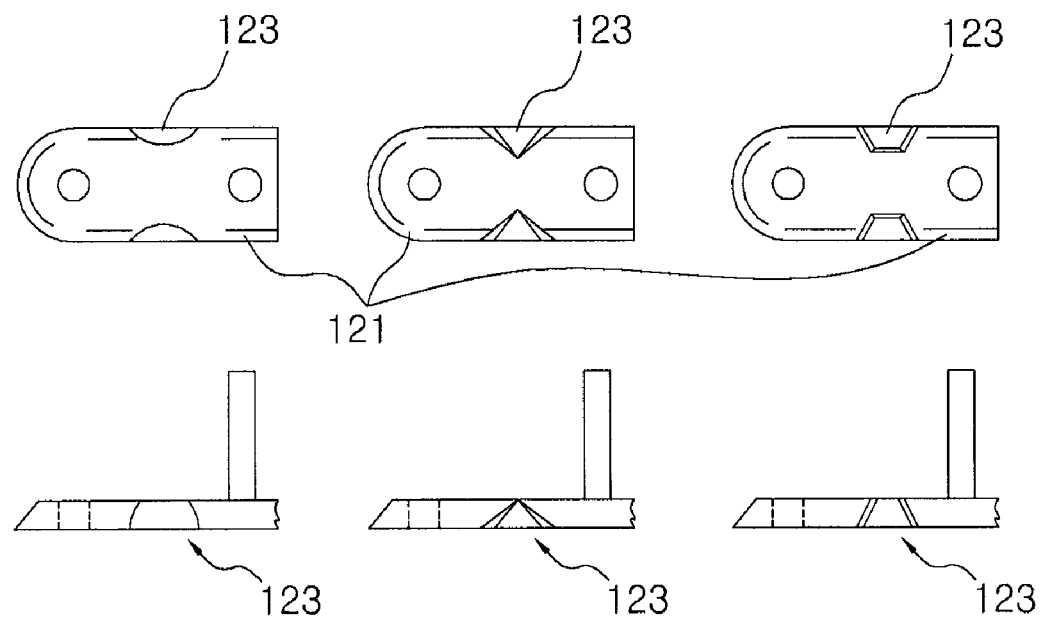
(a)
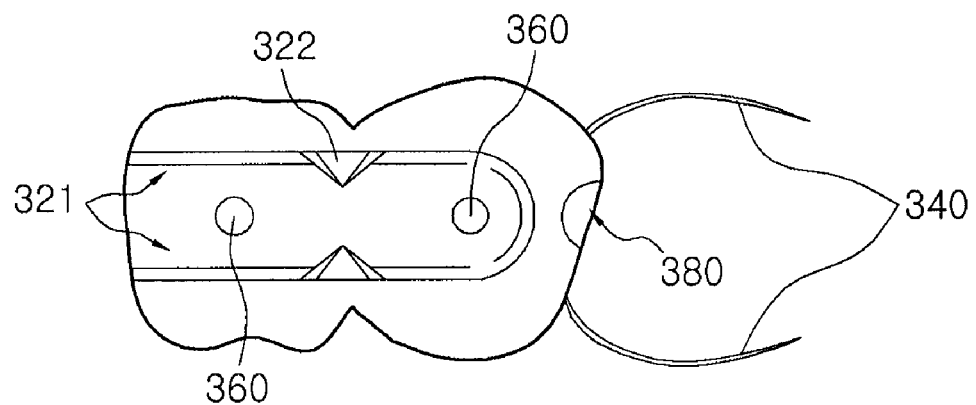
(b)

【Figure 39】
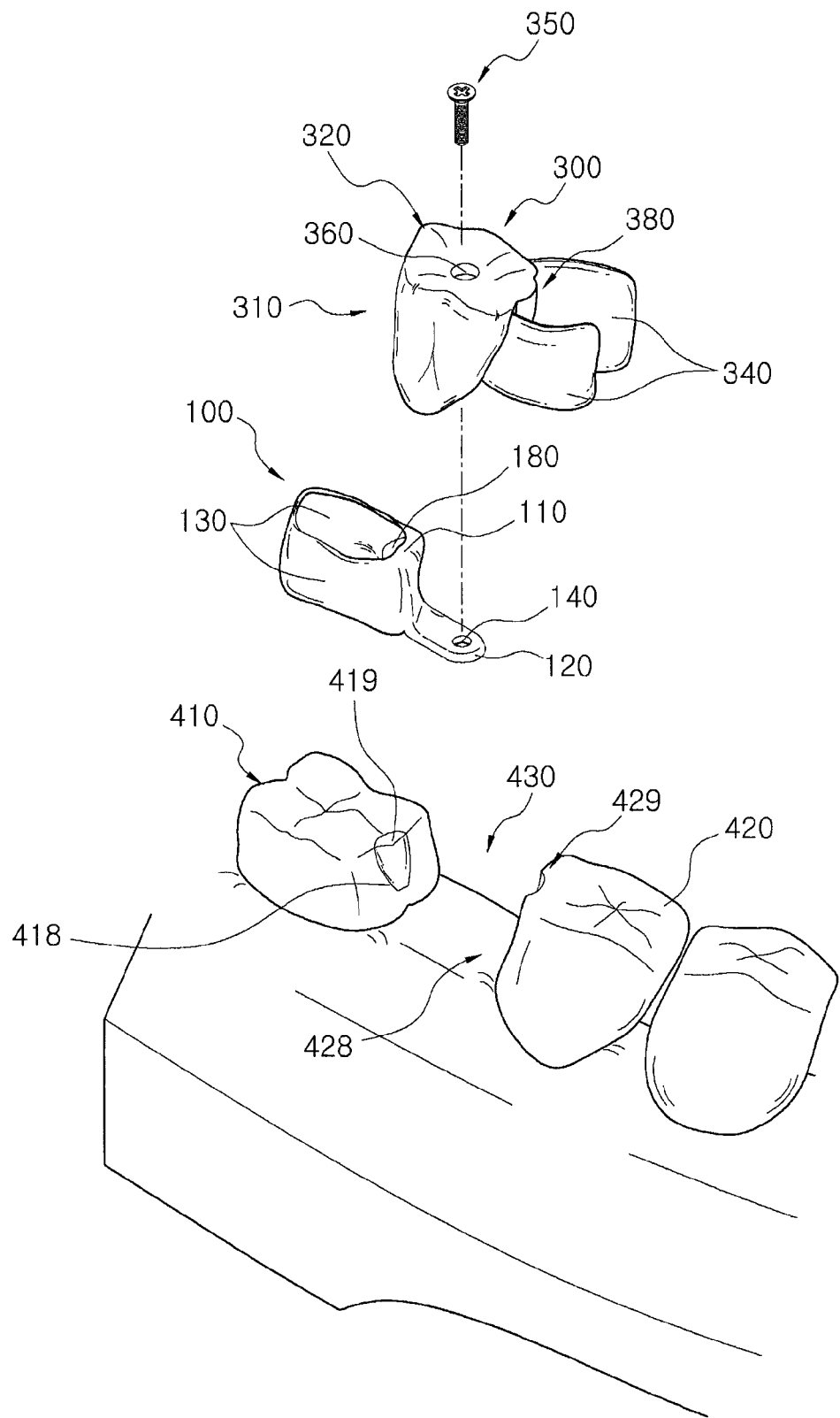

[Figure 40]
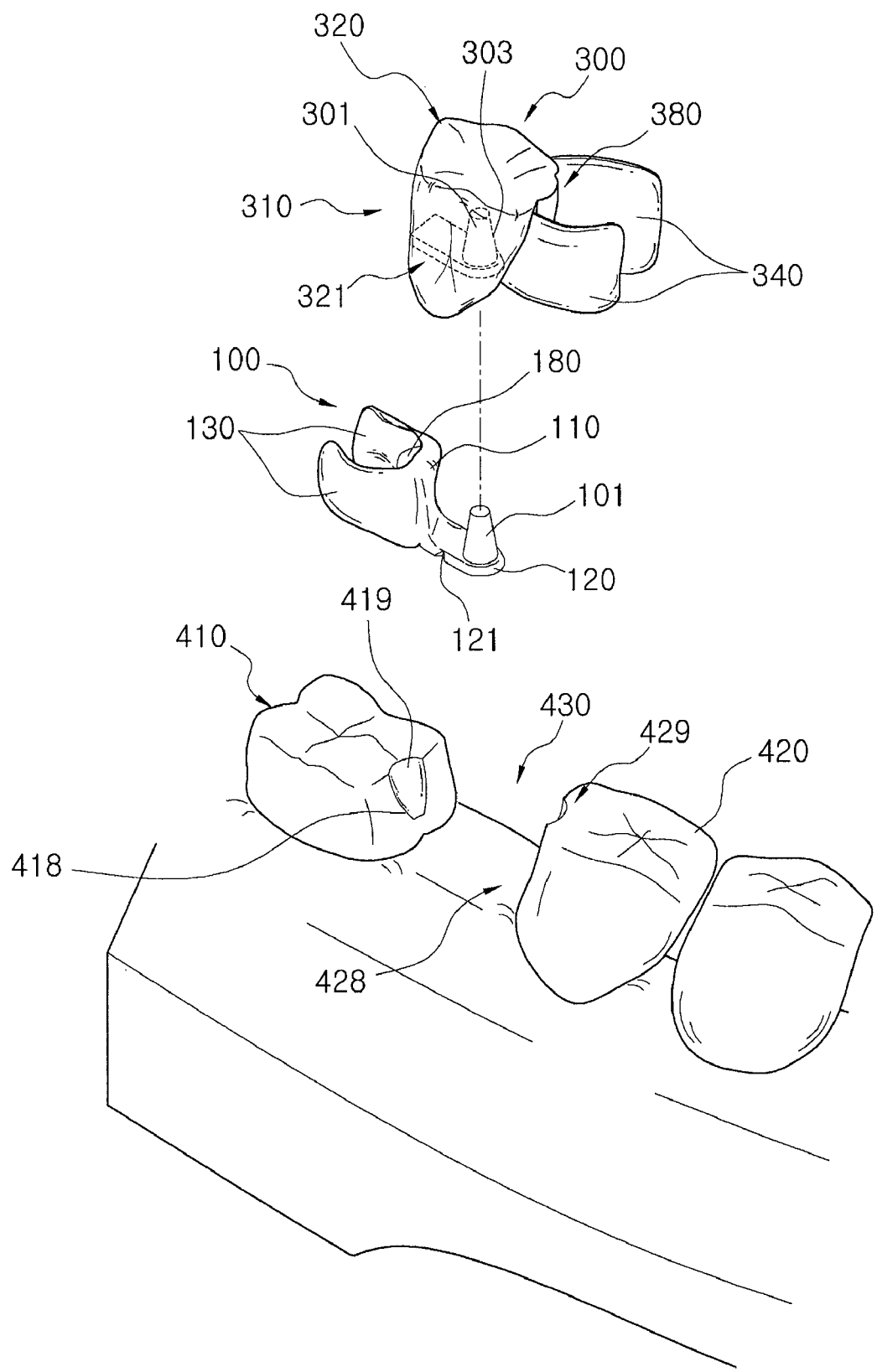

[Figure 41]
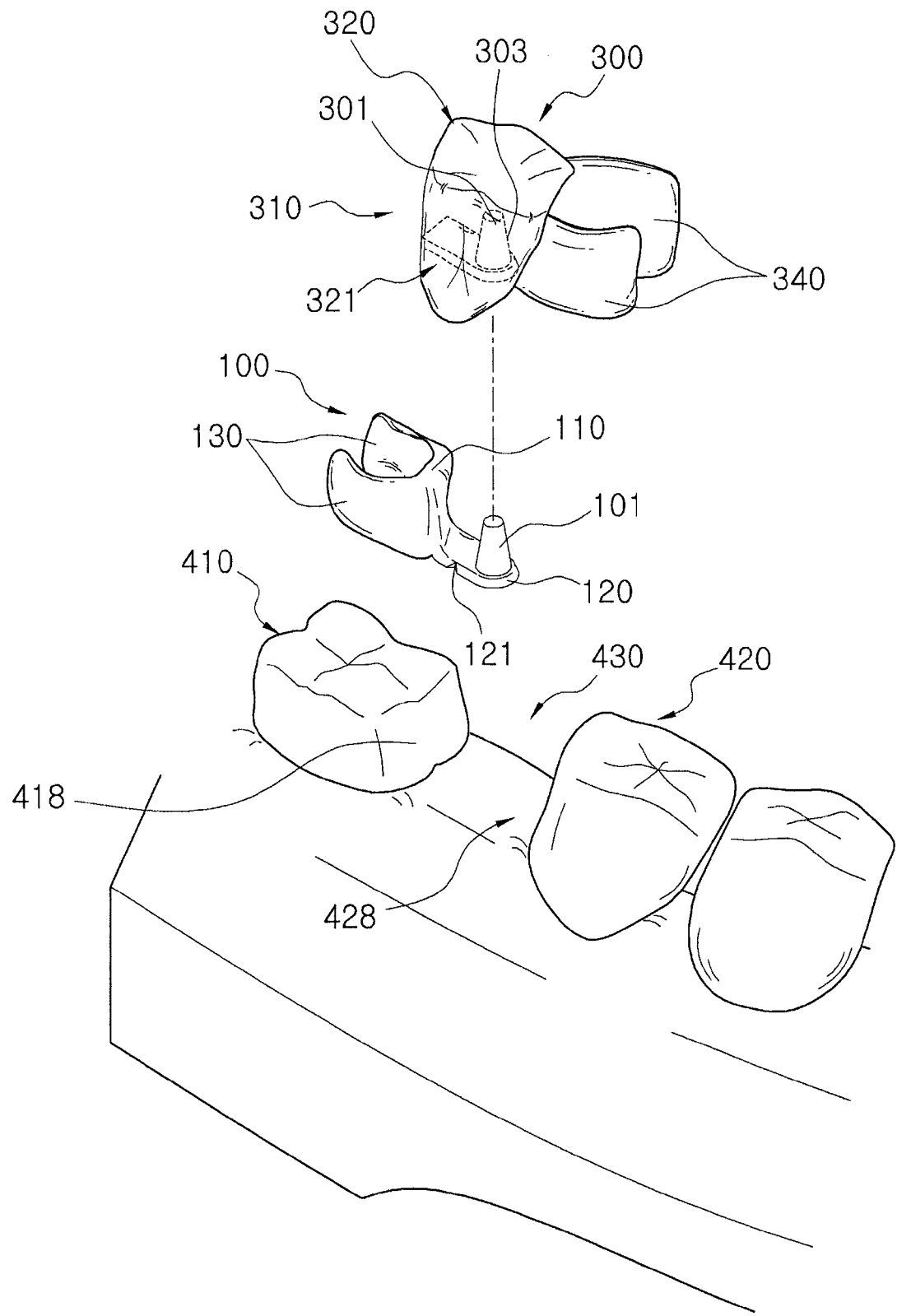

[Figure 42]
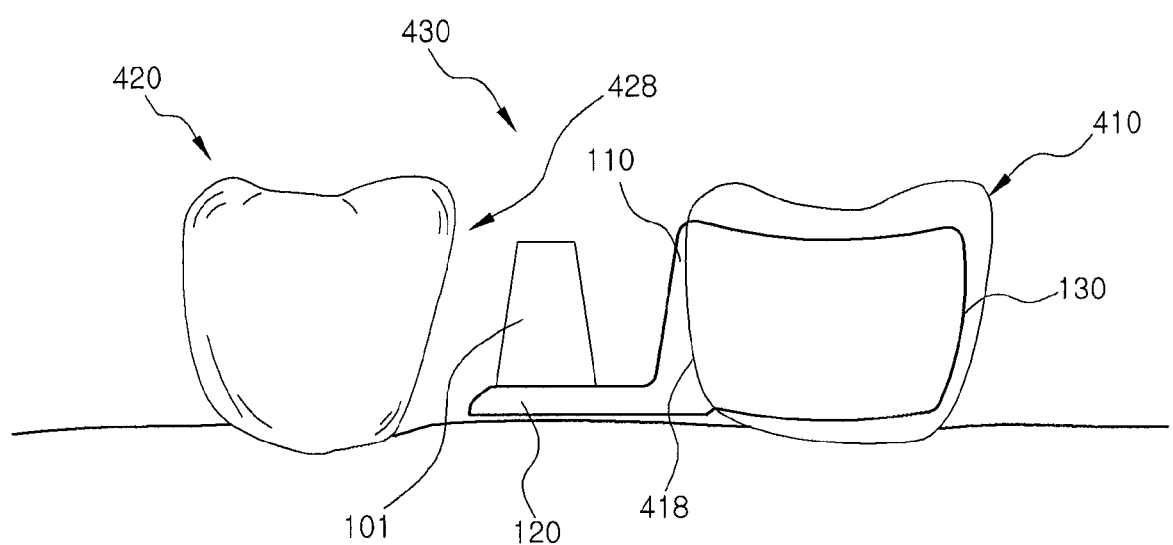

[Figure 43]
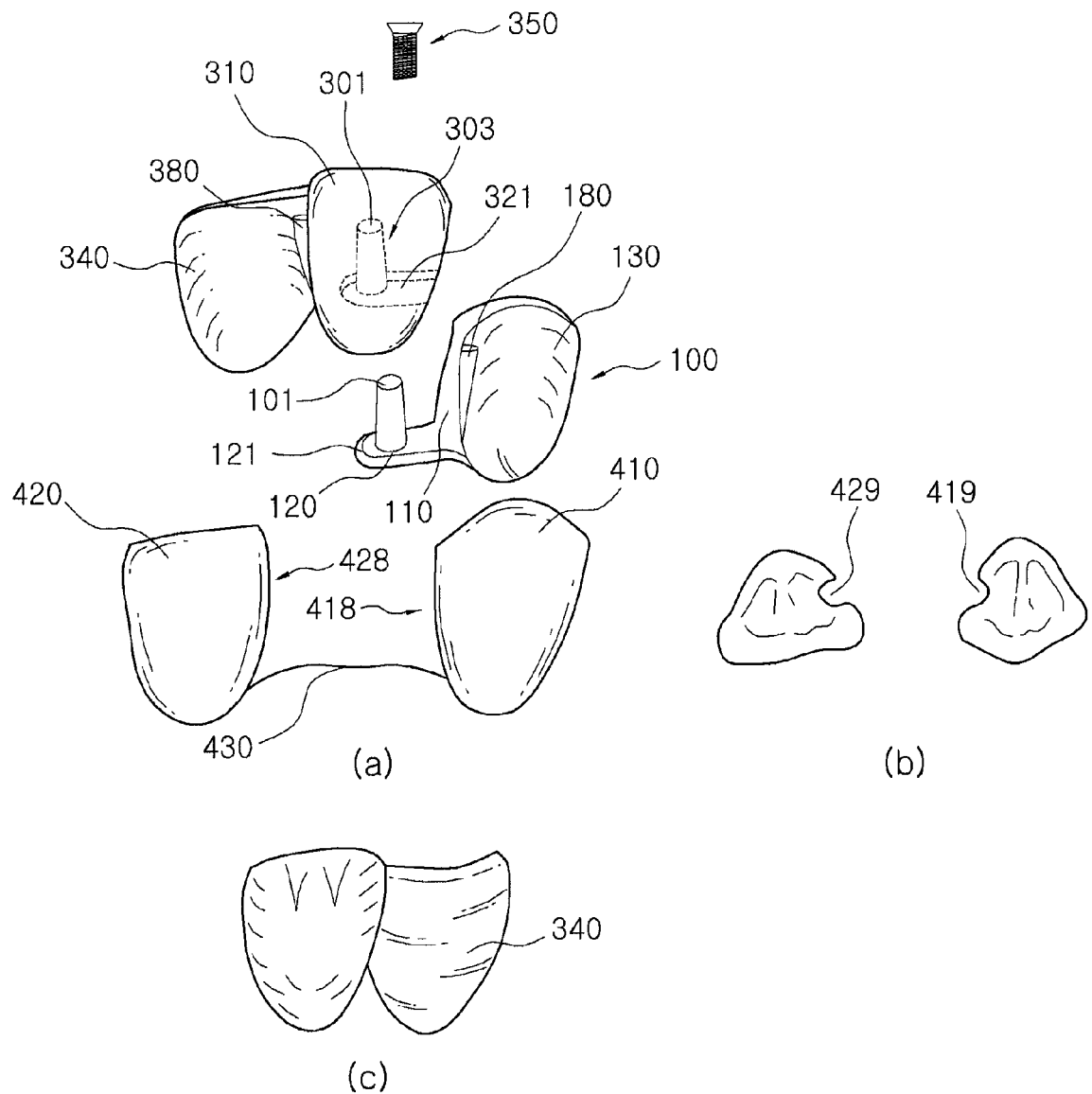
(a)　(b)
(c)

[Figure 44]
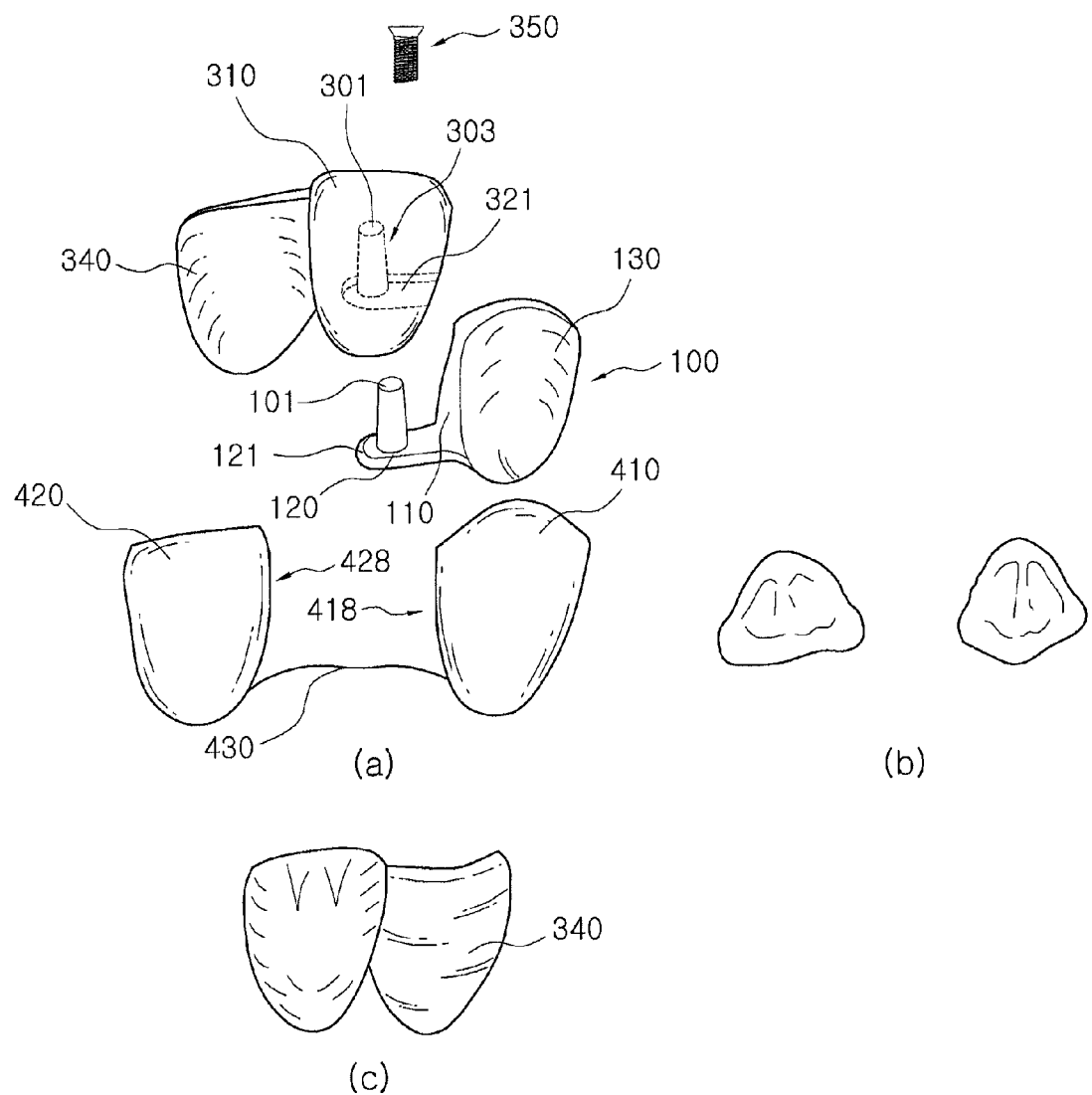

【Figure 45】
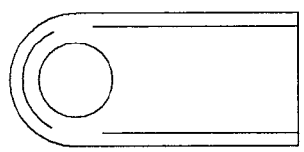
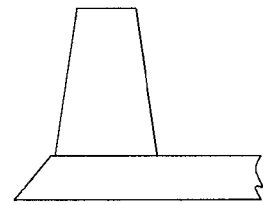
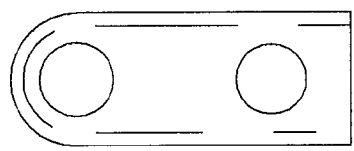
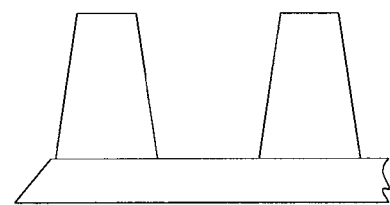
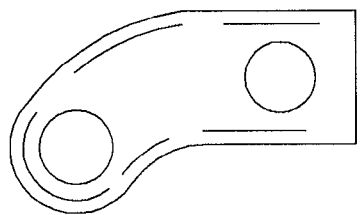
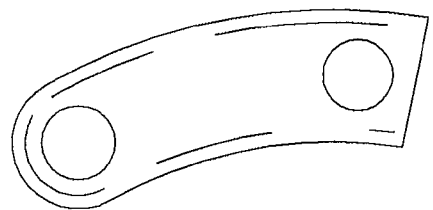
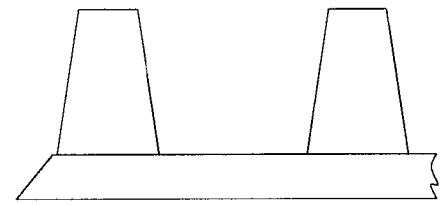
(a)                (b)

[Figure 46]
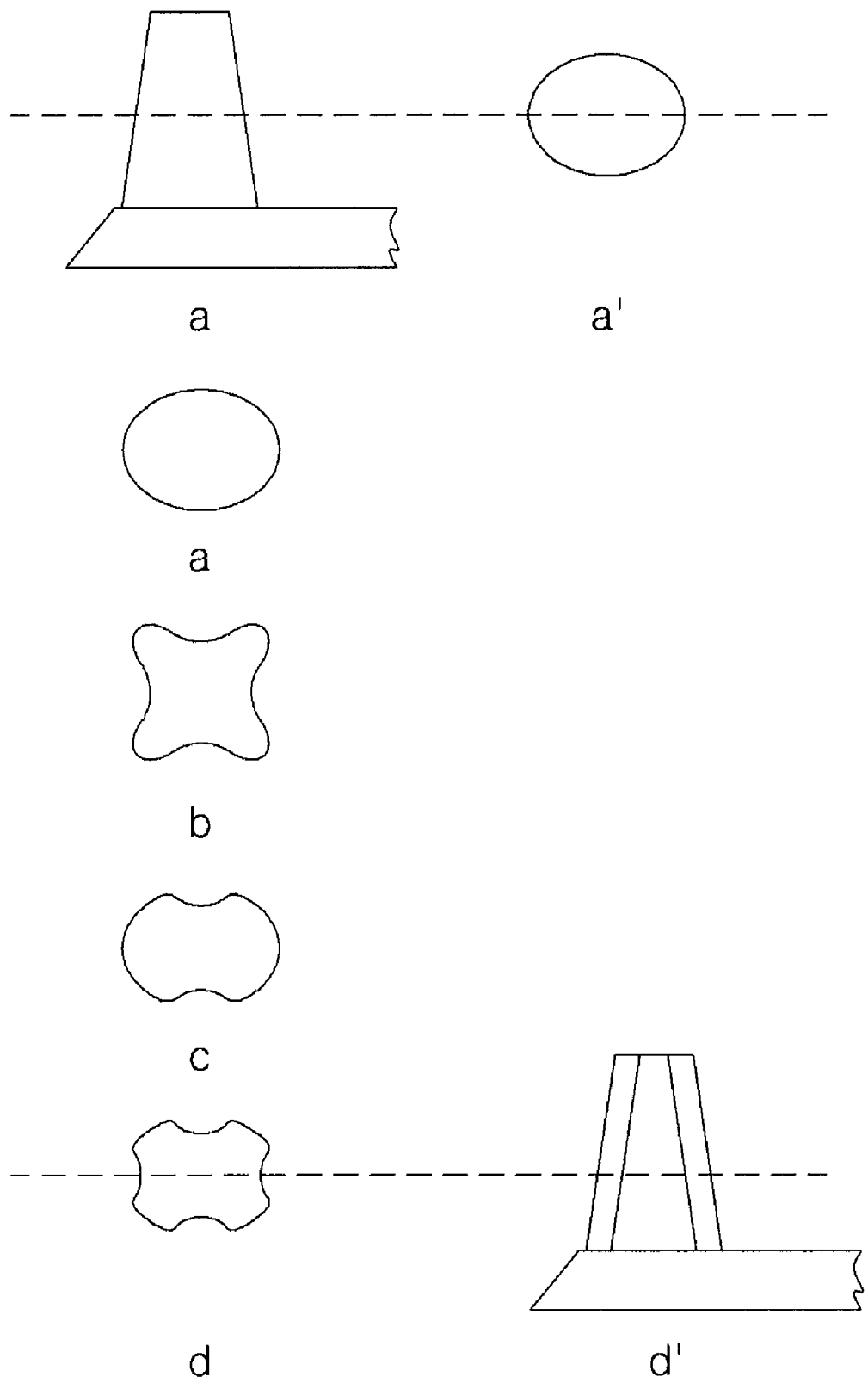

[Figure 47]
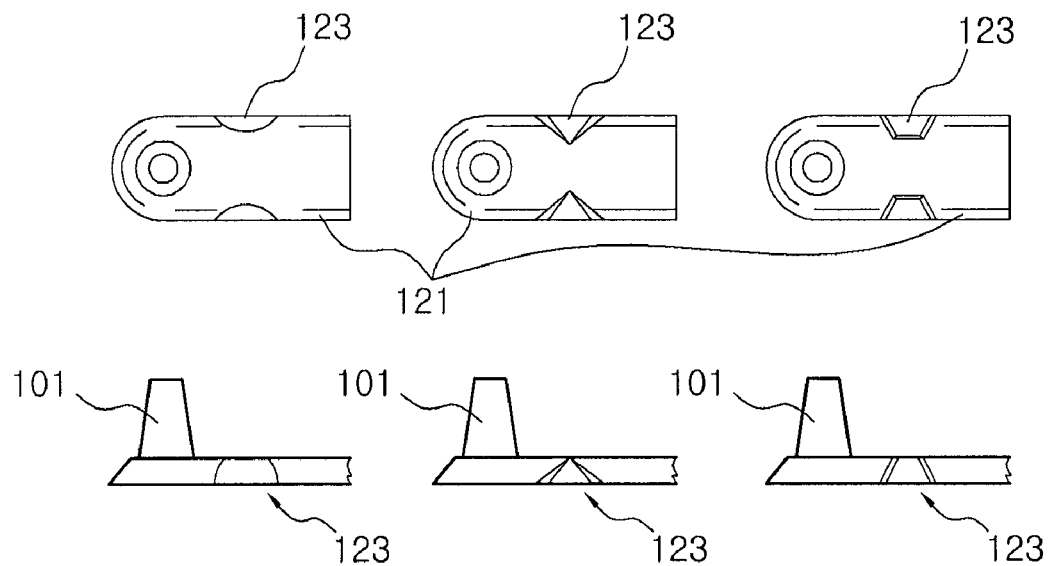
(a)
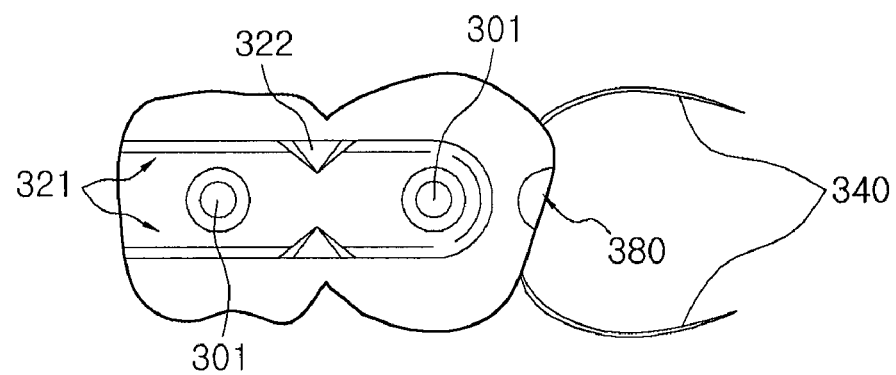
(b)

【Figure 48】
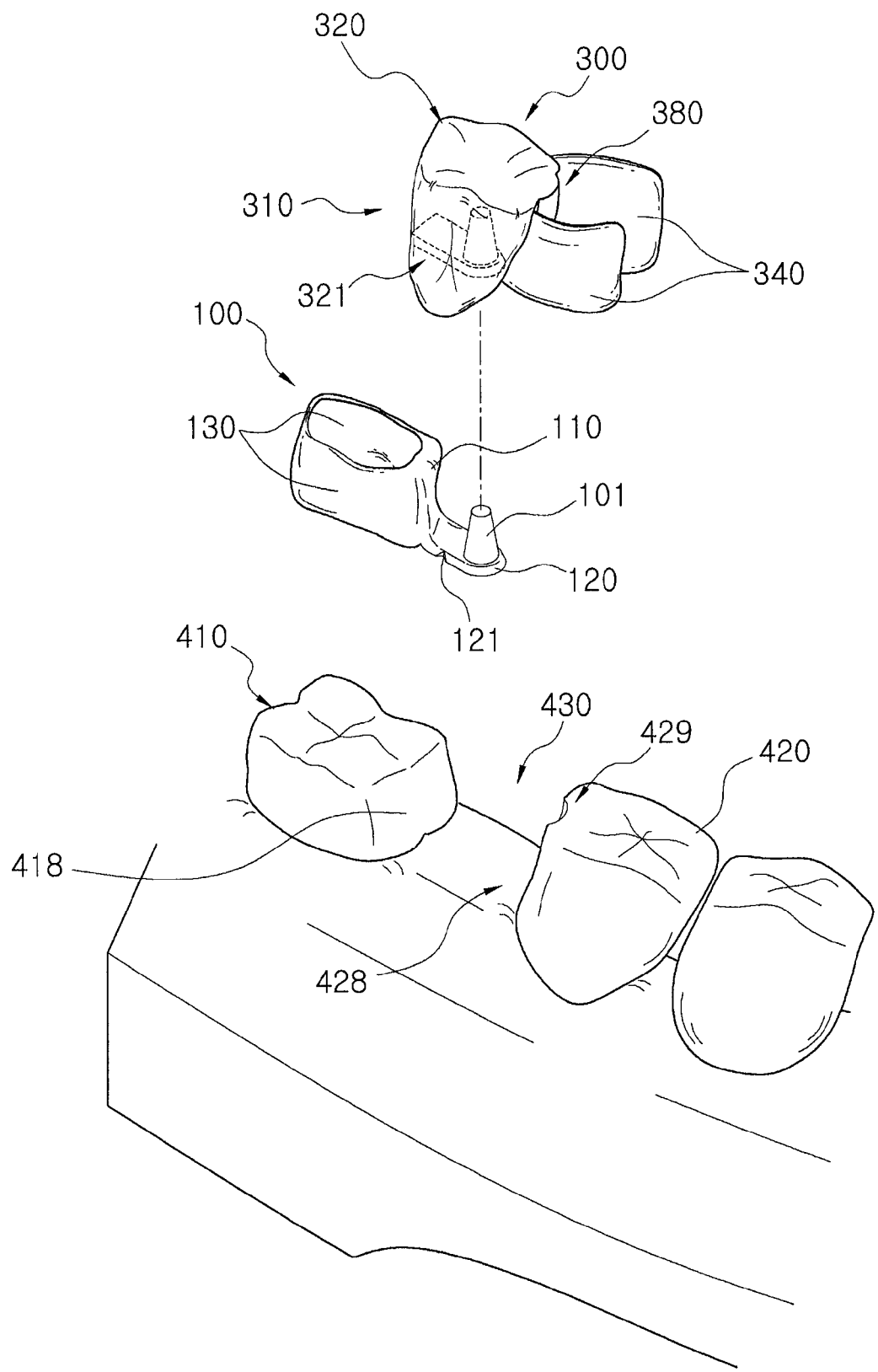

DENTAL PROSTHESIS AND MANUFACTURING METHOD THEREOF

TECHNICAL FIELD

The present invention relates to a dental prosthesis, and more particularly, to a screw-engagement type dental prosthesis which enables non-preparation of a natural tooth (abutment tooth) because it is manufactured by division into two or three pieces, which can be simply installed, and in which the occlusal pressure can be uniformly dispersed. Also, the present invention relates to a method of casting a screw-engagement type dental prosthesis by using a bolt made of carbon or ceramics.

BACKGROUND ART

In general, prosthesis is performed when a tooth is damaged or missing due to an oral disease. The prosthesis is to wrap a weak tooth or to restore a missing portion of a tooth. Among the prosthesis methods, a crown bridge is used most generally, which employs the natural tooth positioned on either side of the missing tooth as abutment teeth. As shown in FIG. 1, the crown bridge positions an artificial tooth 12 at a site where a missing tooth was positioned, and prepares a part of the abutment tooth 10, and then securely wraps a crown over the abutment tooth 10.

However, such a crown bridge has disadvantages that it causes a pain to a patient at the time of the preparation (prep) of the tooth, raises a secondary problem such as denaturalization of the dental pulp due to an increase of the prepared amount of the tooth structure of the abutment tooth, and induces exposure of the tooth pulp and hypersensitivity reaction, and the like. Also, since the occlusal surfaces of the abutment teeth are prepared, it is not possible to naturally restore the occlusal surfaces as usual.

Meanwhile, an inlay-type prosthesis as shown in FIG. 2 may be employed to prevent such disadvantages. The inlay prosthesis is to supportingly fit an artificial tooth at a site of a missing tooth, in such a manner that the inlay 22 secured to the side abutment tooth, is press-fit into a recess groove 21 of the artificial tooth 20. After drilling a hole at the abutment tooth (see numeral 10 of FIG. 10) so as to insert protrusions 24 of the inlay 22 thereto, the inlay 22 is inserted into the hole and bonded (cementing) from the upper side so that an insertion portion 27 can be inserted into the recess groove 21 of the artificial tooth 20. The inlay-type prosthesis can be regarded as prosthesis of a type of preparing the abutment tooth in a small amount because there is a small necessity of preparing the abutment tooth 10. However, such a conventional inlay-type prosthesis has a disadvantage that holes should be precisely drilled at the abutment tooth 10 to securely fix the inlay 22 to the abutment tooth 10. In other words, when the precision of the hole drilled at the abutment tooth is reduced, abnormal occlusal occurs thereby causing inconvenience of a patient.

In contrast to the inlay-type prosthesis, as shown in FIG. 3, there has been recently known a press-fitting type prosthesis. The press-fitting type prosthesis is constructed such that a plurality of support portions 33 is provided to wrap the abutment tooth 38, and a male body 37 formed at the support portion 33 is press-fit to a female body 36 of the artificial tooth 35.

The support portion 33 can be provided in plural number, if required, so that it can be easily assembled. However, the conventional press-fitting type prosthesis entails a merit that it has good occlusal and reduces pains of a patient since the abutment tooth 38 is not prepared. Nevertheless, there occurs a disadvantage that the bonding force is reduced because it is of a press-fitting type. Also, the artificial tooth 35 is to be inserted into two abutment teeth in a state where the support portion 33 is attached to the abutment tooth 38 and maintained in the course of the assembly and operation of the prosthesis. Thus, if the male body 37 and the female body 36 are not minutely mated with each other, there could be caused a disadvantage that abnormal occlusal occurs or deformation of the prosthesis occurs when it is used for a long time because it cannot endure the occlusal pressure.

DISCLOSURE

Technical Problem

Accordingly, the present invention has been made in an effort to solve the above aforementioned problems, and an object of the present invention is to provide a screw-engagement type dental prosthesis, which can be simply installed into two or three pieces without any preparation of the abutment tooth and in which the occlusal pressure can be uniformly dispersed, and a manufacturing method thereof.

Furthermore, another object of the present invention is to provide a screw-engagement type dental prosthesis, which additionally have a semi-conical maintaining portion through a small preparation of adjacent surfaces of both abutment teeth, and which can be simply installed into two pieces and uniformly disperse the occlusal pressure, and a manufacturing method thereof.

Moreover, a further object of the present invention is to provide a dental prosthesis, which can be used even in a condition where it is difficult to use bolts by substituting for an engagement force of bolts and drastically reducing the degree of difficulty in work and the number of processes, and a manufacturing method thereof.

TECHNICAL SOLUTION

To achieve the above object, the present invention provides a dental prosthesis for restoring a missing tooth, comprising: a keeper disposed to wrap an abutment tooth of one side from a lingual side; a base disposed to wrap an abutment tooth of other side and the keeper, and a body acting as an artificial tooth and engaged with the keeper and the base by means of a screw, and disposed to wrap the abutment tooth of one side or the abutment tooth of the other side in a direction opposite to a direction in which the keeper wraps.

Also, according to the dental prosthesis of the present invention, the base is disposed in a direction in which the keeper wraps the abutment tooth of the other side.

In addition, the base is provided with a base rear wall for supporting a rear wall of the body.

Moreover, the keeper includes a keeper bottom portion adapted to be seated on the missing tooth portion formed by both abutment teeth, and the base further includes a base bottom portion for wrapping the keeper bottom portion.

Furthermore, the base bottom portion is formed with an insertion recess for inserting the keeper bottom portion thereto, the insertion recess having a screw hole for the screw engagement drilled therein.

In addition, the keeper bottom portion is further formed with a keeper groove, and the insertion recess is formed with an insertion protrusion to correspond to the keeper groove.

According to another aspect of the present invention, there is provided a casting method for manufacturing a dental prosthesis, wherein a step of constructing a duplication model for casting a base and a body includes a first step of inserting a titanium bolt into a screw hole for the screw engagement, a second step of performing impression, a third step of removing the titanium bolt after curing, a fourth step of inserting a carbon or ceramic bolt into a place from which the titanium bolt is removed, and a fifth step of casting by means of engraving and filling.

Preferably the fifth step includes a step of obtaining a duplicating model by injecting filling material and a step of casting by means of engraving and filling.

In addition, the second step includes injecting impression material to an injection indicating portion, as the titanium bolt for the duplication is formed with the injection indicating portion for the duplication material, and the fourth step includes inserting the ceramic bolt to a position indicating portion, as the ceramic bolt is formed with the position indicating portion and a position determining portion.

Also, according to still another aspect of the present invention, there is provided a casting method for manufacturing a dental prosthesis, wherein a step of constructing a duplication model for casting a base and a body includes a first step of inserting a titanium bolt into a screw hole for the screw engagement, a second step of performing impression, a third step of removing the titanium bolt after curing, a fourth step of performing a wax work after obtaining a refractory model by injecting filling material for the casting, and a fifth step of casting by filling.

In addition, a sub-step of inserting a correction wire into a place, from which the titanium bolt is removed, is performed between the third step and the fourth step.

Furthermore, a female screw drilled at the dental prosthesis is formed by casting after obtaining a carbon bolt or a ceramic bolt by turning and grinding the compressed carbon and the compressed and sintered ceramic.

To achieve the above object, in case of a molar tooth portion of FIG. 24, the present invention provides a dental prosthesis for restoring a missing tooth, comprising: a keeper disposed to wrap an abutment tooth of one side from a lingual side and a buccal side; and a body disposed to wrap an abutment tooth of the other side from the lingual side and the buccal side, the body acting as an artificial tooth and engaged with the keeper by means of a screw.

In case of a front tooth portion of FIG. 27, the present invention provides a dental prosthesis for restoring a missing tooth, comprising: a keeper disposed to simultaneously wrap an abutment tooth of one side at adjacent surfaces of a lingual side and a lip side; and a body disposed to wrap an abutment tooth of the other side at adjacent surfaces of the lingual side and the lip side, the body acting as an artificial tooth and engaged with the keeper by means of a screw.

As another embodiment of a molar tooth portion of FIG. 33, in case where an abutment tooth of one side used as a keeper is the rearmost tooth, the present invention provides a dental prosthesis for restoring a missing tooth, comprising: a keeper disposed to simultaneously wrap an abutment tooth of one side from a lingual side, a buccal side and a distal center side; and a body disposed to simultaneously wrap an abutment tooth of the other side from the lingual side and the buccal side, the body acting as an artificial tooth and engaged with the keeper by means of a screw.

The keeper includes a keeper bottom portion seated on a missing tooth portion located between the abutment teeth of both sides, and the body includes a body bottom portion adapted to wrap the keeper bottom portion while acting as an artificial tooth. The body bottom portion has an insertion recess for inserting the keeper bottom portion thereinto, and a screw hole for a screw-engagement is drilled at the insertion recess. The keeper bottom portion additionally includes a keeper groove and the insertion recess of the body includes an insertion protrusion corresponding to the keeper groove.

In another aspect of the present invention, the present invention provides a manufacturing method of a dental prosthesis comprising a step of constructing a duplication model for casting a body, the duplication model constructing step including: a first step of inserting a titanium bolt into a screw hole drilled in a keeper for screw engagement, a second step of performing impression, a third step of removing the titanium bolt, a stone model and the previously manufactured keeper after curing, a fourth step of inserting a carbon or ceramic bolt into a place from which the titanium bolt is removed, and a fifth step of casting by means of engraving and filling.

Preferably, the fifth step includes a step of obtaining a duplication model by injecting filling material and a step of performing casting by means of engraving and filling.

Here, since the titanium bolt has an injection indicating portion for guiding injection of duplication material, in the second step, impression material is injected up to the injection indicating portion. Moreover, since the ceramic bolt has a position indicating portion, in the fourth step, the bolt is inserted up to the position indicating portion.

Furthermore, a female is drilled at the dental prosthesis according to a casting method using a carbon bolt and a ceramic bolt, which are respectively obtained by turning compression-molded carbon and compression-molded and sintered ceramic.

In addition, to achieve the above objects, in case of a molar tooth portion of FIG. 34, the present invention provides a dental prosthesis for restoring a missing tooth, comprising: a keeper disposed to wrap an abutment tooth of one side from a lingual side and a buccal side; a body disposed to wrap an abutment tooth of the other side from the lingual side and the buccal side, the body acting as an artificial tooth and engaged with the keeper by means of a screw; and thin and semi-conical keys disposed on the inner inclination surfaces of the keeper and the body.

In case of a front tooth portion of FIG. 36, the present invention provides a dental prosthesis for restoring a missing tooth, comprising: a keeper disposed to simultaneously wrap an abutment tooth of one side at adjacent surfaces of a lingual side and a lip side; a body disposed to wrap an abutment tooth of the other side at adjacent surfaces of the lingual side and the lip side, the body acting as an artificial tooth and engaged with the keeper by means of a screw; and thin and semi-conical keys disposed on the inner inclination surfaces of the keeper and the body.

As another embodiment of a molar tooth portion of FIG. 39, in case where an abutment tooth of one side used as a keeper is the rearmost tooth, the present invention provides a dental prosthesis for restoring a missing tooth, comprising: a keeper disposed to simultaneously wrap an abutment tooth of one side from a lingual side, a buccal side and a distal center side; and a body disposed to simultaneously wrap an abutment tooth of the other side from the lingual side and the buccal side, the body acting as an artificial tooth and engaged with the keeper by means of a screw. The keeper includes a keeper bottom portion seated on a missing tooth portion located between the abutment teeth of both sides, and the body includes a body bottom portion adapted to wrap the keeper bottom portion while acting as an artificial tooth. The body bottom portion has an insertion recess for inserting the keeper bottom portion thereinto, and a screw hole for a screw-engagement is drilled at the insertion recess. The keeper bottom portion additionally includes a keeper groove and the insertion recess of the body includes an insertion protrusion corresponding to the keeper groove.

Furthermore, to achieve the above objects, in case of a molar tooth portion of FIG. 41, the present invention provides a dental prosthesis for restoring a missing tooth, comprising: a keeper disposed to wrap an abutment tooth of one side from a lingual side and a buccal side, the keeper having a keeper male, which is an engagement portion; a body disposed to wrap an abutment tooth of the other side from the lingual side and the buccal side, the body acting as an artificial tooth and having a body female engaged with the keeper male through friction resistance. In FIG. 40, the dental prosthesis further comprises thin and semi-conical keys disposed on the inner inclination surfaces of the keeper and the body. In case of a dental prosthesis with non-preparation shown in FIG. 41, the keys are not formed on the inner inclination surfaces of the keeper and the body.

As another embodiment of a molar tooth portion of FIG. 48, in case where an abutment tooth of one side used as a keeper is the rearmost tooth, the present invention provides a dental prosthesis for restoring a missing tooth, comprising: a keeper disposed to simultaneously wrap an abutment tooth of one side from a lingual side, a buccal side and a distal center side; and a body disposed to simultaneously wrap an abutment tooth of the other side from the lingual side and the buccal side, the body acting as an artificial tooth and engaged with the keeper by means of a screw. The keeper includes a keeper bottom portion seated on a missing tooth portion located between the abutment teeth of both sides, and the body includes a body bottom portion adapted to wrap the keeper bottom portion while acting as an artificial tooth. The body bottom portion has an insertion recess for inserting the keeper bottom portion thereinto, and the keeper male for the friction resistance may be formed on the inner portion of the insertion recess. Moreover, the keeper bottom portion additionally includes a keeper groove and the insertion recess of the body includes an insertion protrusion corresponding to the keeper groove.

Advantageous Effects

As described above, according to the dental prosthesis of the present invention, it is not necessary to prepare the abutment tooth so that the pains of a patient and occurrence of a secondary problem can be minimized, and it can be simply installed, and it is possible to disperse the occlusal pressure uniformly so that the dental operation can be facilitated. Also, it is possible to drill an accurate screw engagement hole by using a specially devised titanium bolt or a ceramic bolt.

Furthermore, the dental prosthesis according to the present invention can reinforce a maintaining force thereof since the thin and semi-conical keys disposed on the inner inclination surfaces of the keeper and the body, minimize pains of a patient and secondary problems by providing an aesthetic dental prosthesis, be simply installed, and uniformly disperse occlusal pressure. Particularly, in case of the front tooth portion, since an aesthetic aspect is as important as a function, the present invention can more improve the aesthetic aspect and provide an excellent function by minimizing the maintaining portion of the inner inclination surface of the lip side of the front tooth.

Moreover, since the dental prosthesis, which has no preparation or has the thin and semi-conical key formed on the inner inclination surface of the body, applies not a bolt engagement method but a principle to provide the maintaining force of friction resistance of a double-pipe prosthesis, the present invention can secure necessary maintaining force through the friction resistance of the keeper male and the body female, reduce the number of work processes requiring high-grade skills, and drastically reduce manufacturing costs as it does not sue various bolts. Accordingly, the dental prosthesis according to the present invention can be provided inexpensively by reducing necessary time period and expenses but enhancing productivity, and hence, reduce a patient's financial burden.

DESCRIPTION OF DRAWINGS

FIG. 1 is a construction view of a conventional bridge prosthesis.

FIG. 2 is a construction view of a conventional inlay-type prosthesis.

FIG. 3 is a construction view of a conventional press fitting type prosthesis.

FIG. 4 is a whole perspective view of the present invention.

FIG. 5 is an assembly view of an upper surface of a missing tooth portion of the present invention.

FIG. 6 is a front view of a buccal side of a keeper of the present invention.

FIG. 7 is a front view of a buccal side of a base of the present invention.

FIG. 8 is a rear view of a lingual side of a body of the present invention.

FIG. 9 is an assembly view of an upper portion of the two missing tooth portions of the present invention.

FIG. 10 is an assembly view of four missing front tooth portions of the present invention.

FIG. 11 is a view explaining the attachment of a plastic keeper for performing a primary casting according to the present invention.

FIG. 12 is a view explaining the position determining work of a ceramic bolt for forming a female screw of a keeper for performing the primary casting according to the present invention.

FIG. 13 is a top plan view showing bottom shapes of several keepers.

FIG. 14 is a view explaining a duplication model work for the secondary casting.

FIG. 15 is a view explaining a duplication model work for the tertiary casting.

FIG. 16 is a side view of a bolt for the duplication and casting.

FIG. 17 is a view explaining a bottom portion of a keeper according to second embodiment of the present invention.

FIG. 18 is a side view of a bolt for the duplication and casting of third embodiment of the present invention.

FIG. 19 is a view explaining a duplication model work for the secondary casting according to fourth embodiment of the present invention.

FIG. 20 is a side view forming female screws at a keeper hole, a base hole, and a body hole of the present invention.

FIG. 21 is a side view forming female screws at a keeper hole and a base hole of the present invention.

FIG. 22 is a side view forming a female screw at a keeper hole of the present invention.

FIG. 23 is an entire perspective view of fifth embodiment of the present invention.

FIG. 24 is an entire perspective view of a molar tooth portion of the present invention using a dental prosthesis divided into two pieces.

FIG. 25 (*a*) is an assembly view of an upper surface of a missing tooth portion of the present invention using the dental prosthesis divided into two pieces, and (b) is a cross-sectional view of a main portion of a body and an occlusal portion viewed from a portion engaged with a keeper outer wall.

FIG. 26 is a front view of a buccal side of a keeper of the present invention using a dental prosthesis divided into two pieces.

FIG. 27 (a) is an assembly view of a front tooth portion of the present invention using the dental prosthesis divided into two pieces, and (b) is a view of a body lingual side of the front tooth portion.

FIG. 28 is an assembly view of an upper surface of the two missing tooth portions of the present invention using the dental prosthesis divided into two pieces.

FIG. 29 is a view explaining the attachment of a plastic keeper for performing a primary casting according to the present invention using the dental prosthesis divided into two pieces.

FIG. 30 is a view explaining the position determining work of a ceramic bolt for forming a female screw of the keeper by performing the primary casting according to the present invention using the dental prosthesis divided into two pieces.

FIG. 31 is a view explaining a duplication model work for the secondary casting according to the present invention using the dental prosthesis divided into two pieces.

FIGS. 32 (a) and (b) are views explaining a keeper bottom portion and a body bottom portion according to a seventh embodiment of the present invention using the dental prosthesis divided into two pieces.

FIG. 33 is a view of another example of the molar tooth portion using the dental prosthesis divided into two pieces.

FIG. 34 is an entire perspective view of the molar tooth portion using a maintaining portion and a key.

FIG. 35 (a) is an assembly view of an upper surface of a missing tooth portion of the present invention using the maintaining portion and the key, and (b) is a cross-sectional view of a main portion of a body and an occlusal portion viewed from a portion engaged with a keeper outer wall.

FIG. 36 (a) is an assembly view of a front tooth portion of the present invention using the maintaining portion and the key, (b) is a plan view, in section, of the front tooth portion, and (c) is a view of a lingual side of a body of the front tooth portion.

FIG. 37 is an assembly view of an upper surface of two missing tooth portions of the present invention using the maintaining portion and the key.

FIG. 38 (a) is a view explaining a keeper bottom portion according to a tenth embodiment of the present invention using the maintaining portion and the key, and (b) is a view explaining a body bottom portion.

FIG. 39 is a view of another embodiment of a molar tooth portion of the present invention using the maintaining portion and the key.

FIG. 40 is an entire perspective view of a molar tooth portion of the present invention using a keeper male and a body female.

FIG. 41 is an entire perspective view of a molar tooth portion with non-preparation according to the present invention using the keeper male and the body female.

FIG. 42 is a front view of a buccal side of a keeper using the keeper male and the body female.

FIG. 43 (a) is an assembly view of a front tooth portion according to the present invention using the keeper male and the body female, (b) is a view of a key-forming portion viewed from a lingual side cut face, and (c) is a view of a lingual side of a body of the front tooth portion.

FIG. 44 (a) is an assembly view of a front tooth portion with non-preparation according to the present invention using the keeper male and the body female, (b) is an assembly view of a tooth with non-preparation viewed from the lingual side cut face, and (c) is a view of a lingual side of a body of the front tooth portion with non-preparation type.

FIG. 45 (a) is a view of an upper portion showing forms of various keeper bottom portions according to the present invention using the keeper male and the body female, and (b) is a side view showing a keeper male form.

FIG. 46 is a sectional view of various keeper males for increasing a friction force according to the present invention using the keeper male and the body female.

FIG. 47 (a) is an explanation view of a keeper bottom portion according to a thirteenth embodiment of the present invention using the keeper male and the body female, and (b) is an explanation view of a body bottom portion.

FIG. 48 is a view showing another embodiment of the molar tooth portion according to the present invention using the keeper male and the body female.

MODE FOR INVENTION

Hereinafter, the preferred embodiments of the present invention will be described in detail with reference to the appended drawings.

In the present invention, FIGS. 1 to 23 illustrate a dental prosthesis divided into three pieces, wherein FIG. 4 is an entire perspective view of the present invention, FIG. 5 is an assembly view of an upper surface of a missing tooth portion of the present invention, FIGS. 6, 7, and 8 are views showing a keeper, a base, and a body of the present invention, FIG. 9 is an assembly view of an upper portion of the two missing tooth portions of the present invention, FIG. 10 is an assembly view of four missing front tooth portions of the present invention, FIGS. 11 and 15 are views explaining a manufacturing method of the present invention, FIG. 16 is a side view of a bolt for the duplication and casting.

FIGS. 24 to 48 illustrate a dental prosthesis divided into two pieces, wherein FIG. 24 is an entire perspective view of a molar tooth portion of the present invention, FIG. 25 is an assembly view of an upper surface of a missing tooth portion, and FIG. 26 is a view of a keeper of the present invention.

FIG. 27 is an assembly view of a front tooth portion, FIG. 28 is an assembly view of an upper surface of the two missing tooth portions of the present invention, and FIGS. 29 to 31 are views for explaining manufacturing method of the present invention, and FIG. 33 is a view of another example of the molar tooth portion.

FIG. 34 is an entire perspective view of a molar tooth portion using a prosthesis having semi-conical keys 180 and 380, and FIG. 35 is an assembly view of an upper portion of one missing molar tooth portion. FIG. 36 is an assembly view of a front tooth portion using the prosthesis having the semi-conical keys 180 and 380, FIG. 37 is an assembly view of an upper portion of two missing molar tooth portions, and FIG. 39 is a view showing another embodiment of the molar tooth portion.

FIG. 40 is an entire perspective view of a molar tooth portion using a keeper male 101 and a body female 301, FIG. 41 is an entire perspective view of a molar tooth portion with non-preparation, and FIG. 42 is a view of a keeper according to the present invention.

FIG. 43 (a) is an assembly view of a front tooth portion using the keeper male 101 and the body female 301, (b) is a view of a key-forming portion viewed from a lingual side cut face, and (c) is a view of a lingual side of a body of the front tooth portion using a key. FIG. 44 (a) is an assembly view of a front tooth portion with non-preparation using the keeper male 101 and the body female 301, (b) shows a non-preparation tooth state viewed from the lingual side cut face, and (c) is a view of a lingual side of a body of the front tooth portion with non-preparation type.

FIG. 45 (a) is a view of an upper portion showing forms of various keeper bottom portions using the keeper male 101 and the body female 301, (b) is a side view showing a keeper male form, and FIG. 46 is a sectional view of various keeper males 101 for increasing a friction force. FIG. 47 (a) is an explanation view of a keeper bottom portion according to a thirteenth embodiment of the present invention, FIG. 47b is an explanation view of a body bottom portion according to the thirteenth embodiment, and FIG. 48 is a view showing another embodiment of the molar tooth portion using the keeper male 101 and the body female 301.

In the drawings, dispensable portions are omitted to clarify the technical gist of the present invention, and the omitted portions are the same as those shown in the conventional dental prosthesis and manufacturing method thereof.

Hereinafter, the present invention will be described in more detail with reference to the concrete embodiments.

(First Embodiment)

Hereinafter the screw-engagement type dental prosthesis with non-preparation according to a first embodiment of the present invention will be described with reference to FIGS. 4 through 8.

As shown in FIG. 4, the dental prosthesis of the present invention comprises a keeper 100 wrapping an abutment tooth 410 of one side from a lingual side, a base 200 wrapping an abutment tooth 420 of the other side from the lingual side, and a body 300 inserted into a missing tooth portion 430 and wrapping the abutment tooth 410 from a buccal side in case of a molar tooth portion, and wrapping an inner inclination surface of the lip side of both abutment teeth 410, 420 in case of a front tooth portion.

Also, bolt engagement holes, which penetrate desired portions, are drilled at the keeper 100, the base 200, and the body 300, by means of a casting method using a ceramic bolt 350. While the keeper 100 and the base 200 wrap both abutment teeth 410, 420 from the lingual side, the body 300 wraps them from the buccal side or the lip side, so that they can be firmly supported by means of a screw engagement using common holes.

In addition, as shown in FIG. 5, since respective portion is divided into three pieces and are assembled in sequence, advantages are obtained that it is not necessary to prepare (prep) the abutment tooth 420, and the inconvenience of a patient is minimized and the assembly is simple.

Respective portion is described in more detail with reference to FIG. 6 through FIG. 8. In FIG. 6, the keeper 100 of the present invention is shown. The keeper 100 comprises largely a keeper wall 110, a keeper bottom portion 120, and a keeper plate 130. The keeper plate 130 and an inner surface of the keeper wall 110 wrap substantially the lingual side and a portion of the distal center of the abutment tooth 410, and the keeper bottom portion 120 is connected to a lower end of the keeper bottom portion 120. The keeper bottom portion 120 is a portion directly contacting with the missing tooth portion 430, and is manufactured according to the manufacturing method of the prosthesis including performing impression, waxing up, casting, and the like, so that it can duplicate the shape of the missing tooth portion 430 without causing any inconvenience. An outer surface of the keeper wall 110 has an inclination angle of 2 to 4° with respect to the vertical line and is positioned at a side of the abutment tooth 410. An inner surface of the keeper wall 110 is manufactured to duplicate an undercut of the abutment tooth 410 according to the general manufacturing method of the prosthesis. The support force of the prosthesis can be further improved by the close contact of the inner surface of the keeper wall with the undercut of the abutment tooth 410. Detailed description of the manufacturing method thereof will be explained below.

Meanwhile, the keeper plate 130 wraps the abutment tooth 410 from the lingual side and is manufactured to duplicate the shape of the abutment tooth 410 as is the keeper wall 410. While the keeper plate 130 wraps the abutment tooth from the lingual side, the body 300 screw-engaged with the keeper plate wraps it from the buccal side or the lip side, so that bonding force is secured in the front and rear teeth portions. The keeper bottom portion 120 is a portion, which is inserted into an insertion recess 221 of the base 200, and is drilled with a keeper hole 140. The keeper hole 140 is formed with a female screw so that a locking bolt 350 can be inserted into it. The keeper bottom portion 120 is formed with a bottom inclination surface 121 to facilitate the assembly with the base 200. Meanwhile, the keeper bottom portion 120 can be formed into several shapes according to the shape and position of the missing tooth portion 430. As shown in FIG. 13, the length of the keeper bottom portion 120 is varied according to the width of the missing tooth portion 430, and if the missing tooth portion 430 is curved, the keeper bottom portion 120 of a curved shape is used. While the keeper 100 is manufactured according to the general manufacturing method of the prosthesis, it is cast by using a carbon or ceramic bolt to form the accurate female screw at the keeper hole 140. The detailed manufacturing method will be described below.

Next, the base 200 of the prosthesis of the present invention will be described with reference to FIGS. 4 and 7.

The base 200 is a portion wrapping the other abutment tooth 420 from the lingual side, and is provided with a base plate 230 and a base rear wall 240 substantially wrapping the abutment tooth 420 with respect to the base wall 210. The base wall 210 is formed with a base bottom portion 220 at the lower end. The base wall 210 is disposed at the missing tooth portion 430 positioned between the abutment teeth 410, 420, and the inner surface is manufactured to duplicate the undercut of the abutment tooth 420 as it is. As the base wall 210 is basically formed inclined by 2 to 4° with respect to the vertical line, the assembly of the body 300 is not suffered from any resistance from any direction. As shown in FIG. 7, since the base wall 210 is firmly inserted and engaged with the undercut of the abutment tooth 420, the support force of the prosthesis is excellent in the directions of the front and rear tooth and in the upward direction. A base rear wall 240 is a wall portion for supporting the main portion 310 of the body 300 from the lingual side.

Meanwhile, the base bottom portion 220 is formed with an insertion recess 221 for receiving the keeper bottom portion 120. The insertion recess 221 covers the keeper bottom portion 120 and supports it firmly. As the keeper bottom portion 120 is formed long along the missing tooth portion 430, the keeper 100 and the base 200 cannot be rotated and changed by means of the engagement with the insertion recess 221. Also, the base bottom portion 220 is drilled with a base hole 250, into which a locking bolt 350 is inserted, at a position corresponding to the keeper hole 140. The base hole 250 is preferably drilled with a female screw to improve the screw-engagement force, if required. It is preferable that the size of the base bottom portion 220 is extended to the keeper wall 110 so that the entire missing tooth portion 430 can be covered, and the keeper bottom portion 120 for covering the base bottom portion 220 is preferably selected to conform to the size of the extended base bottom portion.

The base 200 is manufactured according to the general manufacturing method of the prosthesis, including performing impression, waxing up, casting, and the like, however, it is manufactured by using a carbon or ceramic bolt to define the accurate position of the base hole 250. The detailed manufacturing method will be described below.

Next, the structure of the body 300 of the present invention will be described in detail with reference to FIGS. 4 and 8. The body 300 is a portion replacing the missing tooth portion and is manufactured beautifully in consideration of the esthetic sense. The body 300 comprises a body main portion 310 made of steel and disposed on and engaged with the base 200, an occlusal portion 320 for defining an occlusal surface in place of the missing tooth portion, and a body plate 340.

The body main portion 310 is manufactured to conform entirely to the base bottom portion 220, the base rear wall 240, the base wall 210, and the keeper wall 110 according to the general manufacturing method of the prosthesis. Also, at least two holding pins 330 are formed at the body main portion 310 so that the occlusal portion 320 is not separated from the body main portion 310 when the occlusal portion 320 made of photo-polymer resin or ceramic material is formed at the main body portion 310. The holding pin 330 is preferably formed instantly at the body main portion 310.

The body plate 340 is provided at one side of the body main portion 310 for wrapping the abutment tooth 410 from the buccal side. While the body plate 340 wraps the abutment tooth 410 from the buccal side, the keeper plate 130 screw-engaged with the body main portion and the base plate 230 wraps the abutment teeth 410, 420 from the lingual side so that the securing force in the directions of the front and rear tooth is increased in addition to the cementing force.

Also, an engagement body hole 360 is drilled at the occlusal portion 320 and the body main portion 310 to penetrate them so that a bolt 350 can be screw-engaged into it. The body hole 360 is also drilled with a female screw to increase the screw-engagement force selectively.

FIG. 10 is an assembly view of four front tooth portions of the present invention, in which FIG. 10(*a*) is a view seen from the lingual side, FIG. 10(*b*) is a view seen from the lip side. When the front tooth portion is missing, the prosthesis of the present invention as described above, is constructed such that the body 300 is supported by both undercuts of the abutment teeth 410, 420, and the keeper 100 and the base plate 230 are engaged with each other by positioning them to face with each other and locking the bolt 350. Hereinafter the assembly method of the prosthesis with non-preparation of the present invention will be described with reference to FIG. 4 and FIG. 5.

At first, when the prosthesis arrives at the dentist, confirm if the satisfying bonding is accomplished in a mouth of a patient, and then clean the abutment tooth according to the general method thereby preparing the cementing. After completing the prepare, adhesives such as a dental resin, and the like, are sprayed on the keeper wall 110 and the keeper plate 130 of the keeper 100, so that it can be bonded to the abutment tooth 410 at one side. As the keeper wall 110, the keeper plate 130, and the keeper bottom portion 120 are manufactured to duplicate the abutment tooth 410 and the missing tooth portion 430, it is possible to perform the accurate bonding.

Then, the cementing of the base 200 is performed at the abutment tooth 420 of the other side. The cementing method is performed as follows. As the base wall 210, the base bottom portion 220, and the base plate 230 of the base 200 are manufactured to duplicate the abutment tooth 420 and the missing tooth portion 430 as they are, it is possible to perform the accurate bonding.

In addition, as the keeper 100 and the base 200 are manufactured to be inserted accurately according to the casting method described below, the keeper hole 140 and the base hole 250 for the screw-engagement are accurately aligned. Then, the body 300 is assembled onto the upper portion of the base 200. Adhesives are sprayed on the body plate 340 and bonded to wrap the abutment tooth 410 from the lip side. As the body 300 is manufactured to duplicate the entire base 200 as it is, it is possible to perform the accurate bonding. In this instance, the body hole 360 is accurately aligned so that it is screw-engaged with the keeper hole 140 and the base hole 250. Then, the base hole 360, the keeper hole 140, and the base hole 250 are penetrated by the locking bolt 350 made of stainless or titanium material to be locked, and the bolt penetrating hole is finished by the photo-polymer resin, thereby completing the operation.

As the prosthesis is assembled after it is divided into three pieces, it is not required to prepare the abutment teeth 410, 420, and it is possible to minimize the inconvenience and pains of a patient and a secondary problem. Also, the assembly accuracy and the bonding force can be radically improved in comparison with the press fitting type prosthesis according to the screw-engagement manner in addition to the general cementing. It is possible to maintain natural occlusal feelings according to the improvement of the assembly accuracy, and to minimize the operation time of the dentist to naturalize the occlusal feelings.

Next, the manufacturing method of the prosthesis with non-preparation according to the present invention will be described with reference to FIGS. 11 through 15.

In general, the manufacturing process of the prosthesis comprises an impression performing step, a working cast making step, a waxing up step, a burying step, a recalling step, and a casting step. While the manufacturing method of the present invention is similar to the general manufacturing method, however, it is different from the general manufacturing method that a carbon or ceramic bolt is employed to drill an accurate screw-engagement hole.

At first, a refractory model 500 is duplicated by using a stone model produced from the duplication of a mouth of a patient. Then, a plastic pattern corresponding to the keeper wall 110 is attached to the abutment tooth 510 of the refractory model 500 by using a parallel measuring device (suybey) 600 with wax and its surrounding portion is finished with wax to thereby form a keeper of a complete shape.

In this instance, as a plastic holder 610 is attached to the plastic pattern integrally, the holder 610 is inserted into the parallel measuring device 600 and moved to the accurate position thereby attaching it. When the attachment of the plastic pattern is completed, the holder 610 is cut, and then the keeper plate 130 is engraved by using a twenty-four gauge sheet wax and is connected to the keeper wall 110. Then, as shown in FIG. 11, the plastic pattern corresponding to the keeper bottom portion 120 is attached. It is easy to attach the plastic pattern because a plastic holder 610 is integrally formed at the plastic pattern. The plastic pattern corresponding to the keeper bottom portion 120 can be prepared as several shapes as shown in FIG. 13 according to the size and shape of the missing tooth portion 530, and it is natural that it should be selected appropriately.

Then, after all of the plastic patterns corresponding to the keeper wall 110, the keeper plate 130, and the keeper bottom portion 120 have been attached to the duplicated refractory model, as shown in FIG. 12, prosthetic operation is performed by using the carbon or ceramic bolt 620. This operation employing the bolt 620 is performed to drill the screw-engagement holes such as the keeper hole 140, the base hole 250, the body hole 360, and the like at the accurate positions so that they conform to each other, and occupies an important step in the screw-engagement type prosthesis of the present invention. The concrete shape of the ceramic bolt 620 is shown in FIG. 16. The operation employing the bolt is progressed by using the parallel measuring device 600 to determine the accurate position.

After the casting bolt 620 has been inserted into the parallel measuring device 600, it is moved to a position to drill the keeper hole 140 and filed up by the wax, and a sprue is attached at a proper position, that is, between the keeper wall 110 and the keeper plate 130, and the like. Thereafter, it is buried with the same material as that of the duplicated refractory model, is burnt out and is subjected to a primary casting. Thus, the keeper 100 drilled with a female screw is manufactured by the primary casting.

The manufacturing process of the keeper will be described in more detail by steps. The manufacturing process of the keeper includes the steps of: attaching the engraved keeper plate to the refractory model with inlay wax using sheet wax and plastic patterns corresponding to the keeper wall and the keeper bottom portion; fixing a carbon or ceramic bolt to a place, where a keeper hole will be drilled, using a parallel measuring device; forming the entire shape of the keeper by filing surrounding portions of the plastic patterns and the casting bolt on the refractory model with wax; connecting and inserting a sprue to a side of the entire keeper; buring it with the same material as that of the refractory model and burning out it; and performing casting through a path secured by the sprue.

Next, the manufacturing of the base 200 by using the secondary casting will be described.

Above all, it is very important to drill the base hole 250 to conform to the keeper hole 140 drilled at the keeper 100 manufactured by the primary casting. To accomplish the desired object, the present invention employs the titanium bolt 630 for the duplication and the ceramic bolt 620 for the casting, as shown in FIG. 16. As shown in FIG. 14, the titanium bolt 630 for the duplication is inserted into the keeper hole 140 of the metal cast keeper 100, and then entire duplication is performed with silicon impression material. In this instance, the impression performing material is filled to duplication material injection indicating portion 631 shown in FIG. 16, and then it is cured. When the curing is completed, the titanium bolt 630 for the duplication is rotated so that it can be removed by using a hexagonal wrench, and then the ceramic bolt 620 for the casting is rotated so that it can be inserted into a position according to position indicating portion 621, and filling material is injected. When the curing of the filling material is completed and is separated, the ceramic bolt 620 for the casting can be positioned at a position identical with that of the titanium bolt 630 for the duplication on the duplication model of the filling material, so that the manufacturing prepare of the secondary structure is completed. In this instance, the duplication bolt 630 includes a position selecting portion 632 for indicating a position thereof, and the casting bolt 620 includes a position selecting portion 622 adapted to guide the casting bolt 620 to a place, where the duplication bolt 630 existed, when the bolt is inserted into an impression body.

Next, the engraving of the base 200 is performed as shown in FIG. 15. In other words, the base wall 210 and the base bottom portion 220 are attached with wax, the base plate 230 is engraved by using sheet wax, and then, their surrounding portions are filled with wax to thereby engrave the base of a complete shape.

In this instance, the shape of the base wall 210 is contrary to the keeper wall 110, and faces with the duplicated keeper wall 110. As the manufacturing method is the same as that of the keeper wall 110, it is omitted. After cutting the plastic pattern corresponding to the base bottom portion 220 to conform to the size and length, a hole is drilled at a position for drilling the base hole 250, and the base wall is positioned accurately by using the holder 610 attached to the plastic pattern and is bonded by using the wax. Then, gaps such as a hole for the duplicated filling keeper 100, a vacant space, a hole for the ceramic bolt 620, and the like are filled. The base rear wall 240 and the base plate 230 are also engraved by the same method. The description thereof is omitted, as it is identical with before. Then, after cutting of the entire plastic pattern to conform to the size and the length, the base 200 is cast through the secondary casting process including filling, burning out, casting, and the like. The manufacturing process of the base will be described in more detail by steps. The base manufacturing process includes the steps of: locating the completed keeper on the refractory model; inserting the duplication bolt into the keeper hole of the keeper; duplicating the stone model, the keeper and the inserted duplication bolt with impression material; removing the stone model, the keeper and the duplication bolt after curing; inserting a carbon or ceramic bolt into a place from which the duplication bolt is removed; injecting filling material to the inside of an impression body to form a filling material model; engraving a base wall, a base bottom portion and a base plate on the filling material model; connecting and inserting a sprue to a side of the entire base; buring it with the same material as that of the refractory model and burning out it; and performing casting through a path secured by the sprue.

Next, the manufacturing process of the body 300 of the present invention will be described with reference to FIG. 15. After arranging the previously cast keeper 100 and the base 200 on the original model, and then engage them with the titanium bolt 630 for the duplication shown in FIG. 16. As was the second casting process, the third duplication model is manufactured through duplicating with using silicon impression material, inserting the ceramic bolt 620 as was performed previously, and injecting the filling material. The structure for constructing the missing tooth portion is engraved on the third duplication model by using the free wax up method. In this instance, the occlusal portion 320 for defining the occlusal surface can be defined as a metal occlusal surface, a photo-polymer occlusal surface, a porcelain occlusal surface, and the like, and although it is manufactured according to the general manufacturing method, the body hole 360 is necessarily drilled for inserting the titanium bolt 630. The body plate 340 is engraved by the twenty-four gauge wax thereby finishing the manufacturing and their surrounding portions are engraved and finished with inlay wax to thereby form the body of a complete shape.

Then, the sprue is buried in such a way as to be connected to a side of the body and the casting is performed. After the casting, the metal occlusal surface is finished as it is, and the occlusal surface is formed by the resin or the porcelain, and then completed, in case of the occlusal surface made of resin or porcelain.

When the third casting process is completed through the method as described above, it is possible to obtain the prosthesis in which the keeper hole 140, the base hole 250, and the body hole 360 are accurately aligned with each other. As respective casting process has been performed by alternatively using the particularly manufactured casting bolt 620 or the duplication bolt 630 as shown in FIG. 16, it is possible to drill the accurate screw holes to achieve simplification of the assembly and provide convenient prosthesis to a patient. The advantages of the present invention described above can be estimated as excellent in comparison with the disadvantages of the conventional press fitting type prosthesis (confer FIG. 3), and the like.

The manufacturing process of the body will be described in more detail by steps. The body manufacturing process includes the steps of: locating the completed keeper and base on the refractory model; inserting the duplication bolt into the engagement holes of the keeper and the base; duplicating the stone model, the keeper, the base and the duplication bolt with impression material; removing the stone model, the keeper, the base and the duplication bolt after curing; inserting a carbon or ceramic bolt into a place from which the duplication bolt is removed; injecting filling material to the inside of an impression body to form a filling material model; engraving the entire body shape on the filling material model with inlay wax to form the entire shape of the body; connecting and inserting a sprue to a side of the entire body; burying it with the same material that of the refractory model and burning out it; and performing casting through a course secured by the sprue.

The ceramic bolt used in the present invention is manufactured as follows.

A general ceramic bolt manufacturing method includes the steps of: mixing ceramic materials; compression-molding the mixture into a screw shape; and sintering the compressed mixture at temperature of 1,400° C. However, ceramic contraction and distortion indispensably occur during the sintering step, and hence, it is impossible to accurately manufacture the ceramic bolt. Accordingly, in case of a female screw casting method adopting the ceramic bolt produced by being sintered after the compression-molding into the screw shape, a tapping work requires much time and many efforts to indispensably re-form a female screw manually using a female screw processing tool since the ceramic bolt of the contracted and distorted state is used so that a previously manufactured coupling bolt cannot be inserted thereto. Furthermore, since a screw thread of the female screw is overlapped with a previously cast screw thread, the screw thread may be doubly formed in part, and thereby, it is impossible to accurately form the female screw. On the contrary, the ceramic bolt according to the present invention is manufactured through the steps of: mixing ceramic materials; compression-molding the mixture into a round bar of a predetermined length; sintering the round bar at temperature of 1,400° C.; and processing a screw thread of the ceramic bolt and a head, which is a coupling portion, through a turning and grinding process after contraction and deformation of the ceramic round bar is completed. Through a casting method adopting the ceramic bolt, a female screw to which a coupling bolt is accurately coupled can be formed.

The reason for this is that a dental casting process is carried out after an annealing process. The annealing is a process including the steps of burning dental wax to secure a space to which metal is inserted, removing the inside gas of filling material, and injecting metal smoothly. In this instance, since the minimum annealing temperature does not exceed 900° C., the ceramic bolt is not additionally deformed. If additional deformation and contraction of the ceramic bolt occur, temperature must be more than 1,400° C. higher than sintering temperature. Accordingly, the ceramic bolt is manufactured through the steps of: compression-molding the round bar after accurately calculating a coupling tolerance with the coupling bolt; and turning and grinding the ceramic round bard sintered at 1,400° C. Moreover, the female screw is formed by a casting method adopting the ceramic bolt.

(Second Embodiment)

Next, the second embodiment of the prosthesis with non-preparation of the present invention will be described with reference to FIG. 17 and FIG. 23.

The second embodiment is the same as the first embodiment except that various types of keeper grooves 123 are formed at the keeper bottom portion 120 of the keeper 100. The keeper 100 and the base 200 cannot be moved relatively as the keeper bottom portion 120 and the ∩ shape sectional insertion recess 221 of the base bottom portion 220 are inserted so that they can be fit to each other.

However, when the missing tooth portion is more than two as shown in FIG. 9, the engagement force can be reduced. Accordingly, in the second embodiment of the present invention, as shown in FIG. 17, various types of keeper grooves 123 are formed at a bottom inclined surface 121. In this instance, it is natural that an insertion protrusion 222 is formed at the slope of the insertion recess 221 of the base 200 so that it can be engaged with the insertion recess. It is important to form the keeper groove 123 and the insertion protrusion 222 without an undercut.

(Third Embodiment)

Next, the third embodiment of the present invention will be described with reference to FIG. 18. The third embodiment is the same as the first embodiment except that the position of the titanium bolt 630 for the duplication and the position of the ceramic bolt 620 for the casting are designed differently. The simple and wide portions of the titanium bolt 630 for the duplication and the ceramic bolt 620 for the casting make it easy to reproduce the positions, and it is possible to make a bolt with high precision.

(Fourth Embodiment)

Next, the fourth embodiment of the present invention will be described with reference to FIG. 19. The fourth embodiment is directed to a method of manufacturing the prosthesis with non-preparation without using the ceramic bolt 620 for the casting. The manufacturing process is the same as the casting process of the first embodiment except the features described below. The process described with reference to FIG. 11 through FIG. 14 will be progressed identically. After inserting the titanium bolt 630 for the duplication into the keeper hole 140 of the keeper 100 primary cast, following the manufacturing of the duplication model for the secondary casting, identical duplication is performed by using the impression material. Then, instead of inserting the ceramic bolt 620 after removing the titanium bolt 630, filling material for the casting is injected into the entire space including a space in which the titanium bolt for the duplication was positioned, thereby obtaining the same refractory model including the upper portion of the bolt for the duplication, and performing the wax work, and then performing the burying and the casting. In the manufacturing of the body 300 through the third casting, a ceramic bolt 620 can be economized by the same method. In other words, the keeper 100 and the base 200 manufactured through the primary and secondary casting are filled with the titanium bolts 630 for the duplication, and are duplicated by using impression material, and the third casting is performed by direct injecting the filling material. However, in the fourth embodiment, since the ceramic bolt 620 is omitted and direct casting is performed by using filling material, a correction wire 640 is required to prevent breakage of the shape of the bolt, as shown in FIG. 19(b). The correction wire 640 is bent roundly at the end thereof so that it is not fallen into a hole, and then the filling material is injected.

Next, with reference to FIGS. 20, 21, and 22, the drilling of female screws for the locking bolt 350 in the keeper hole 140, the base hole 250, and the body hole 360 will be described. FIG. 20 shows that all of the keeper hole 140, the base hole 250, and the body hole 360 are drilled with female screws to be engaged with each other by the locking bolt 350, and as shown in FIG. 21, the keeper hole 140 and the base hole 250 are drilled with female screws so that they can be easily engaged with each other by the locking bolt 350. FIG. 22 shows that a female screw is drilled at the keeper hole 140 and an inclination surface close contacting with lower surface of the head of the locking bolt 350 is formed at the body hole 360, and they are engaged with each other by using the locking bolt 350. The female screws drilled at the inner surface of the keeper hole 140, the base hole 250, and the body hole 360 can be drilled automatically by using the ceramic bolt having a shape identical with that of the locking bolt 350 at the time of casting the keeper 100, the base 200, and the body 300.

Meanwhile, the locking bolt 350 is manufactured into a shape identical with that of a portion corresponding to the engagement portion of the real prosthesis of the used bolt for the duplication or the used bolt for the casting.

(Fifth Embodiment)

Then, the fifth embodiment of the present invention will be described with reference to FIG. 23. The fifth embodiment is the same as the first embodiment except that the rear walls of the keeper 100 and the base 200 are omitted as shown in FIG. 23. As the rear wall of the base is omitted, the body 300 wraps the entire bottom surface of the base 200, and prevents moving of the base 200, thereby improving the engagement force.

(Sixth Embodiment)

Referring to FIG. 24, the sixth embodiment of the present invention, which is a screw-engagement type dental prosthesis with non-preparation divided into two pieces, will be described in detail as follows. Since the sixth embodiment is similar to the first embodiment except that the dental prosthesis is divided into two pieces, detailed description of the same parts as the first embodiment will be omitted.

As shown in FIG. 24, the dental prosthesis of the present invention comprises a keeper 100 wrapping an abutment tooth 410 of one side from a lingual side and a buccal side, and a body 300 wrapping an abutment tooth 420 of the other side from the lingual side and the buccal side and having a missing injured tooth portion 430.

Bolt engagement holes, which penetrate desired portions, are drilled at the keeper 100 and the body 300, by means of a casting method using the ceramic bolt and aligned in a straight line, and bolts 350 are inserted into the holes. The keeper 100 and the body 300 wrap both abutment teeth 410 and 420 from the buccal side and the lingual side, so that they can be firmly supported by means of screw engagement using common holes.

In addition, as shown in FIG. 25, since respective portion is divided into two pieces and are assembled in sequence, advantages are obtained that it is not necessary to prepare (prep) the abutment teeth 410 and 420, the inconvenience of patient is minimized, and the assembly is simple.

Respective portion is described in more detail with reference to FIGS. 24 through 26. In FIG. 26, the keeper 100 of the present invention is illustrated. In the sixth embodiment, the keeper 100 comprises a keeper wall 110 located at a side of the abutment tooth 410 and having an insertion path formed on the outer surface thereof in correspondence to an inclination of an inner inclination surface 428 of the abutment tooth 420 of the other side. Furthermore, the body 300 also has an insertion path formed on the outer wall 310 thereof, which is a main portion thereof, like the outer wall of the keeper 100.

Next, referring to FIGS. 24 and 28, the structure of the body 300 will be described in detail. The body main portion 310 is put on the keeper 100, and manufactured to conform entirely to the keeper wall 110 according to the general manufacturing method of the prosthesis. Furthermore, the body main portion put on the keeper 100 has an insertion recess drilled at a base thereof of the same shape as the keeper 100. While the body main portion 310 includes a body plate 340 provided at one side thereof for wrapping the abutment tooth 420 from the buccal side and the lingual side, the keeper 100 includes a keeper plate 130 screw-engaged with the body plate 340 and wrapping the abutment tooth 410 from the buccal side and the lingual side, so that the securing force in the directions of the front and rear teeth is increased in addition to the cementing force.

Hereinafter the assembly method of the prosthesis with non-preparation of the present invention will be described with reference to FIG. 24 and FIG. 25. Since the assembly method of the prosthesis with non-preparation is similar to the assembly method of the first embodiment, its detailed description will be omitted. This embodiment is different from the first embodiment in that the keeper wall 110 an the keeper plate 130 of the keeper 100 are sprayed with adhesives, such as a dental resin, and the like and bonded to the abutment tooth 410 at one side, and then the body 300 is assembled to the upper portion of the keeper 100. The body plate 340 is sprayed with the adhesives and bonded to the abutment tooth 420 at the other side in such a way as to wrap the abutment tooth 420 from the lingual side and the buccal side.

As the prosthesis is assembled after it is divided into two pieces, it is not required to prepare the abutment teeth 410 and 420, and it is possible to minimize the inconvenience and pains of a patient and a secondary problem.

Next, the manufacturing method of the prosthesis with non-preparation according to the present invention will be described with reference to FIGS. 29 through 31. Since the assembly method of the prosthesis with non-preparation is also similar to the manufacturing method of the first embodiment, its detailed description will be omitted. This embodiment is different from the first embodiment in that the keeper 100 is completed by a primary casting and then the body 300 is manufactured by a secondary casting.

A manufacturing process of the body 300 by the secondary casting will be described as follows.

A keeper hole 140 is drilled at the keeper 100 manufactured by the primary casting, and hence, above all, it is very important to drill a body hole 360 to conform to the keeper hole 140 drilled at the keeper 100 manufactured by the primary casting. To accomplish the desired object, the present invention employs a titanium bolt 630 for duplication and a ceramic bolt 620 for casting, as shown in FIGS. 16 and 18. As shown in FIG. 40, the titanium bolt 630 for the duplication is inserted into the keeper hole 140 of the metal cast keeper 100, and then entire duplication is performed with silicon impression material. In this instance, the impression performing material is filled to an injection indicating portion shown in FIGS. 16 and 18, and then it is cured.

When the curing is completed, the titanium bolt 630 for the duplication is rotated using a hexagonal wrench so that it is removed, the stone model and the keeper are removed from an impression body, and then the ceramic bolt 620 for the casting is rotated so that it can be inserted into a position, where the titanium bolt was placed, according to the bolting indicating portion, and filling material is injected. When the curing of the filling material is completed and the filling material is separated from the impression body, the ceramic bolt 620 for the casting can be positioned at a position identical with that of the titanium bolt 630 for the duplication on the duplication model of the filling material, so that the manufacturing preparation of the secondary structure is completed.

A structure for constructing the missing tooth is engraved on the second duplication model by using the free wax up method. In this instance, the occlusal portion 320 for defining the occlusal surface can selectively adopt a metal occlusal surface, a photo-polymer occlusal surface, a porcelain occlusal surface, and the like, and although it is manufactured according to the general manufacturing method, the body hole 360 is necessarily drilled for inserting the titanium bolt. The body plate 340 is engraved by the twenty-four gauge sheet wax thereby finishing the manufacturing. Then, the sprue is buried and the casting is performed. After the casting, the metal occlusal surface is finished as it is, and the occlusal surface is formed by the resin or the porcelain, and then completed, in case of the occlusal surface made of resin or porcelain.

When the second casting process is completed through the method as described above, it is possible to obtain the prosthesis in which the keeper hole 140 and the body hole 360 are accurately aligned with each other. As respective casting process has been performed by alternatively using the particularly manufactured ceramic bolt 620 or the titanium bolt 630 as shown in FIGS. 16 and 18, it is possible to drill the accurate screw holes to achieve simplification of the assembly and provide a convenient prosthesis to a patient. The above-mentioned advantages of the present invention can be estimated as excellent in comparison with the disadvantages of the conventional press fitting type prosthesis (confer FIG. 3), and the like.

(Seventh Embodiment)

Next, the seventh embodiment of the prosthesis with non-preparation of the present invention will be described with reference to FIG. 32.

The seventh embodiment is the same as the sixth embodiment except that various types of keeper grooves 123 are formed at the keeper bottom portion 120 of the keeper 100. The keeper 100 and the body 300 cannot be moved relatively as the keeper bottom portion 120 and an insertion recess 321 of a body bottom portion 320 are inserted so that they are can be fit to each other.

However, when the missing tooth portion is more than two as shown in FIG. 28, the engagement force may be reduced. Accordingly, in the seventh embodiment of the present invention, as shown in FIG. 32, various types of keeper grooves 123 are formed at a bottom inclined surface 121 of the keeper bottom portion 120. In this instance, it is natural that an insertion protrusion 322 is formed at the insertion recess 321 of the body 300 so that it can be engaged with the insertion recess. It is important to form the insertion groove 123 and the insertion protrusion 322 without an undercut. Female screws are automatically formed on the inner surfaces of the keeper hole 140 and the body hole 360 by using the ceramic bolt of the same shape as the locking bolt 350 when casting of the keeper 100 and the body 300 is performed.

(Eighth Embodiment)

In case where the abutment tooth, on which the keeper is put, is the rearmost tooth, as shown in FIG. 33, the keeper plate of the buccal side and the lingual side is connected to the distal center of the abutment tooth to thereby increase an occlusal supporting force still more. In this instance, there is no undercut at the distal center side of the abutment tooth. After the above, processes of manufacturing the body are the same as working processes of a molar tooth portion.

(Ninth Embodiment)

Referring to FIGS. 34 and 35, the ninth embodiment of the present invention, which is a screw-engagement type dental prosthesis with non-preparation (preparation), will be described in detail as follows. Since the ninth embodiment is similar to the sixth embodiment except that the prosthesis has semi-conical keys 180 and 380, detailed description of the same parts as the first embodiment will omitted. In addition, as shown in FIG. 35, since respective portion is divided into two pieces and are assembled in sequence, advantages are obtained that it is not necessary to reduce prepare the abutment teeth 410 and 420, and the inconvenience of the a patient is minimized and the assembly is simple. Furthermore, the keys 180 and 380 are formed on the keeper and the body in correspondence to maintaining portions 419 and 429 formed on the inner inclination surfaces of the abutment teeth of both sides to thereby be firmly supported, so that the front teeth portion can be maximized in aesthetic point of view.

In the ninth embodiment, the inner surface of the keeper wall 110 is manufactured to duplicate the undercut of the abutment tooth 410 as it is according to the general manufacturing method of the prosthesis, and in this instance, the keys 180 and 380 substantially duplicating the thin and semi-conical maintaining portions 419 and 429 previously formed on the inner inclination surface of the abutment tooth are formed. The support force of the prosthesis is more increased by a close contact between the key 180 of the inner surface of the keeper wall 110 and the maintaining portion 419 of the abutment tooth 410. In the meanwhile, the keeper plate 130 is manufactured in such a way as to wrap the abutment tooth 410 from the buccal side and the lingual side and substantially duplicate the shape of the abutment tooth 410 like the keeper wall 110. The inner inclination surface of the keeper, to which both keeper plates are connected, is manufactured together with the keys 180 and 380 substantially duplicating the thin and semi-conical maintaining portions 419 and 429 formed on the inner inclination surface of the abutment tooth.

Next, referring to FIGS. 34 and 37, the structure of the body 300 will be described in detail. The body 300 includes an occlusal portion 320, which defines an occlusal surface in place of the missing tooth portion of the main portion 310 put on the keeper 100, and a body plate 340. The inner inclination surface of the keeper, to which both keeper plates are connected, is manufactured together with the keys 180 and 380 substantially duplicating the thin and semi-conical maintaining portions 419 and 429 formed on the inner inclination surface of the abutment tooth.

While the body main portion 310 includes the body plate 340 provided at one side thereof for wrapping the abutment tooth 420 from the buccal side and the lingual side, the keeper 100 includes the keeper plate 130 screw-engaged with the body plate 340 and wrapping the abutment tooth 410 from the buccal side and the lingual side, so that the securing force in the directions of the front and rear teeth is increased in addition to the cementing force. The inner inclination surface of the keeper, to which both keeper plates are connected, is manufactured together with the keys 180 and 380 substantially duplicating the thin and semi-conical maintaining portions 419 and 429 formed on the inner inclination surface of the abutment tooth.

(Tenth Embodiment)

Referring to FIG. 38, the tenth embodiment of the present invention will be described in detail as follows. The tenth embodiment is the same as the ninth embodiment except that various types of keeper grooves 123 are formed at the keeper bottom portion 120 of the keeper 100. Since the detailed description of the tenth embodiment is the same as the seventh embodiment, it will be omitted.

(Eleventh Embodiment)

In case where the abutment tooth, on which the keeper is put, is the rearmost tooth, as shown in FIG. 39, the keeper plate of the buccal side and the lingual side is connected to the distal center of the abutment tooth to thereby increase an occlusal supporting force still more. The detailed description of the eleventh embodiment is the same as the eighth embodiment.

Hereinafter, the manufacturing process of the prosthesis including a keeper male and a body female will be described.

In hospitals, generally, a filling material model is made by duplicating a stone model, and then, a keeper plate, a keeper outer wall and the keeper male are engraved using various kinds of wax. The keeper plate is simply engraved by using a twenty-four gauge sheet wax, and the keeper outer wall and the keeper male respectively have insertion paths of the same angle as an inner inclination surface of the abutment of the other side. In this instance, while keys are not formed in case of non-preparation, a thin and semi-conical maintaining portion is formed on an inner inclination surface of the abutment of a side in case of a small preparation. In this instance, in case of the front tooth portion, since the maintaining portion of the lip side, which is an extension portion of the keeper outer wall, can be minimized, an aesthetically satisfying prosthesis can be obtained.

After engraving is completed, a sprue is formed according to a general method and buried in filling material, and the casting is performed. The cast keeper is seated on the stone model through a grinding process. The keeper of the present invention is seated on the stone model using a very simple duplicating method in comparison with that of the prior art taking a delicate duplicating process requiring a high-grade skill to provide accuracy in positioning the bolt. A body is engraved from the filling material model formed by duplicating the stone model and the keeper seated on the stone model together. Since a body outer wall and a body female are directly engraved on the filling material model, on which the keeper outer wall and the keeper plate are duplicated, the body outer wall and the body female having the same insertion paths as the keeper outer wall and the keeper male are formed automatically. Moreover, also the body plate is engraved by using a twenty-four gauge sheet wax in the same method as the above, and the maintaining portion of the lip side is minimized in case where a key is formed at the front tooth portion.

Next, an occlusal surface is formed by wax in case of a metal engagement portion, and an occlusal portion is formed in consideration of a portion on which resin or porcelain in case of a resin occlusal surface or a porcelain occlusal surface. Especially, in case of the resin occlusal portion, a maintaining portion is additionally formed for a mechanical engagement of resin and metal. After the entire waxing work is completed, a sprue is formed according to the general method and buried, and the casting and grinding are performed in sequence. Through the above process, a prosthesis, in which the keeper having the keeper male and the body having the body female are engaged with each other, is completed.

In case of a molar tooth portion, the present invention includes an insertion path substantially wrapping the maximum overlap of a suprabulge portion of the lingual side and an adjacent surface of the lip side, the insertion path conforming to both adjacent surfaces of the abutment teeth of both sides and insertion paths of the adjacent surfaces.

Since the keeper male is located at the center of a space, where an artificial tooth will be located, with the substantially maximum size thereof, the artificial tooth having the body female disposed at the inner center thereof and engaged with the keeper male at the maximum friction area can endure the occlusal pressure in stable. The present invention applies a method of obtaining friction force of a double-pipe prosthesis, which is a dental prosthesis manufacturing method. The double-pipe prosthesis is obtained through the steps of preparing a tooth without any undercut, performing impression, making a model, and making a metal inner pipe. When an outer pipe is made on the inner pipe after a milling work is performed on the outer surface of the inner pipe at a predetermined angle, a removable prosthesis having the maximum friction force between the outer surface of the inner pipe and the inner surface of the outer pipe can be manufactured. Since the present invention wraps the adjacent surfaces of the lingual side and the lip side in case of the front tooth portion and wraps the buccal side and the lingual side in case of the molar tooth portion while wrapping both adjacent surfaces, due to synergism of the maximum friction force between the keeper male and the body female, the present invention can substantially counteract to the occlusal pressure applied during chewing.

The keeper outer wall and the body outer wall are coupled with each other by conforming the keeper outer wall with the insertion path of the keeper male from the insertion path formed along the inner inclination surface of the abutment tooth of the other side, and the insertion path causes synergism of the friction force of the inner inclination surfaces of both abutment teeth together with the maximum coupling force of the keeper male and the body female. Accordingly, when the prosthesis is assembled in sequence, reciprocal maintaining forces are generated from the inner inclination surface of the abutment tooth of one side, the keeper wall and the body outer wall, and the keeper male, the body female and the inner inclination surface of the abutment tooth of the other side.

That is, the present invention is simply manufactured into two pieces and is the double-pipe prosthesis according to a method applying the maximum friction force of the double-pipe prosthesis. In the double-pipe prosthesis, the female corresponding to an inner face of an outer pipe is inserted into the male corresponding to an outer face of an inner pipe without any space, so that a semi-conical maintaining recess directly acts to maintain the artificial tooth without any hindrance to the insertion path in a state where the maximum maintaining force is kept, and a semi-conical maintaining recess of the other side is integrated with the artificial tooth and directly maintains the artificial tooth together with the female coupled with the male through friction.

(Twelfth Embodiment)

Referring to FIG. 41, the twelfth embodiment of the present invention will be described in detail as follows. Since the twelfth embodiment is similar to the sixth and ninth embodiments, detailed description of the same parts as the sixth and ninth embodiments will be omitted.

As shown in FIG. 41, the dental prosthesis of the present invention having a keeper male and a body female comprises a keeper 100 wrapping an abutment tooth 410 of one side from a lingual side and a buccal side, and a body 300 wrapping an abutment tooth 420 of the other side from the lingual side and the buccal side and having a missing injured tooth portion 430.

The keeper 100 includes a keeper male 101 acting as a substitute for an engagement force of a bolt, and the body 300 includes a body female 301 engaged with the keeper male through friction resistance. The body female 301 is drilled at a space 303 of an end portion of an insertion recess.

The keeper 100 and the body 300 wrap the abutment teeth 410 and 420 from the buccal side and the lingual side, so that can be firmly supported through the firm friction resistance between the keeper male and the body female.

According to a small preparation method of FIG. 40, keys 180 and 380 are formed on the keeper and the body in correspondence to maintaining portions 419 and 429 formed on the inner inclination surfaces of the both abutment teeth to provide a firm support, whereby the front tooth portion is maximized in aesthetic point of view.

Respective portion is described in more detail with reference to FIGS. 40 through 42. In FIG. 42, the keeper 100 of the present invention is illustrated. The keeper 100 comprises a keeper wall 110, a keeper bottom portion 120, a keeper plate 130 and the keeper male 101. The keeper bottom portion 120 is inserted into an insertion recess of the body 300, and the keeper male is disposed at a proper position of the keeper bottom portion 120.

Next, referring to FIGS. 26, 44 and 47, the structure of the body 300 will be described in detail. The body 300 acts as a substitute for the missing tooth, and hence, is manufactured in consideration of an aesthetic point of view. The body 300 includes an occlusal portion 320, which defines an occlusal surface in place of the missing tooth portion of a main portion 310 put on the keeper 100, and a body plate 340. In case of a small preparation, a key 380 substantially duplicating the thin and semi-conical maintaining portions 419 and 429 previously formed on the inner inclination surface of the abutment tooth is disposed on the inner inclination surface of the body, to which both body plates are connected. In case of a non-preparation method, the key is not disposed.

The body female 301 is disposed at a base portion of the main portion 310 for wrapping the abutment tooth 420 from the buccal side and the lingual side and engaged with the keeper male through the friction resistance. Furthermore, the body plate is disposed on the body main portion for wrapping the abutment tooth 420 from the buccal side and the lingual side.

Hereinafter the assembly method of the prosthesis of the present invention will be described with reference to FIGS. 40 and 41. At first, when the prosthesis arrives at the dentist, confirm if the satisfying bonding is accomplished in the mouth of a patient, and then clean the abutment tooth according to the general method thereby preparing the cementing. After completing the preparation, adhesives such as a dental resin, and the like, are sprayed on the keeper wall 110 and the keeper plate 130 of the keeper 100 and, so that it can be bonded to the abutment tooth 410 at one side. As the keeper wall 110, the keeper plate 130, and the keeper bottom portion 120 are manufactured to duplicate the abutment tooth 410 and the missing tooth portion 430 as they are, it is possible to perform the accurate bonding. Then, the body 300 is assembled to an upper portion of the keeper 100. Then, the body 300 is assembled onto the upper portion of the keeper 100. Adhesives are sprayed on the body plate 340 and the body plate 340 is bonded to the abutment tooth 420 to wrap the abutment tooth 420 from the lingual side and the buccal side. As the body 300 is also manufactured to duplicate a contacting portion of the keeper 100 as it is, it is possible to perform the accurate bonding. In this instance, the body female 301 is accurately conform to the keeper male 101 so that it can be assembled with the keeper male 101 through friction force.

A plastic pattern corresponding to the keeper bottom portion 120 can be prepared in various forms as shown in FIG. 45 according to sizes and forms of the missing tooth portion 530, and it is natural that it can be selected properly.

(Thirteenth Embodiment)

Referring to FIG. 47, the thirteenth embodiment of the present invention will be described in detail as follows. The thirteenth embodiment is the same as the twelfth embodiment except that various types of keeper grooves 123 are formed at the keeper bottom portion 120 of the keeper 100. Since the detailed description of the thirteenth embodiment is the same as the seventh embodiment, it will be omitted.

(Fourteenth Embodiment)

In case where the abutment tooth, on which the keeper is put, is the rearmost tooth, as shown in FIG. 48, the keeper plate of the buccal side and the lingual side is connected to the distal center of the abutment tooth to thereby increase an occlusal supporting force still more. The detailed description of the fourteenth embodiment is the same as the eighth embodiment.

Industrial Applicability

As described above, while the present invention has been described with reference to the particular matters, illustrative embodiments and drawings, they are provided to promote a general understanding and it is not to be restricted by the embodiments. It is to be appreciated that those skilled in the art can change or modify the embodiments of the present invention in various ways.

Accordingly, the idea of the present invention is not limited by the embodiments, and all modifications equivalent to claims of the present invention belong to the scope and spirit of the present invention.

The invention claimed is:

1. A dental prosthesis for restoring a missing tooth, comprising:
    a keeper configured to embrace a lingual side of a first abutment tooth disposed at a first side of a missing tooth portion;
    a base configured to embrace a lingual side of a second abutment tooth disposed at a second side of the missing tooth portion; and
    a body configured to serve as an artificial tooth and engage with the keeper and the base by a screw, and further configured to embrace a buccal side of the first abutment tooth or the second abutment tooth,
    wherein the base is provided with a base rear wall configured to support a rear wall of the body,
    wherein the keeper includes a keeper bottom portion adapted to sit in the missing tooth portion defined by the first and the second abutment teeth,
    wherein the base includes a base bottom portion, and wherein the base bottom portion includes an insertion recess into which the keeper bottom portion is inserted, the insertion recess having a screw hole configured to engage with the screw.

2. A dental prosthesis for a molar tooth for restoring a missing tooth, comprising:
    a keeper configured to embrace both of a lingual side and a buccal side of a first abutment tooth disposed at a first side of a missing tooth portion; and
    a body configured to embrace both of a lingual side and a buccal side of a second abutment tooth disposed at a second side of the missing tooth portion, the body further configured to serve as an artificial tooth and engage with the keeper by a screw,
    wherein the keeper includes a keeper bottom portion adapted to sit in the missing tooth portion located between the first and the second abutment teeth,
    wherein the body includes a body bottom portion, and wherein the body bottom portion includes an insertion recess into which the keeper bottom portion is inserted, the insertion recess having a screw hole configured to engage with the screw.

3. A dental prosthesis for a front tooth for restoring a missing tooth, comprising:
a keeper configured to embrace both of a lingual side and a lip side of a first abutment tooth disposed at a first side of a missing tooth portion; and
a body configured to embrace both of a lingual side and a lip side of a second abutment tooth disposed at a second side of the missing tooth portion, the body configured to serve as an artificial tooth and engage with the keeper by a screw,
wherein the keeper includes a keeper bottom portion adapted to sit in the missing tooth portion located between the first and the second abutment teeth,
wherein the body includes a body bottom portion, and
wherein the body bottom portion includes an insertion recess into which the keeper bottom portion is inserted, the insertion recess having a screw hole configured to engage with the screw.

* * * * *